United States Patent
Posner et al.

(10) Patent No.: US 9,611,273 B2
(45) Date of Patent: Apr. 4, 2017

(54) TRIOXANE THIOACETAL MONOMERS AND DIMERS AND METHODS OF USE THEREOF

(71) Applicant: THE JOHNS HOPKINS UNIVERSITY, Baltimore, MD (US)

(72) Inventors: Gary H. Posner, Baltimore, MD (US); Alexander M. Jacobine, Baltimore, MD (US); Rachel D. Slack, Baltimore, MD (US); Jennifer R. Mazzone, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 14/381,494

(22) PCT Filed: Feb. 28, 2013

(86) PCT No.: PCT/US2013/028188
§ 371 (c)(1),
(2) Date: Aug. 27, 2014

(87) PCT Pub. No.: WO2013/130725
PCT Pub. Date: Sep. 6, 2013

(65) Prior Publication Data
US 2015/0031677 A1    Jan. 29, 2015

Related U.S. Application Data

(60) Provisional application No. 61/604,032, filed on Feb. 28, 2012.

(51) Int. Cl.
C07D 211/70    (2006.01)
A61K 31/335   (2006.01)
(Continued)

(52) U.S. Cl.
CPC .......... *C07D 493/22* (2013.01); *A61K 31/357* (2013.01); *A61K 31/4192* (2013.01);
(Continued)

(58) Field of Classification Search
CPC .............................. C07D 493/18; A61K 31/57
(Continued)

(56) References Cited

U.S. PATENT DOCUMENTS 7,910,750 B2 *  3/2011  Li et al. .................. 549/348
2005/0148598 A1   7/2005  O'Neill et al.

FOREIGN PATENT DOCUMENTS

WO    2010135427 A2    11/2010

OTHER PUBLICATIONS

Venugopalan et al, European Journal of Medicinal Chemistry (1995), 30(9), 697-706, Antimalarial activity of new ethers and thioethers of dihydroartemisinin.*

(Continued)

*Primary Examiner* — Erich Leeser
(74) *Attorney, Agent, or Firm* — Jeffrey W. Childers; Michael Best & Friedrich LLP

(57) ABSTRACT

Monomeric and dimeric trioxane thioacetals and methods of their use for treating subjects infected with malaria or other parasitic infectious diseases including, but not limited to, toxoplasmic infection; subjects afflicted with psychiatric conditions associated with toxoplasmic infection; and subjects afflicted with cancer.

15 Claims, 5 Drawing Sheets

(51) Int. Cl.
    C07D 493/22    (2006.01)
    C07D 493/18    (2006.01)
    A61K 45/06     (2006.01)
    A61K 31/4709   (2006.01)
    A61K 31/357    (2006.01)
    A61K 31/4192   (2006.01)

(52) U.S. Cl.
    CPC .......... *A61K 31/4709* (2013.01); *A61K 45/06* (2013.01); *C07D 493/18* (2013.01)

(58) Field of Classification Search
    USPC ........................................ 549/348; 514/450
    See application file for complete search history.

(56) References Cited

OTHER PUBLICATIONS

Oh et al, Bioorganic & Medicinal Chemistry 12 (2004) 3783-3790, Synthesis and antiangiogenic activity of thioacetal artemisinin derivatives.*
Wolff, Manfred E., Burger's Medicinal Chemistry and Drug Discovery, Fifth Ed., vol. 1: Principles and Practice, John Wiley & Sons, 1995, 975.*
Banker, Gilbert S. et al., Modem Pharmaceutics, Marcel Dekker, New York, 1996.*
West, Anthony R., Solid State Chemistry and Its Applications, Wiley, New York, 1988, 358.*
Ashley, E. A.; White, N. J. Artemisinin-based combinations. Curr. Opin. Infect. Dis. 2005, 18, 531-536.
Bachmann, S., J. Schroder, C. Bottmer, E. F., Torrey, and R. H. Yolken. 2005. Psychopathology in first-episode schizophrenia and antibodies to Toxoplasma gondii. Psychopathol. 38(2): 87-90.
Begue J-P, Bonnet-Delpon D. Fluoroartemisinins: metabolically more stable antimalarial artemisinin derivatives. Chem Med Chem 2007, 2, 608-624.
Bigot A, Breit B. A convenient allylic functionalization of bis(prop-2-enyl)methanol by direct trimetalation. Synthesis 2008, 22, 3692-3696.
Chadwick J, Mercer AE, Park BK, Cosstick R, O'Neill PM. 2009. Synthesis and biological evaluation of extraordinarily potent C-10 carba artemisinin dimers against P-falciparum malaria parasites and HL-60 cancer cells. BioorgMed Chem 17: 1325-1338.
Chen, X.; Chong, C. R; Shi, L; Yoshimoto, T.; Sullivan, D. J. , Jr.; Lin, J. O. Inhibitors of Plasmodium falciparum methionine aminopeptidase Ib possess antimalarial activity. Proc. Natl. Acad. Sa. U.S.A. 2006, 103, 14548-14553.
Fanello, C.I.; Karema, C; van Doren, W.; Van Overmeir, C; Ngamije, D.; D'Alessandro, U . A randomised trial to assess the safety and efficacy of artemether-lumefantrine (Coartem®) for the treatment of uncomplicated Plasmodium falciparum malaria in Rwanda. Trans. R. Soc. Trop. Med. Hyg. 2007, 101, 344-350.
Gautam, A.; Ahmed, T.; Batra, V.; Paliwal, J., Pharmacokinetics and Pharmacodynamics of Endoperoxide Antimalarials. Curr. Drug. Metab. 2009, 10, 289-306.
Gately, S.; West, R. Novel Therapeutics With Enhanced Biological Activity Generated by the Strategic Introduction of Silicon Isosteres into Known Drug Scaffolds. Drug Dev. Res. 2007, 68, 156-163.
Georgiev, V. S. 1994. Management of toxoplasmosis. Drugs. 48(2):179-188.
Greene, T. W.; Wuts, P. G. M., Protective Groups in Organic Synthesis. Third ed.
Haynes, R. K. From artemisinin to new artemisinin antimalarials: biosynthesis, extraction, old and new derivatives, stereochemistry and medicinal chemistry requirements. Curr Top Med Chem 2006, 6, 509-537.

Hof, Fraser; Schütz, Andri; Fäh, Christoph; Meyer, Solange; Bur, Daniel; Liu, Jun; Goldberg, D.E.; Diederich, F. Starving the Malaria Parasite: Inhibitors Active Against the Aspartic Proteases Plasmepsins I, II, and IV. Angew. Chem. Int. Ed. 2006, 45, 2138-2141.
Jefford, C. W. Synthetic peroxides as antimalarials. Curr Opin Invest Drugs (Thomson Set.) 2004, 5, 866-872.
Jones-Brando, L., E. F. Torrey, and R. Yolken. 2003. Drugs used in the treatment of schizophrenia and bipolar disorder inhibit the replication of Toxoplasma gondii. Schizophr. Res. 62:237-244.
Jung, M.; Lee, S., Bioorg. Med. Chem. Lett. 1998, 8, 1003-1006.
Jung, M.; Lee, S.; Ham, J.; Lee, K.; Kim, H.; Kim, S. K., Antitumor activity of novel deoxoartesmisinin monomers, dimers, and trimer. J. Med. Chem. 2003, 46, 987-994.
Kelly, J. X.; Smilkstein, M. J.; Brun, R; Wittlin, S.; Cooper, R A.; Lane, K. D.; Janowsky, A.; Johnson, R. A.; Dodean, R. A.; Winter, R.; Hinrichs, D. J.; Riscoe, M. K. Discovery of dual function acridones as a new antimalarial chemotype. Nature 2009, 459, 270-273.
Klayman, D. L. Qinghaosu (artemisinin): an antimalarial drug from China. Science 1985, 228, 1049-1055.
Lin A. J., D. L. Klayman, and W. K Milhous. 1987. Antimalarial activity of new water-soluble dihydroartemisinin derivatives. J. Med. Chem. 30:2147-2150.
Oh, S.; Jeong, I. H.; Shin, W.-S.; Lee, S., Bioorg. Med. Chem. Lett. 2003, 13, 3665-3668.
Olliaro, P. L.; Boland, P. B. Clinical public health implications of antimalarial drug resistance. In Antimalarial Chemotherapy: Mechanisms of Action, Resistance, and New Directions in Drug Discovery; Rosenthal, P. J., Ed.; Humana Press: Totowa, NJ, 2001; pp. 65-83.
Paik I-H, Xie S, Shapiro TA, Labonte T, Sarjeant AAN, Baege AC, Posner GH. 2006. Second generation, orally active, antimalarial, artemisinin-derived trioxane dimers with high stability, efficacy, and anticancer activity. J Med Chem 2006, 49, 2731-2734.
Plowe, C. V., Curr. Top. Microbiol. Immunol. 2005, 295, 55-79.
Posner, G H.; Paik, I.-H.; Sur, S.; McRiner, A. J.; Borstnik, K.; Xie, S.; Shapiro, T. A., Orally active, antimalarial, anticancer, artemisinin-derived trioxane dimers with high stability and efficacy J. Med. Chem. 2003, 46, 1060-1065.
Posner G H., Paik L-H., Chang W., Borstnik K., Sinishtaj S., Rosenthal A. S., Shapiro T. A. Malaria-infected mice are cured by a single dose of novel artemisinin derivatives. J Med Chem 2007, 50, 2516-2519.
Posner G. H., Chang W., Hess L., Woodard L., Sinishtaj S., Usera A. R, Maio W., Rosenthal A. S., Kalinda A. S., D'Angelo J. G, Petersen K. S., Stohler R., Chollet J., Santo-Tomas J., Synder C, Rottmann M., Within S., Brun R, Shapiro T. A. Malaria-infected mice are cured by oral administration of new artemisinin derivatives. J Med Chem 2008, 51, 1035-1042.
Ramanathan-Girish, S.; Catz, P.; Creek, M. R; Wu, B.; Thomas, D.; Krogstad, D. J., De, D.; Mirsalis, J. C; Green, C. E. Pharmacokinetics of the Antimalarial Drug, AQ-13, in Rats and Cynomolgus Macaques. Int. J. Toxicol. 2004, 23, 179-189.
Ridley, R. G. Medical Need, Scientific Opportunity, and the Drive for Antimalarial Drugs. Nature 2002, 415, 686-693.
Lee, S.; Oh, S.; Park, G.-M.; Kim, T.-S.; Ryu, J.-S.; Choi, H.-K., Antimalarial activity of thiophenyl- and benzenesulfonyl-dihydroartemisinin. Korean J. Parasitol. 2005, 43, 123-126.
Satchell, D. P. N.; Satchell, R. S. Mechanisms of hydrolysis of thioacetals. Chem. Soc. Rev. 1990, 19, 55-81.
Slack, R. D.; Mott, B. M.; Woodard, L. E.; Tripathi, A.; Sullivan, D.; Nenortas, E.; Girdwood, S. C. T.; Shapiro, T. A.; Posner, G. H, Malaria-Infected Mice Are Completely Cured by One 6 mg/kg Oral Dose of a New Monomeric Trioxane Sulfide Combined with Mefloquine. J. Med. Chem. 2012, 55, 291-296.
Tang Y, Dong Y, Vennerstrom JL. 2004. Synthetic peroxides as antimalarials. Med Res Rev 2004, 24, 425-448.
Troye-Blomberg, M.; Berzins, K. Rational Vaccine Development against Malaria. Microbes Infect. 2007, 9, 749-750.

(56) References Cited

OTHER PUBLICATIONS

Vennerstrom, J. L.; Arbe-Barnes, S.; Brun, R.; Charman, S. A.; Chiu, F. C. K.; Chollet, J.; Dong, Y.; Dorn, A.; Hunziker, D.; Matile, H.; McIntosh, K.; Padmanilayam, M.; Santo, T. J.; Scheurer, C; Scorneaux, B.; Tang, Y.; Urwyler, H.; Wittlin, S.; Charman, W. N. Identification of an antimalarial synthetic trioxolane drug development candidate. Nature 2004, 430, 900-904.

Venugopalan, B.; Karnik, P. J.; Bapat, C. P.; Chatterjee, D. K.; Iver, N.; Lepcha, D. Antimalarial activity of new ethers and thioethers of dihydroartemisinin. Eur. J. Med. Chem. 1995, 30, 697-706.

World Health Organization. Guidelines for the Treatment of Malaria. First Edition; WHO: Geneva, Switzerland, 2006.

World Malaria Report 2011; World Health Organization: Geneva.

Ashley and White Artemisinin-based combinations. Curr. Opin. Infect. Dis. 2005, 18, 531-536.

Bachmann et al. 2005. Psychopathology in first-episode schizophrenia and antibodies to Toxoplasma gondii. Psychopathol. 38(2): 87-90.

Begue and Bonnet-Delpon Fluoroartemisinins: metabolically more stable antimalarial artemisinin derivatives. Chem Med Chem 2007, 2, 608-624.

Bigot and Breit A convenient allylic functionalization of bis(prop-2-enyl)methanol by direct trimetalation. Synthesis 2008, 22, 3692-3696.

Chadwick et al. 2009. Synthesis and biological evaluation of extraordinarily potent C-10 carba artemisinin dimers against P-falciparum malaria parasites and HL-60 cancer cells. BioorgMed Chem 17: 1325-1338.

Chen et al. Inhibitors of Plasmodium falciparum methionine aminopeptidase Ib possess antimalarial activity. Proc. Natl. Acad. Sa. U.S.A. 2006, 103, 14548-14553.

Fanello et al. A randomised trial to assess the safety and efficacy of artemether-lumefantrine (Coartem®) for the treatment of uncomplicated Plasmodium falciparum malaria in Rwanda. Trans. R. Soc. Trop. Med. Hyg. 2007, 101, 344-350.

Gately and West Novel Therapeutics With Enhanced Biological Activity Generated by the Strategic Introduction of Silicon Isosteres into Known Drug Scaffolds. Drug Dev. Res. 2007, 68, 156-163.

Hof et al. Starving the Malaria Parasite: Inhibitors Active Against the Aspartic Proteases Plasmepsins I, II, and IV. Angew. Chem. Int. Ed. 2006, 45, 2138-2141.

Jones-Brando et al. 2003. Drugs used in the treatment of schizophrenia and bipolar disorder inhibit the replication of Toxoplasma gondii. Schizophr. Res. 62:237-244.

Jung and Lee Bioorg. Med. Chem. Lett. 1998, 8, 1003-1006.

Jung et al. Antitumor activity of novel deoxoartesmisinin monomers, dimers, and trimer. J. Med. Chem. 2003, 46, 987-994.

Kelly et al. Discovery of dual function acridones as a new antimalarial chemotype. Nature 2009, 459, 270-273.

Klayman Qinghaosu (artemisinin): an antimalarial drug from China. Science 1985, 228, 1049-1055.

Lin et al. 1987. Antimalarial activity of new water-soluble dihydroartemisinin derivatives. J. Med. Chem. 30:2147-2150.

Oh et al. Bioorg. Med. Chem. Lett. 2003, 13, 3665-3668.

Paik et al. 2006. Second generation, orally active, antimalarial, artemisinin-derived trioxane dimers with high stability, efficacy, and anticancer activity. J Med Chem 2006, 49, 2731-2734.

Plowe Curr. Top. Microbiol. Immunol. 2005, 295, 55-79.

Posner et al. Orally active, antimalarial, anticancer, artemisinin-derived trioxane dimers with high stability and efficacy J. Med. Chem. 2003, 46, 1060-1065.

Posner et al. Malaria-infected mice are cured by a single dose of novel artemisinin derivatives. J Med Chem 2007, 50, 2516-2519.

Posner et al. Malaria-infected mice are cured by oral administration of new artemisinin derivatives. J Med Chem 2008, 51, 1035-1042.

Ramanathan-Girish et al. Pharmacokinetics of the Antimalarial Drug, AQ-13, in Rats and Cynomolgus Macaques. Int. J. Toxicol. 2004, 23, 179-189.

Ridley Medical Need, Scientific Opportunity, and the Drive for Antimalarial Drugs. Nature 2002, 415, 686-693.

Slack et al. Malaria-Infected Mice Are Completely Cured by One 6 mg/kg Oral Dose of a New Monomeric Trioxane Sulfide Combined with Mefloquine. J. Med. Chem. 2012, 55, 291-296.

Satchell and Satchell Mechanisms of hydrolysis of thioacetals. Chem. Soc. Rev. 1990, 19, 55-81.

Tang et al. 2004. Synthetic peroxides as antimalarials. Med Res Rev 2004, 24, 425-448.

Troye-Blomberg and Berzins Rational Vaccine Development against Malaria. Microbes Infect. 2007, 9, 749-750.

Vennerstrom et al. Identification of an antimalarial synthetic trioxolane drug development candidate. Nature 2004, 430, 900-904.

Venugopalan et al. Antimalarial activity of new ethers and thioethers of dihydroartemisinin. Eur. J. Med. Chem. 1995, 30, 697-706.

Lee et al. Antimalarial activity of thiophenyl- and benzenesulfonyl-dihydroartemisinin. Korean J. Parasitol. 2005, 43, 123-126.

International Search Report dated Jun. 21, 2013 from PCT International Application No. PCT/US2013/028188.

* cited by examiner

5a, n = 3, m = 3
5b, n = 3, m = 6
5c, n = 6, m = 3
5d, n = 6, m = 6 n = 3 or 6

Linkers meta
para meta
para m = 2
m = 4
m = 6
m = 8
m = 10

1, 3
1, 4 n = 3 or 6

Linkers

R = Me, Et, *i*-Pr, *t*-Bu,
aryl, heteroaryl

O—(CH$_2$)$_m$—O
m = 2, 3, 4...

1, 3
1, 4 n = 3 or 6

Linkers

R = Me, Et, i-Pr, t-Bu,
aryl, heteroaryl 1, 3
1, 4

HN—(CH$_2$)$_m$—NH
m = 2, 3, 4...

TRIOXANE THIOACETAL MONOMERS AND DIMERS AND METHODS OF USE THEREOF

CROSS REFERENCE TO RELATED APPLICATIONS

This application is a 35 U.S.C. 0371 U.S. national phase entry of International Application No. PCT/US2013/028188 having an international filing date of Feb. 28, 2013, which claims the benefit of U.S. Provisional Application No. 61/604,032, filed Feb. 28, 2012, each of which is incorporated herein by reference in its entirety.

FEDERALLY SPONSORED RESEARCH OR DEVELOPMENT

This invention was made with government support under AI 34885 awarded by the National Institutes of Health. The government has certain rights in the invention.

BACKGROUND

Malaria is one of the world's most widespread infectious diseases. Ridley et al., 2002. Much effort is currently being devoted to develop effective vaccines to prevent humans from becoming infected with malaria parasites. LeBlanc et al., 2008; Troye-Blomberg et al., 2007. Treatment of humans afflicted with malaria with antimalarial amines, such as chloroquine, has been effective for over 50 years. Ridley et al., 2002. Malaria parasites, however, have developed widespread resistance to popular quinoline-based antimalarial drugs, including chloroquine. Olliaro et al., 2001. Such resistance seriously compromises the efficacy of chloroquine for treating people infected with malaria and has stimulated a search for new natural and synthetic antimalarial agents. Progress in chemotherapeutic methods of treating humans afflicted with malaria has been made using protease inhibitors to starve the parasites, Hof et al., 2006; Pandey et al., 2004; using antimalarial acridones, Kelly et al., 2009, and new 4-aminoquinolines, Yearick et al., 2008, to counteract resistance; and using some modified chloroquine analogs. Ramanathan-Girish et al., 2004. A new non-quinoline family of rapidly acting antimalarial peroxides was discovered in China during the early 1970s and has since become popular in treating malaria in humans. Begue and Bonnet-Delepon, 2007; Gelb, 2007; Haynes, 2006; Jefford, 2004; Klayman, 1985; O'Neill and Posner, 2004; Shizhen, 2003; Tang et al., 2004. The natural trioxane artemisinin and its semi-synthetic derivative trioxanes artemether and water-soluble sodium artesunate are now recommended by the World Health Organization (WHO) for use in combination with a classical antimalarial amine drug for reliable chemotherapy of humans infected with malaria. WHO, 2006.

This artemisinin combination therapy (ACT) is now widely used in areas of the world where malaria is endemic. Ashley and White, 2005; de Pilla Varotti et al., 2008; Adjuik et al., 2004; Guthmann et al., 2006; Myint et al., 2007; Sirima et al., 2009. Typically, current ACT requires a repeated dose regimen, which usually involves a total of three to six doses of a trioxane plus an amino antimalarial administered to a malaria-infected patient over several days. Sagara et al., 2008; Fanello et al., 2007. Patient compliance with adhering to such a repeated-dose regimen, however, is often a serious challenge. Souares et al., 2009. Patient compliance would be improved and cost lowered by a single dose oral cure. Therefore, a single-dose oral cure for malaria is highly desirable.

SUMMARY

The presently disclosed subject matter provides monomeric and dimeric trioxane thioacetals and methods of their use for treating subjects infected with malaria or other parasitic infectious diseases including, but not limited to, toxoplasmic infection; subjects afflicted with psychiatric conditions associated with toxoplasmic infection; and subjects afflicted with cancer.

In some aspects, a compound of Formula (I) is provided:

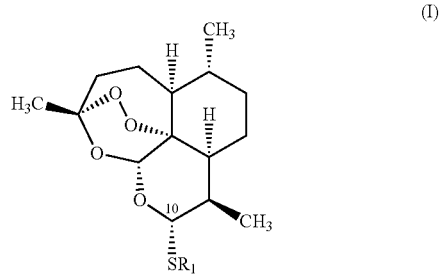

(I)

wherein:

$R_1$ is —$(CH_2)_n$—O—$R_{2a}$ or —$(CH_2)_{n-1}$—C(=O)—$R_{2b}$, wherein n is an integer from 2 to 11; and $R_{2a}$ is selected from the group consisting of H; —$CH_2C$≡$CH$; —$CH_2$—C(=$CH_2$)$R_3$, wherein $R_3$ is halogen; —$CH_2$—$R_4$, wherein $R_4$ is selected from the group consisting of:

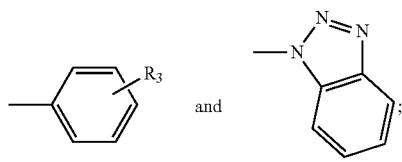

wherein $R_3$ is as defined above; and —(C=$X_1$)—$R_5$; wherein $X_1$ is O or S; and $R_5$ is selected from the group consisting of substituted or unsubstituted alkyl, alkoxyl, substituted or unsubstituted aryl, —$SR_6$, —$NR_6R_7$; wherein $R_6$ and $R_7$ are each selected from the group consisting of H, substituted or unsubstituted alkyl; and $R_{2b}$ is selected from the group consisting of hydroxyl; substituted or unsubstituted alkoxyl; substituted or unsubstituted aryloxyl; and —$NR_6R_7$, wherein $R_6$ and $R_7$ are as defined above; under the proviso that if $R_{2b}$ is hydroxyl, n cannot be 3;

or an enantiomer, diastereomer, racemate or pharmaceutically acceptable salt, prodrug, or solvate thereof.

In other aspects, a compound of Formula (II):

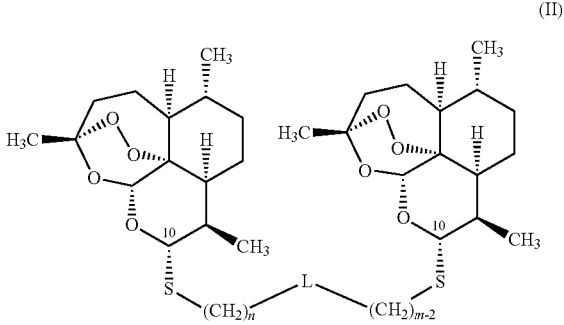

(II)

wherein m and n can be the same or different and are each independently an integer selected from 3 or 6; or an enantiomer, diastereomer, racemate or pharmaceutically acceptable salt, prodrug, or solvate thereof.

In yet other aspects, a compound of Formula (III) is provided:

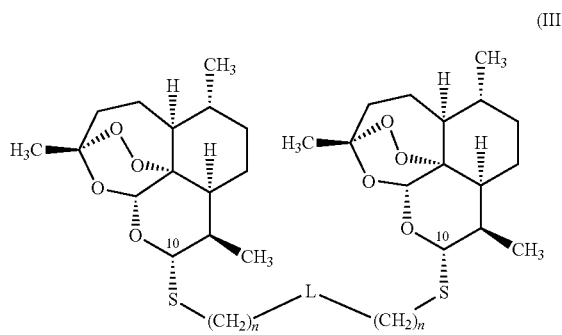

(III)

wherein each n is an integer independently selected from the group consisting of 3 and 6; L is a linking group selected from the group consisting of:

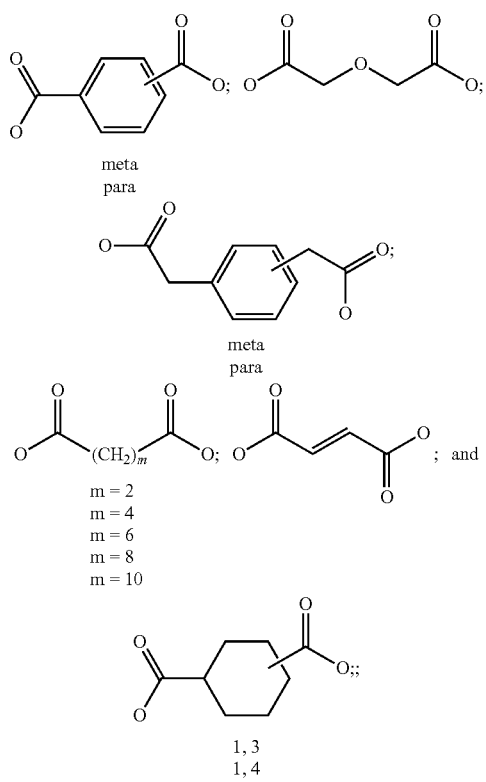

or an enantiomer, diastereomer, racemate or pharmaceutically acceptable salt, prodrug, or solvate thereof.

In other aspects, a compound of Formula (IV) is provided:

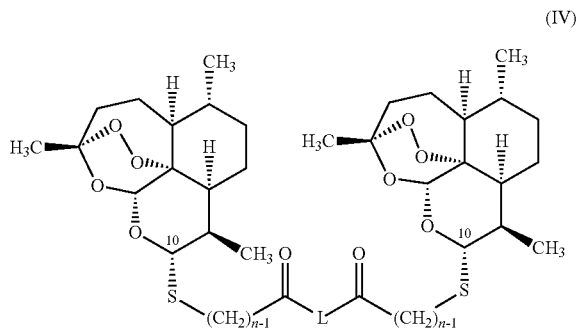

(IV)

wherein each n is an integer independently selected from the group consisting of 3 and 6; L is a linking group selected from the group consisting of:

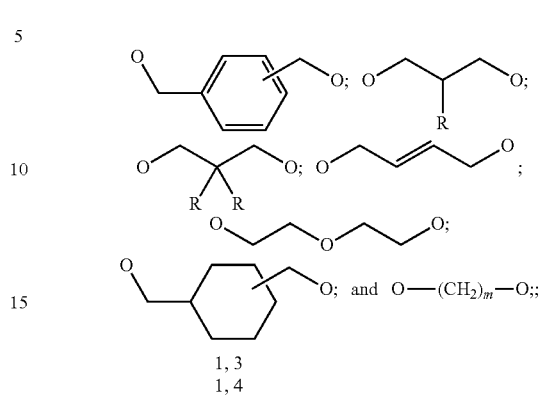

wherein m is an integer from 2 to 8; R is selected from the group consisting of alkyl, cycloalkyl, heteroalkyl, aryl, and heteroaryl, each of which can be substituted or unsubstituted; or an enantiomer, diastereomer, racemate or pharmaceutically acceptable salt, prodrug, or solvate thereof.

In yet other aspects, a compound of Formula (V) is provided:

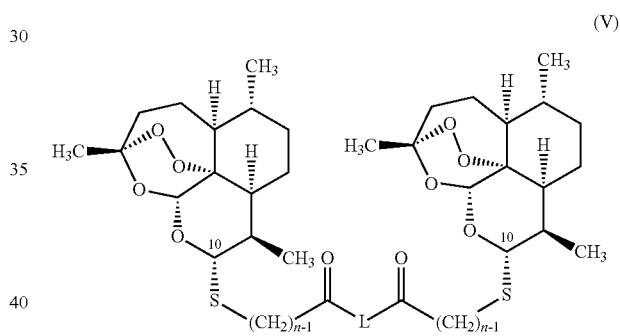

(V)

wherein each n is an integer independently selected from the group consisting of 3 and 6; L is a linking group selected from the group consisting of:

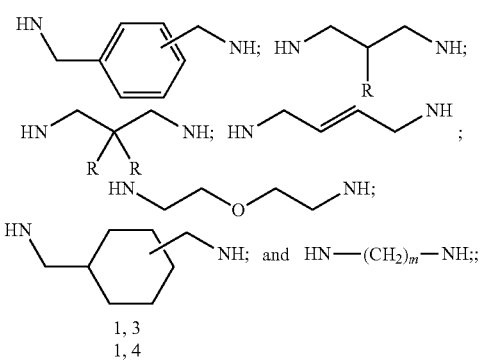

wherein m is an integer from 2 to 8; R is selected from the group consisting of alkyl, cycloalkyl, heteroalkyl, aryl, and heteroaryl, each of which can be substituted or unsubstituted; or an enantiomer, diastereomer, racemate or pharmaceutically acceptable salt, prodrug, or solvate thereof.

In certain aspects, the presently disclosed compounds of Formula (I-V) can be used for preventing, controlling or treating an infectious disease in a subject in need of treatment thereof.

In particular aspects, the infectious disease includes a parasitic disease selected from the group consisting of a plasmodia parasite infection, a *T. gondii* infection, a trypanosome parasite infection, and a *Cryptosporidium* parasite infection.

In other aspects, the method of treatment further comprises administering to the subject a quinoline anti-malarial drug including, but not limited to, chloroquine, quinine, mefloquine, and primaquine, and/or an antifolate, such as lumefantrine, concurrently or sequentially with a compound of Formula (I-V).

In other aspects, the presently disclosed subject matter provides a method of treating a psychiatric disorder associated with *toxoplasma* infection, such as schizophrenia, in a subject in need of treatment thereof, the method comprising administering to the subject a therapeutically-effective amount of a compound of Formula (I-V).

In yet other aspects, the method further comprises administering to the subject one or more antipsychotic drugs selected from the group consisting of chlorpromazine (THORAZINE®), haloperidol (HALDOL®), fluphenazine (PROLIXIN®), thiothixene (NA VANE®), trifluoperazine (STELAZINE®), perphenazine (TRILAFON®), and thioridazine (MELLARIL®), clozapine (CLOZARIL®), risperidone (RISPERDAL®), olanzapine (ZYPREXA®), quetiapine (SEROQUEL®), ziprasidone (GEODON®), and aripiprazole (ABILIFY®) concurrently or sequentially with the compound of Formula (I-V).

In further aspects, the presently disclosed subject matter provides a method for treating cancer, including, but not limited to, leukemia, non-small cell lung cancer, colon cancer, central nervous system cancer, melanoma cancer, ovarian cancer, renal cancer, prostate cancer, and breast cancer, in a subject in need of treatment thereof, the method comprising administering to the subject a therapeutically-effective amount of a compound of Formula (I-V).

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
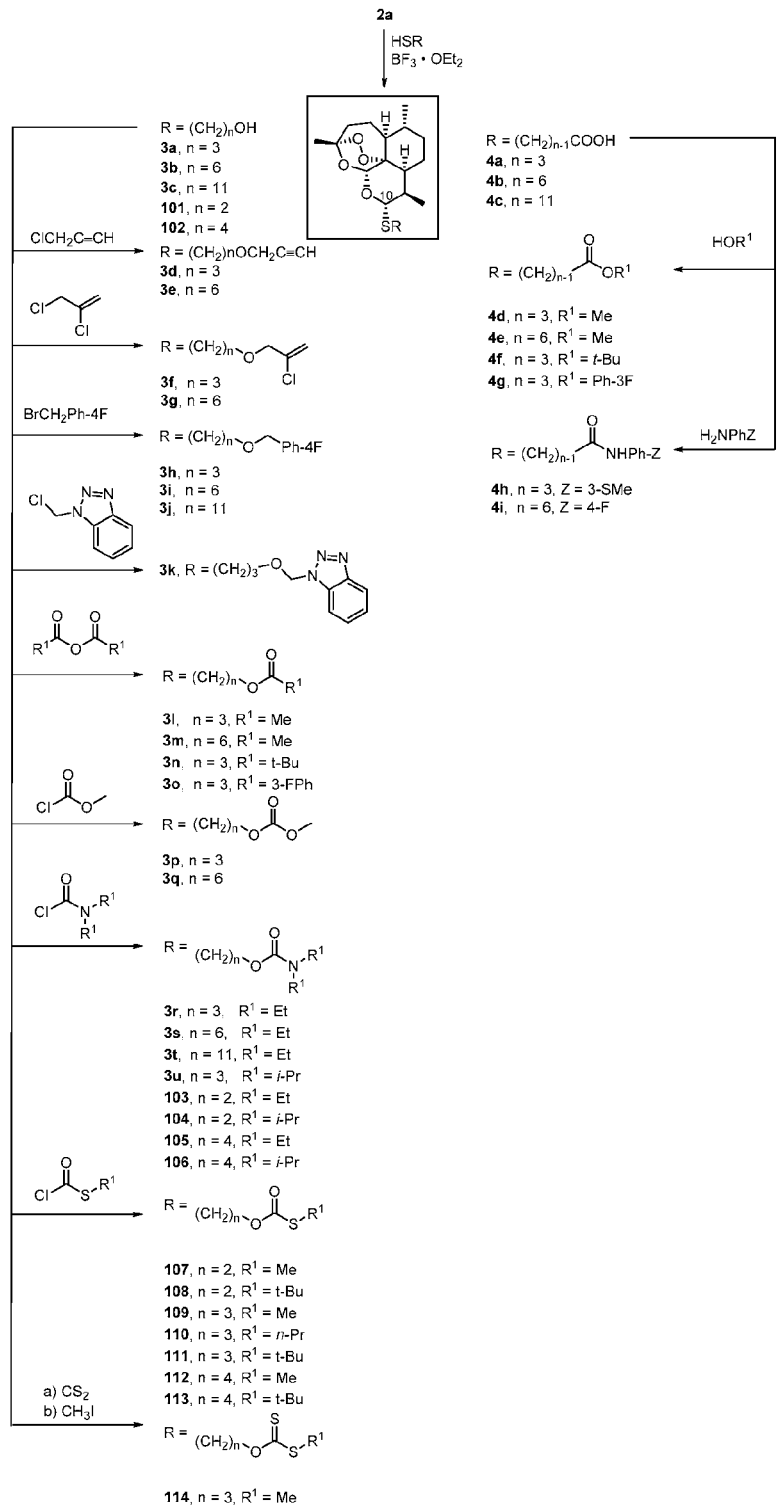
Figure 2:
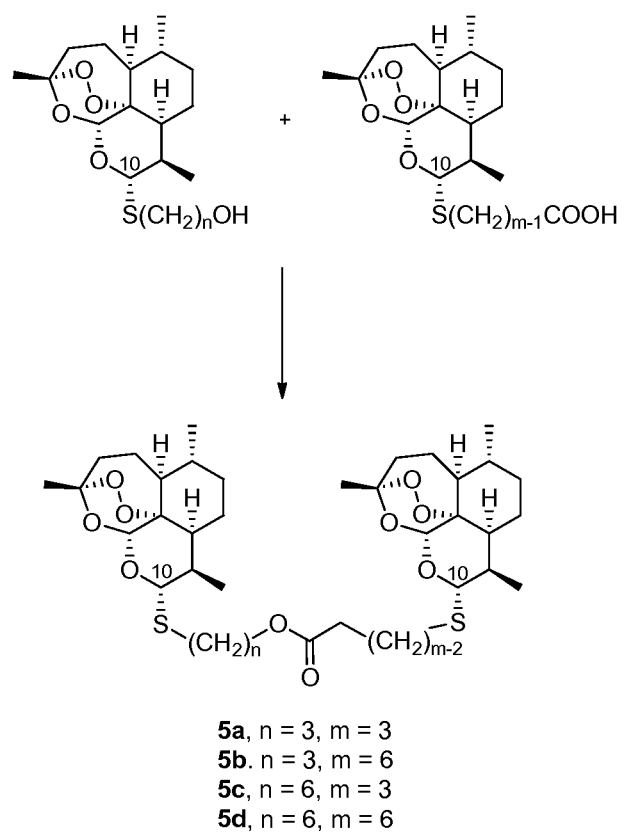
Figure 3:
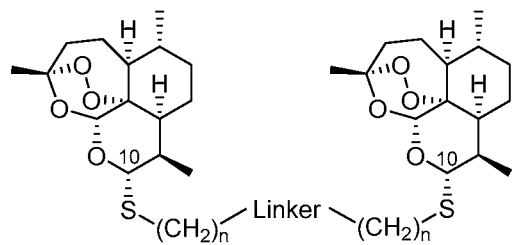
Figure 3:
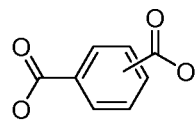
Figure 3:
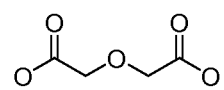
Figure 3:
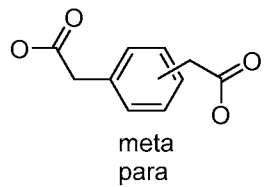
Figure 3:
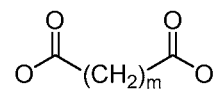
Figure 3:
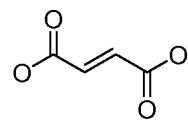
Figure 3:
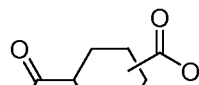
Figure 4:
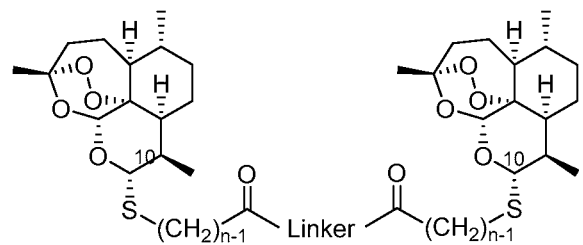
Figure 4:
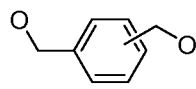
Figure 4:
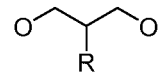
Figure 4:
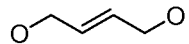
Figure 4:
Figure 4:
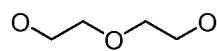
Figure 4:
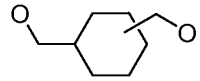
Figure 5:
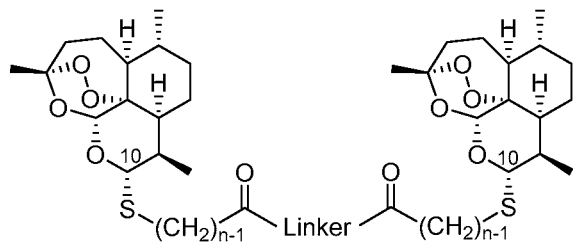
Figure 5:
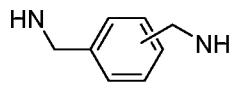
Figure 5:
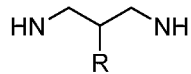
Figure 5:
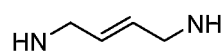
Figure 5:
Figure 5:
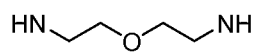
Figure 5:
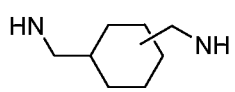
Figure 5:
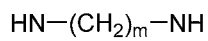

Having thus described the presently disclosed subject matter in general terms, reference will now be made to the accompanying Figures, which are not necessarily drawn to scale, and wherein:

FIG. 1 shows a general synthesis scheme for the preparation of alcohol derivatives and carboxylic acid derivatives of the presently disclosed trioxane thioacetal monomers of Formula (I);

FIG. 2 shows a general synthesis scheme for the preparation of the presently disclosed trioxane dimer thioacetal esters of Formula (II);

FIG. 3 shows a generic Formula (III) and representative symmetrical bis-ester thioacetal dimers with dicarboxylic acid linker;

FIG. 4 shows a generic Formula (IV) and representative symmetrical bis-ester thioacetal dimers with diol linker; and FIG. 5 shows a generic Formula (V) and representative symmetrical bis-amide thioacetal dimers with a diamine linker.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

As provided in more detail immediately herein below, the presently disclosed subject matter provides monomeric and dimeric trioxane thioacetals and methods of their use for treating subjects infected with malaria or other parasitic infectious diseases including, but not limited to, toxoplasmic infection; subjects afflicted with psychiatric conditions associated with toxoplasmic infection; and subjects afflicted with cancer.

I. Trioxane Thioacetal Derivatives of Artemisinin

Over the years, malaria parasites have grown resistant toward several common antimalarial drugs. Plowe, 2005. Due to this drug resistance, the World Health Organization (WHO) has recommended that researchers change their approach toward fighting this disease, which affected over 216 million people in 2010. *Guidelines for the Treatment of Malaria*, 2010; *World Malaria Report* 2011.

This current approach, known as Artemisinin Combination Therapy (ACT), uses the natural trioxane artemisinin (1) or one of its derivatives 2a-2c as one component as well as a traditional alkaloid such as chloroquine as the second component. The endoperoxide unit of artemisinin is crucial for its antimalarial activity. Klayman, 1985.

Scheme 1. Artemisinin and derivatives thereof (prior art).

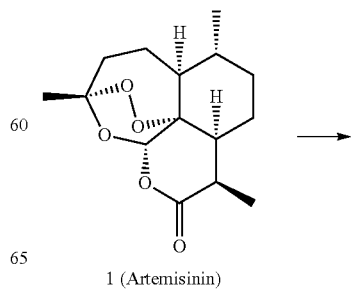

1 (Artemisinin)

-continued

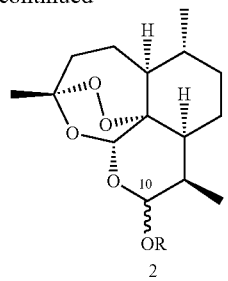

2a, R=H
2b, R = CH₃ (β)
2c, R = C(O)CH₂CH₂COONa (α)
2d, R = C(O)CH₃ (α)

Since artemisinin (1) has proven to be efficient in killing *Plasmodium* parasites, but has limited bioavailability, semi-synthetic analogs have been studied. Researchers have developed several effective drugs by modifying artemisinin. Some C-10 artemisinin-derived trioxane thioacetals have been reported. Several of these thioacetals are aryl sulfides, Venugopalan, et al., 1995; Oh, et al., 2003; Lee, et al., 2005, while others are alkyl sulfides. Venugopalan, et al., 1995. Although some of the reported trioxane alkyl sulfides have free alcohol or carboxylic acid functional groups, only a very few alcohol or carboxylate derivatives have been reported. Venugopalan, et al., 1995.

A. Compounds of Formula (I-V)

Since several of the previously prepared thioacetal alcohols and carboxylic acids are potent antimalarials when administered to mice in multiple doses, Venugopalan, et al., 1995, a small library of thioacetal alcohol derivatives and thioacetal carboxylic acid derivatives (FIG. 1) were prepared to probe SAR in order to optimize in vivo antimalarial efficacy, with the goal of a single low dose oral cure. Some of the presently disclosed thioacetal esters, carbonates, amides, and carbamates may be prodrugs in vivo, undergoing enzymatic (e.g. esterase, peptidase) hydrolysis into their parent alcohol or carboxylic acid.

Accordingly, in some embodiments, the presently disclosed subject matter provides a compound of Formula (I):

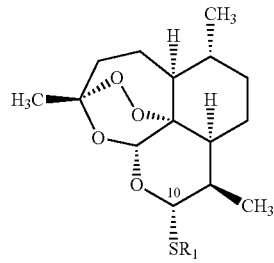

(I)

wherein:

$R_1$ is —(CH₂)$_n$—O—$R_{2a}$ or —(CH₂)$_{n-1}$—C(=O)—$R_{2b}$, wherein n is an integer from 2 to 11; and $R_{2a}$ is selected from the group consisting of H; —CH₂C≡CH; —CH₂—C(=CH₂)$R_3$, wherein $R_3$ is halogen; —CH₂—$R_4$, wherein $R_4$ is selected from the group consisting of:

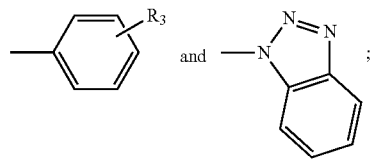

wherein $R_3$ is as defined above; and —(C=$X_1$)—$R_5$; wherein $X_1$ is O or S; and $R_5$ is selected from the group consisting of substituted or unsubstituted alkyl, alkoxyl, substituted or unsubstituted aryl, —S$R_6$, —N$R_6R_7$; wherein $R_6$ and $R_7$ are each selected from the group consisting of H, substituted or unsubstituted alkyl; and $R_{2b}$ is selected from the group consisting of hydroxyl; substituted or unsubstituted alkoxyl; substituted or unsubstituted aryloxyl; and —N$R_6R_7$, wherein $R_6$ and $R_7$ are as defined above; under the proviso that if $R_{2b}$ is hydroxyl, n cannot be 3;

or an enantiomer, diastereomer, racemate or pharmaceutically acceptable salt, prodrug, or solvate thereof.

In some embodiments of the compound of Formula (I), $R_1$ is —(CH₂)$_n$—O—$R_{2a}$ and $R_{2a}$ is selected from the group consisting of H; OH, —CH₂C≡CH; —CH₂—C(=CH₂)Cl; —(C=O)—CH₃; —(C=O)—C(CH₃)₃; —(C=O)—N(CH₂CH₃)₂; —(C=O)—N(CH(CH₃)₂)₂; —(C=O)—S—CH₃; —(C=O)—S—CH₂CH₂CH₃; —(C=O)—S—C(CH₃)₃; —(C=S)—S—CH₃; —(C=O)-(halogenated phenyl); —(C=O)—O$R_8$, wherein $R_8$ is selected from the group consisting of substituted or unsubstituted alkyl, substituted or unsubstituted alkenyl, substituted or unsubstituted alkynyl, and substituted or unsubstituted aryl;

In particular embodiments of the compound of Formula (I), the compound is selected from the group consisting of:

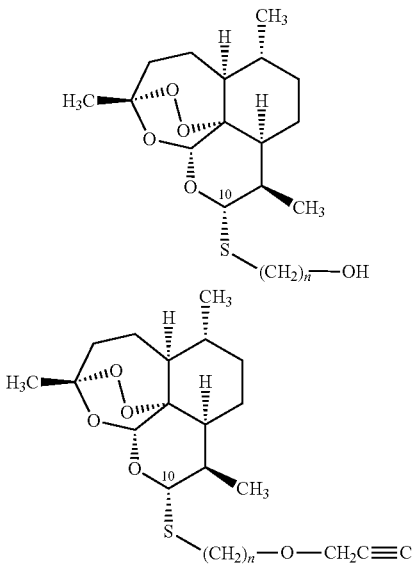

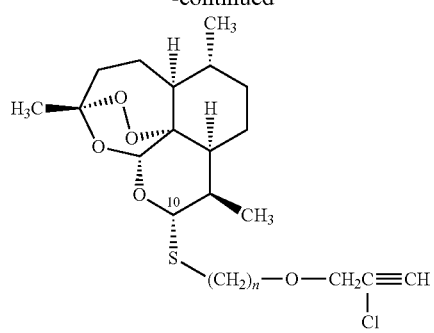
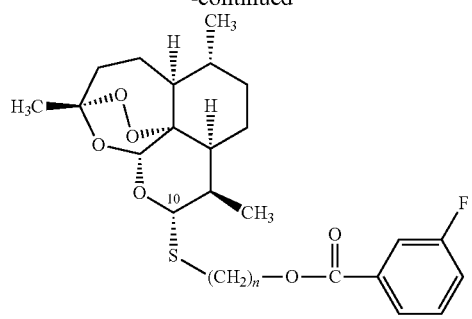
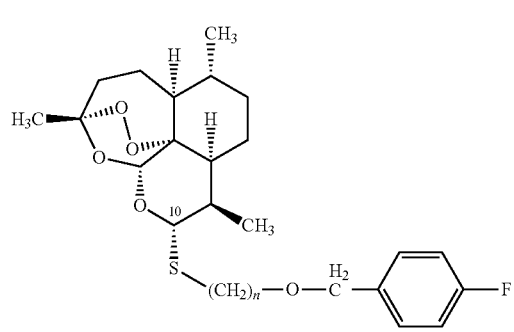
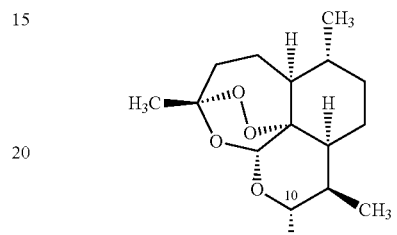
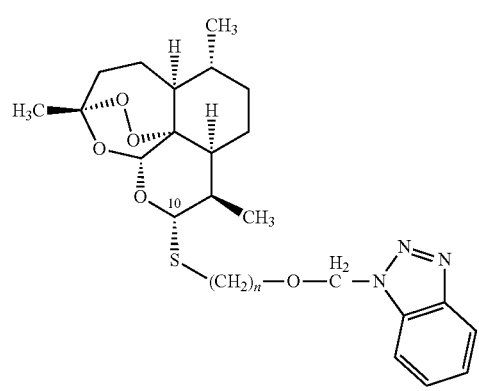
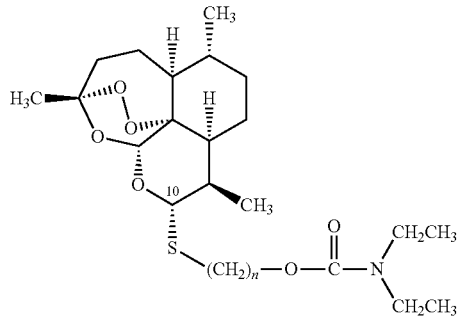
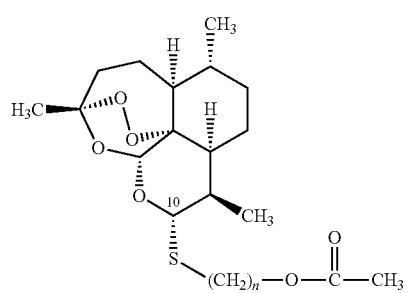
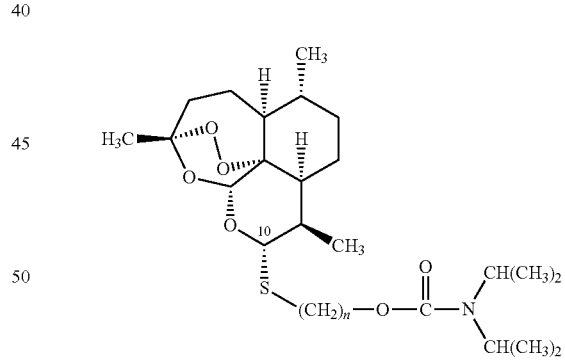
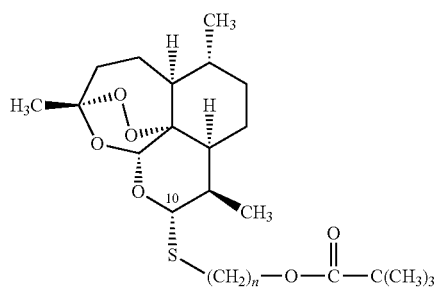
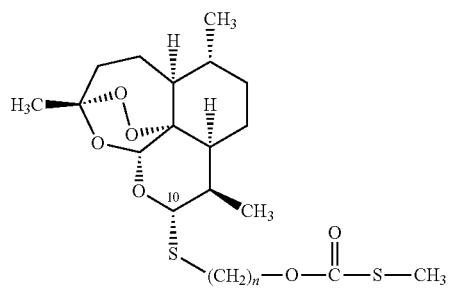

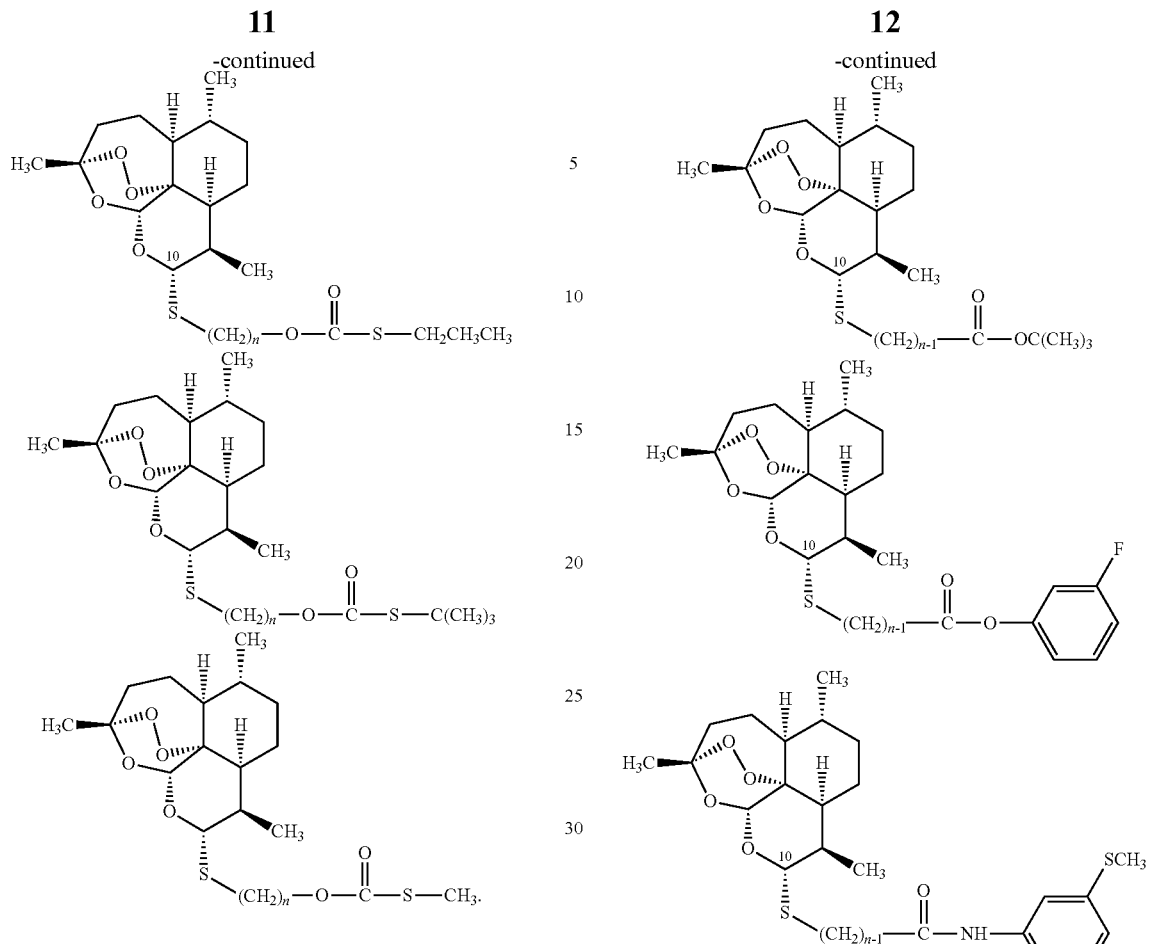

In some embodiments of a compound of Formula (I), $R_1$ is —$(CH_2)_{n-1}$—C(=O)—$R_{2b}$ and $R_{2b}$ is selected from the group consisting of hydroxyl; methoxyl; t-butoxyl; 3-fluorophenoxyl; and —$NR_6R_7$, wherein $R_6$ is H and $R_7$ is selected from the group consisting of 4-fluorophenyl and 3-($SCH_3$)-phenyl.

In particular embodiments, the compound of Formula (I) is selected from the group consisting of:

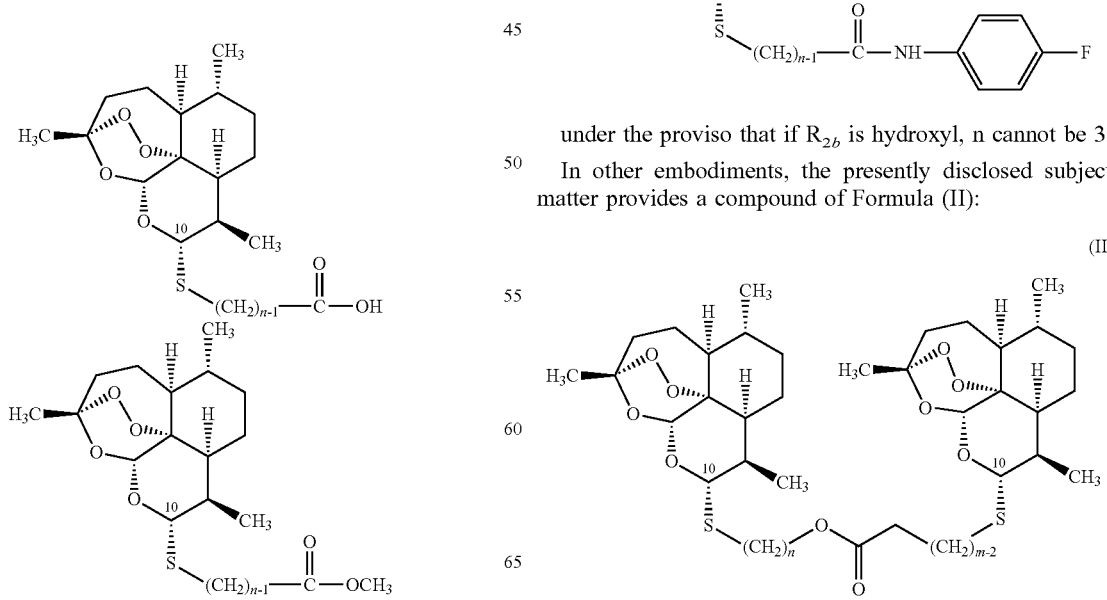

under the proviso that if $R_{2b}$ is hydroxyl, n cannot be 3.

In other embodiments, the presently disclosed subject matter provides a compound of Formula (II):

(II)

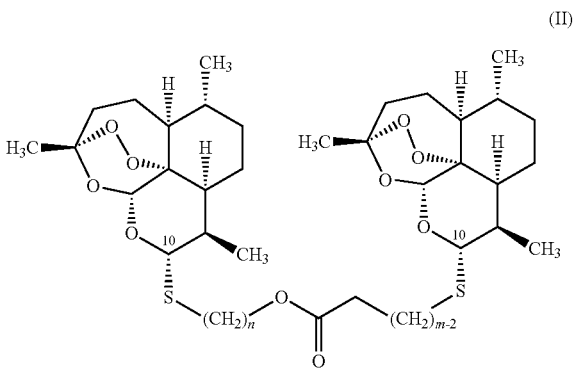

wherein m and n can be the same or different and are each independently an integer selected from 3 or 6; or an enantiomer, diastereomer, racemate or pharmaceutically acceptable salt, prodrug, or solvate thereof.

In yet other embodiments, the presently disclosed subject matter provides a compound of Formula (III):

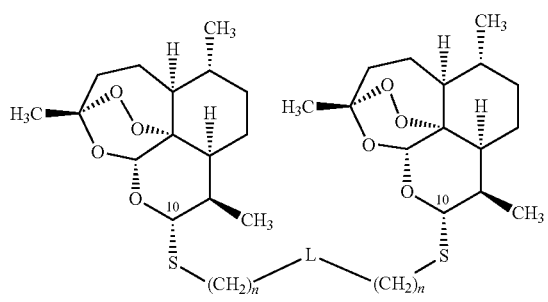

(III)

wherein each n is an integer independently selected from the group consisting of 3 and 6; L is a linking group selected from the group consisting of:

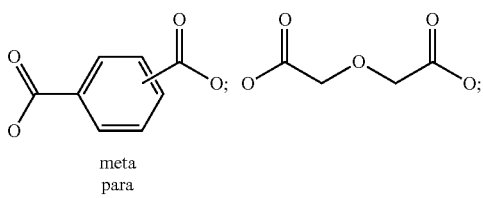

meta
para

meta
para

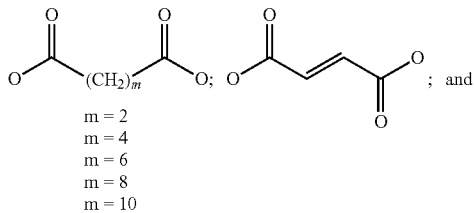

m = 2
m = 4
m = 6
m = 8
m = 10 and

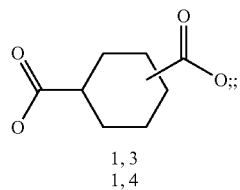

1, 3
1, 4 or an enantiomer, diastereomer, racemate or pharmaceutically acceptable salt, prodrug, or solvate thereof.

In yet other embodiments, the presently disclosed subject matter provides a compound of Formula (IV):

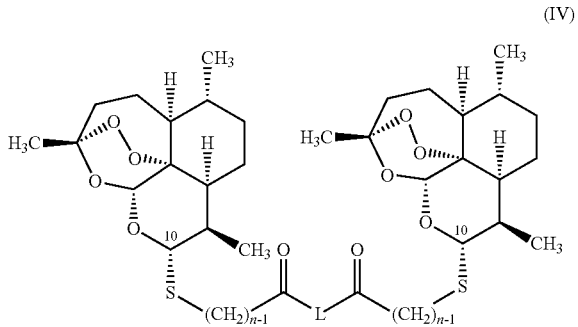

(IV)

wherein each n is an integer independently selected from the group consisting of 3 and 6; L is a linking group selected from the group consisting of:

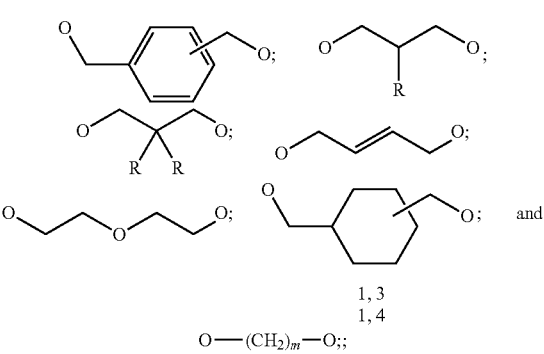

1, 3
1, 4

O—(CH$_2$)$_m$—O;;

wherein m is an integer from 2 to 8; R is selected from the group consisting of alkyl, cycloalkyl, heteroalkyl, aryl, and heteroaryl, each of which can be substituted or unsubstituted; or an enantiomer, diastereomer, racemate or pharmaceutically acceptable salt, prodrug, or solvate thereof.

In further embodiments, the presently disclosed subject matter provides a compound of Formula (V):

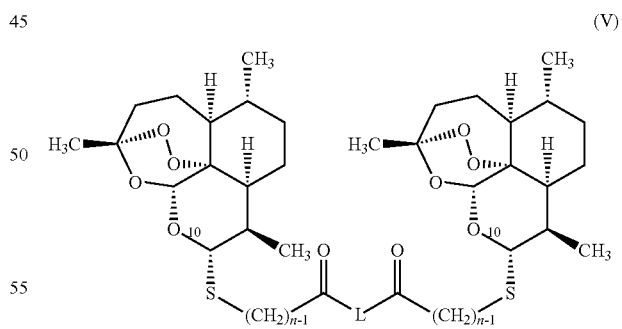

(V)

wherein each n is an integer independently selected from the group consisting of 3 and 6; L is a linking group selected from the group consisting of:

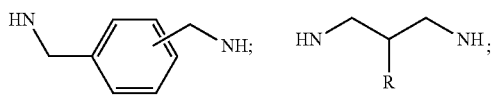

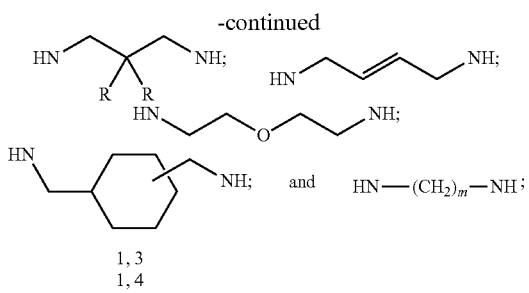

wherein m is an integer from 2 to 8; R is selected from the group consisting of alkyl, cycloalkyl, heteroalkyl, aryl, and heteroaryl, each of which can be substituted or unsubstituted; or an enantiomer, diastereomer, racemate or pharmaceutically acceptable salt, prodrug, or solvate thereof.

B. Methods of Treatment

In some embodiments, the presently disclosed monomeric and dimeric trioxane thioacetals of Formula (I-V) can be used for treating subjects infected with malaria or other parasitic infectious diseases including, but not limited to, toxoplasmic infection; subjects afflicted with psychiatric conditions associated with toxoplasmic infection; and subjects afflicted with cancer.

1. Methods of Treating a Subject Infected with Malaria

Each year approximately 200-300 million people experience a malarial illness and over 1 million individuals die. In patients with severe and complicated disease, the mortality rate is between 20 and 50%. *Plasmodium* is the genus of protozoan parasites that is responsible for all cases of human malaria and *Plasmodium falciparum* is the species of parasite that is responsible for the vast majority of fatal malaria infections. Malaria has traditionally been treated with quinolines, such as chloroquine, quinine, mefloquine, and primaquine, and with antifolates, such as sulfadoxine-pyrimethamine Unfortunately, most *P. falciparum* strains have now become resistant to chloroquine, and some, such as those in Southeast Asia, also have developed resistance to mefloquine and halofantrine; multidrug resistance also is developing in Africa.

The endoperoxides are a promising class of antimalarial drugs that may meet the dual challenges posed by drug-resistant parasites and the rapid progression of malarial illness. As discussed hereinabove, the first generation endoperoxides include natural artemisinin and several synthetic derivatives. Artemisinin has been used successfully to treat malaria patients throughout the world, including those infected with both chloroquine-sensitive and chloroquine-resistant strains of *P. falciparum*. Although artemisinin is effective at suppressing the parasitemias of *P. vivax* and *P. falciparum*, the problems encountered with recrudescence, and the compound's insolubility in water, led scientists to modify artemisinin chemically, a difficult task because of the chemical reactivity of the peroxide linkage, which is believed to be an essential moiety for antimalarial activity. In some embodiments, the presently disclosed subject matter provides a new series of monomeric and dimeric trioxane thioacetals useful for treating subjects infected with malaria.

Accordingly, the presently disclosed subject matter provides a method of treating a subject infected with malaria, the method comprising administering to a subject in need of treatment thereof, a compound of Formula (I-V) as disclosed herein. In some embodiments, the method further comprises administering to the subject a quinoline anti-malarial drug or an antifolate concurrently or sequentially with a compound of Formula (I-V). In particular embodiments, the quinoline anti-malarial drug is selected from the group consisting of chloroquine, quinine, mefloquine, and primaquine. In more particular embodiments, the anti-malarial drug is mefloquine. In some embodiments, the antifolate is lumefantrine.

2. Methods of Treating Other Parasitic Infectious Diseases

In some embodiments, the presently disclosed monomeric and dimeric trioxane thioacetals are useful for preventing, treating and controlling infections, including but not limited to toxoplasmic infection, and psychiatric conditions associated with toxoplasmic infection. *Toxoplasma gondii* (*T. gondii*) is an apicomplexan protozoan of world-wide medical importance. Humans are infected by *T. gondii* through contact with feces from infected cats, by the consumption of undercooked meat from infected animals, or by transmission from infected mother to fetus. This parasite can cause systemic infection and widespread organ damage in immunocompromised individuals and neonates. Infection of immunocompetent adults can result in fever and adenopathy. Tenter et al., 2000. Serological studies indicate that *T. gondii* could be associated with chronic neuropsychiatric diseases or behavioral abnormalities in some populations. Bachmann et al., 2005; Yolken et al., 2001.

Available medications for the prevention and treatment of *toxoplasma* infection show limited efficacy and have substantial side effects. Georgiev 1994. Published studies have indicated that the naturally occurring 1,2,4-trioxane artemisinin and artemisinin derivatives, such as artemether, originally developed for the treatment of malaria, have the ability to inhibit *toxoplasma* replication in vitro. Berens et al., 1998; Chang et al., 1989; Holfels et al., 1994; Ou-Yang et al., 1990. While these trioxanes have a number of advantages in terms of rapid action and low levels of toxicity, they are limited in terms of absorption, bioavailability, and short half-life (i.e., easy hydrolysis into toxic dihydroartemisinin) Lin et al., 1987; O'Neill and Posner, 2004. Thus, what is needed are improved derivatives of artemisinin having not only rapid action and low levels of toxicity, but also better absorption, bioavailability, and longer half-lives for inhibiting the replication of *T. gondii*.

Selected derivatives of artemisinin exhibiting in vitro efficacy against *T. gondii* are disclosed in published PCT patent application no. WO2008/127381 to Brando et al., which is incorporated herein by reference in its entirety. The artemisinin derivatives disclosed in WO2008/127381 also have been shown to inhibit the replication of chloroquine-sensitive *Plasmodium falciparum*. Accordingly, in some embodiments, the presently disclosed subject matter provides methods of using the presently disclosed monomeric and dimeric trioxane thioacetals and compositions for preventing, controlling or treating infectious diseases, including but not limited to, parasitic infectious diseases, such as *T. gondii* infection, trypanosome parasite infection, plasmodia parasite infection, and *Cryptosporidium* parasite infection.

Further, the evidence linking infection with *T. gondii* to the etiology of schizophrenia is well known. Torrey et al., 2007. Epidemiologic studies have indicated that infectious agents may contribute to some cases of schizophrenia. In animals, infection with *T. gondii* can alter behavior and neurotransmitter function. In humans, acute infection with *T. gondii* can produce psychotic symptoms similar to those displayed by persons with schizophrenia. Since 1953, a total of 19 studies of *T. gondii* antibodies in persons with schizophrenia and other severe psychiatric disorders and in controls have been reported; 18 reported a higher percentage of antibodies in the affected persons; in 11 studies the difference was statistically significant. Two other studies found that exposure to cats in childhood was a risk factor for the development of schizophrenia. Some medications used to treat schizophrenia inhibit the replication of *T. gondii* in cell culture. Jones-Brando et al., 2003. Establishing the role of *T. gondii* in the etiopathogenesis of schizophrenia may lead to new medications for its prevention and treatment.

Schizophrenia is a pervasive neuropsychiatric disease of uncertain cause that affects approximately 1% of the adult population in the United States and Europe. An increased occurrence of schizophrenia in family members of affected persons suggests that genetic factors play a role in its etiology, and some candidate predisposing genes have been identified. Environmental factors also are important. Epidemiologic studies, for example, have established that winter-spring birth, urban birth, and perinatal and postnatal infection are all risk factors for the disease developing in later life. These studies have rekindled an interest in the role of infectious agents in schizophrenia, a concept first proposed in 1896.

*T. gondii* is an intracellular parasite in the phylum Apicomplexa. Its life cycle can be completed only in cats and other fields, which are the definitive hosts. *T. gondii*, however, also infects a wide variety of intermediate hosts, including humans. In many mammals, *T. gondii* is known to be an important cause of abortions and stillbirths and to selectively infect muscle and brain tissue. A variety of neurologic symptoms, including incoordination, tremors, head-shaking, and seizures, has been described in sheep, pigs, cattle, rabbits, and monkeys infected with *T. gondii*. Humans may become infected by contact with cat feces or by eating undercooked meat.

The importance of these modes of transmission may vary in different populations. Individual response to *Toxoplasma* infection is determined by immune status, timing of infection, and the genetic composition of the host and the organism. *Toxoplasma* organisms have also been shown to impair learning and memory in mice and to produce behavioral changes in both mice and rats. Of special interest are studies showing that *Toxoplasma*-infected rats become less neophobic, leading to the diminution of their natural aversion to the odor of cats. These behavioral changes increase the chances that the rat will be eaten by a cat, thus enabling *Toxoplasma* to complete its life cycle, an example of evolutionarily driven manipulation of host behavior by the parasite.

In humans, *toxoplasma* is an important cause of abortions and stillbirths after primary infection in pregnant women. The organism also can cross the placenta and infect the fetus. The symptoms of congenital toxoplasmosis include abnormal changes in head size (hydrocephaly or microcephaly), intracranial calcifications, deafness, seizures, cerebral palsy, damage to the retina, and mental retardation. Some sequelae of congenital toxoplasmosis are not apparent at birth and may not become apparent until the second or third decade of life. Hydrocephalus, increased ventricular size, and cognitive impairment also have been noted in some persons with schizophrenia and other forms of psychosis.

Some cases of acute toxoplasmosis in adults are associated with psychiatric symptoms, such as delusions and hallucinations. Schizophrenia was first diagnosed in these patients, but later neurologic symptoms developed, which led to the correct diagnosis of *Toxoplasma* encephalitis.

Chlorpromazine (THORAZINE®) is the first antipsychotic medication used for schizophrenia, which was soon followed by other medications, such as haloperidol (HALDOL®), fluphenazine (PROLIXIN®), thiothixene (NAVANE®), trifluoperazine (STELAZINE®), perphenazine (TRILAFON®), and thioridazine (MELLARIL®). These medications have become known as "neuroleptics" because, although effective in treating positive symptoms (i.e., acute symptoms such as hallucinations, delusions, thought disorder, loose associations, ambivalence, or emotional lability), cause side effects, many of which affect the neurologic (nervous) system.

A new class of antipsychotics (atypical antipsychotics) was introduced after 1989. At clinically effective doses, no (or very few) of these neurological side effects, which often affect the extrapyramidal nerve tracts (which control such things as muscular rigidity, painful spasms, restlessness, or tremors) are observed. The first of the new class, clozapine (CLOZARIL®) is the only agent that has been shown to be effective where other antipsychotics have failed. Its use is not associated with extrapyramidal side effects, but it does produce other side effects, including possible decrease in the number of white cells, so the blood needs to be monitored every week during the first 6 months of treatment and then every 2 weeks to catch this side effect early if it occurs. Other atypical antipsychotics include risperidone (RISPERDAL®), olanzapine (ZYPREXA®), quetiapine (SEROQUEL®), ziprasidone (GEODON®), and aripiprazole (ABILITY®). The use of these medications has allowed successful treatment and release back to their homes and the community for many people suffering from schizophrenia.

Accordingly, in some embodiments, the presently disclosed subject matter provides a method for treating psychiatric disorders associated with *toxoplasma* infection including, but not limited to, schizophrenia, using the presently disclosed monomeric and dimeric trioxane thioacetals of Formula (I-V) and compositions thereof alone or in combination with one or more antipsychotic drugs including, but not limited to, chlorpromazine (THORAZINE®), haloperidol (HALDOL®), fluphenazine (PROLIXIN®), thiothixene (NAVANE®), trifluoperazine (STELAZINE®), perphenazine (TRILAFON®), and thioridazine (MELLARIL®), clozapine (CLOZARIL®), risperidone (RISPERDAL®), olanzapine (ZYPREXA®), quetiapine (SEROQUEL®), ziprasidone (GEODON®), and aripiprazole (ABILIFY®).

3. Methods of Treating Cancer

Since the isolation of artemisinin, there has been a concerted effort by investigators to study other therapeutic applications of artemisinin and its derivatives. The National Institutes of Health reported that artemisinin is inactive against P388 leukemia (NCI Report on NSC 369397, tested on 25 Oct. 1983). Later anticancer studies that have been conducted on cell line panels consisting of 60 lines organized into nine, disease-related subpanels including leukemia, non-small-cell lung cancer, colon, CNS, melanoma, ovarian, renal, prostate and breast cancers, further confirm that artemisinin displays modest anticancer activity.

While artemisinin and its related derivatives demonstrate zero to slight antiproliferative and antitumor activity, it has been discovered that a class of artemisinin dimer compounds exhibits antiproliferative and antitumor activities that are, in vitro, equivalent to or greater than known antiproliferative and antitumor agents (U.S. Pat. No. 5,677,468 also incorporated herein by reference in its entirety for all purposes). Unfortunately, while the in vitro results of these artemisinin compounds are encouraging, these compounds do not appear to have as significant antitumor activity on the treatment of tumor cells in mice. There is still a need, therefore, to develop stable artemisinin derivatives and structural analogs thereof having antimalarial, anticancer, antiproliferative, and antitumor activities that are equivalent to or greater than those of known antimalarial, anticancer, antiproliferative and antitumor agents, respectively.

For example, selected artemisinin-related dimers, e.g., trioxane dimer sulfur compounds, having anticancer activity have been disclosed in international PCT patent application publication no. WO2010/009428, to Posner and Rosenthal, which is incorporated herein by reference in its entirety. Other artemisinin analogs, including trioxane dimers have been shown to exhibit anti-cancer activity. See, e.g., U.S. patent application publication nos. US2009/0291923, to Posner et al., published Nov. 26, 2009; US2006/0142377 to Posner et al., published Jun. 29, 2006; and US2002/0055528 to Posner et al., published May 9, 2002, each of which is incorporated herein by reference in its entirety.

Accordingly, in some embodiments, the presently disclosed subject matter provides a method for treating cancer in a subject in need of such treatment, by administering to the subject a therapeutically effective amount of the presently disclosed monomeric and dimeric trioxane thioacetals of Formula (I-V). The cancer can include leukemia, non-small cell lung cancer, colon cancer, central nervous system cancer, melanoma cancer, ovarian cancer, renal cancer, prostate cancer, and breast cancer.

As used herein, the term "inhibit" or "inhibits" means to decrease, suppress, attenuate, diminish, arrest, or stabilize the development or progression of a disease, disorder, or condition, or the activity of a biological pathway, e.g., by at least 10%, 20%, 30%, 40%, 50%, 60%, 70%, 80%, 90%, 95%, 98%, 99%, or even 100% compared to an untreated control subject, cell, or biological pathway. By the term "decrease" is meant to inhibit, suppress, attenuate, diminish, arrest, or stabilize a symptom of a disease, disorder, or condition. It will be appreciated that, although not precluded, treating a disease, disorder or condition does not require that the disease, disorder, condition or symptoms associated therewith be completely eliminated.

As used herein, the terms "treat," treating," "treatment," and the like, are meant to decrease, suppress, attenuate, diminish, arrest, the underlying cause of a disease, disorder, or condition, or to stabilize the development or progression of a disease, disorder, condition, and/or symptoms associated therewith. The terms "treat," "treating," "treatment," and the like, as used herein can refer to curative therapy, prophylactic therapy, and preventative therapy. The treatment, administration, or therapy can be consecutive or intermittent. Consecutive treatment, administration, or therapy refers to treatment on at least a daily basis without interruption in treatment by one or more days. Intermittent treatment or administration, or treatment or administration in an intermittent fashion, refers to treatment that is not consecutive, but rather cyclic in nature. Treatment according to the presently disclosed methods can result in complete relief or cure from a disease, disorder, or condition, or partial amelioration of one or more symptoms of the disease, disease, or condition, and can be temporary or permanent. The term "treatment" also is intended to encompass prophylaxis, therapy and cure.

As used herein, the terms "prevent," "preventing," "prevention," "prophylactic treatment" and the like refer to reducing the probability of developing a disease, disorder, or condition in a subject, who does not have, but is at risk of or susceptible to developing a disease, disorder, or condition. Thus, in some embodiments, an agent can be administered prophylactically to prevent the onset of a disease, disorder, or condition, or to prevent the recurrence of a disease, disorder, or condition.

By "agent" is meant a compound of Formula (I-V) or another agent, e.g., another small molecule compound administered in combination with a compound of Formula (I-V). More generally, the term "therapeutic agent" means a substance that has the potential of affecting the function of an organism. Such an agent may be, for example, a naturally occurring, semi-synthetic, or synthetic agent. For example, the therapeutic agent may be a drug that targets a specific function of an organism. A therapeutic agent also may be a nutrient. A therapeutic agent may decrease, suppress, attenuate, diminish, arrest, or stabilize the development or progression of disease, disorder, or condition in a host organism.

The term "administering" as used herein refers to administering a compound of Formula (I-V) to a subject in need of treatment, as well as introducing the presently disclosed compounds into a medium in which a target microorganism is cultured.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing disease, disorder, condition or the prophylactic treatment for preventing the onset of a disease, disorder, or condition or an animal subject for medical, veterinary purposes, or developmental purposes. Suitable animal subjects include mammals including, but not limited to, primates, e.g., humans, monkeys, apes, gibbons, chimpanzees, orangutans, macaques and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, guinea pigs, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a disease, disorder, or condition. Thus, the terms "subject" and "patient" are used interchangeably herein. Subjects also include animal disease models (e.g., rats or mice used in experiments, and the like).

C. Pharmaceutical Compositions

The presently disclosed pharmaceutical compositions and formulations include pharmaceutical compositions of compounds of Formula (I-V), alone or in combination with one or more additional therapeutic agents, in admixture with a physiologically compatible carrier, which can be administered to a subject, for example, a human subject, for therapeutic or prophylactic treatment. As used herein, "physiologically compatible carrier" refers to a physiologically acceptable diluent including, but not limited to water, phosphate buffered saline, or saline, and, in some embodiments, can include an adjuvant. Acceptable carriers, excipients, or stabilizers are nontoxic to recipients at the dosages and concentrations employed, and can include buffers such as phosphate, citrate, and other organic acids; antioxidants including ascorbic acid, BHA, and BHT; low molecular weight (less than about 10 residues) polypeptides; proteins, such as serum albumin, gelatin or immunoglobulins; hydrophilic polymers, such as polyvinylpyrrolidone, amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counter-ions such as sodium; and/or nonionic surfactants such as Tween, Pluronics, or PEG. Adjuvants suitable for use with the presently disclosed compositions include adjuvants known in the art including, but not limited to, incomplete Freund's adjuvant, aluminum phosphate, aluminum hydroxide, and alum.

Compositions to be used for in vivo administration must be sterile, which can be achieved by filtration through sterile filtration membranes, prior to or following lyophilization and reconstitution. Therapeutic compositions may be placed into a container having a sterile access port, for example, an intravenous solution bag or vial having a stopper pierceable by a hypodermic injection needle.

One of skill in the art will recognize that the pharmaceutical compositions include the pharmaceutically acceptable salts of the compounds described above. The term "pharmaceutically acceptable salts" is meant to include salts of active compounds, which are prepared with relatively non-toxic acids or bases, depending on the particular substituent moieties found on the compounds described herein.

When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include alkali or alkaline earth metal salts including, but not limited to, sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids including, but not limited to, hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids, such as acetic (acetates), propionic (propionates), isobutyric (isobutyrates), maleic (maleates), malonic, benzoic (benzoates), succinic (succinates), suberic, fumaric (fumarates), lactic (lactates), mandelic (mandelates), phthalic (phthalates), benzenesulfonic (benzosulfonates), p-tolylsulfonic, citric (citrates), tartaric (tartrates, e.g., (+)-tartrates, (−)-tartrates or mixtures thereof including racemic mixtures), methanesulfonic, and the like. Other pharmaceutically acceptable salts, include, but are not limited to, besylate, bicarbonate, bitartrate, bromide, calcium edetate, carnsylate, carbonate, edetate, edisylate, estolate, esylate, gluceptate, gluconate, glutamate, glycollylarsanilate, hexylresorcinate, hydrabamine, hydroxynaphthoate, iodide, isethionate, lactobionate, malate, mesylate, mucate, napsylate, nitrate, pamoate (embonate), pantothenate, phosphate/diphosphate, polygalacturonate, salicylate, stearate, subacetate, sulfate, tannate, and teoclate, also are included.

Also included are salts of amino acids, such as arginate and the like, and salts of organic acids, such as, glucuronic or galactunoric acids, and the like. See, for example, Berge et al, "Pharmaceutical Salts", Journal of Pharmaceutical Science, 1977, 66, 1-19. Some compounds of the present disclosure can contain both basic and acidic functionalities, which allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties. For example, salts tend to be more soluble in aqueous or other protonic solvents than are the corresponding free base forms.

Certain compounds of the present disclosure can exist in unsolvated forms, as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In addition to salt forms, the present disclosure provides compounds that can be in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

D. Combination Therapies

In certain embodiments, presently disclosed subject matter also includes combination therapies. Depending on the particular disease, disorder, or condition to be treated or prevented, additional therapeutic agents, which are normally administered to treat or prevent that condition, may be administered in combination with the compounds of this disclosure. These additional agents may be administered separately, as part of a multiple dosage regimen, from the composition comprising a compound of Formula (I-V). Alternatively, these agents may be part of a single dosage form, mixed together with the compound of Formula (I-V) in a single composition.

By "in combination with" is meant the administration of a compound of Formula (I-V) with one or more therapeutic agents either simultaneously, sequentially, or a combination thereof. Therefore, a cell or a subject administered a combination of a compound of Formula (I-V) can receive a compound of Formula (I-V) and one or more therapeutic agents at the same time (i.e., simultaneously) or at different times (i.e., sequentially, in either order, on the same day or on different days), so long as the effect of the combination of both agents is achieved in the cell or the subject. When administered sequentially, the agents can be administered within 1, 5, 10, 30, 60, 120, 180, 240 minutes or longer of one another. In other embodiments, agents administered sequentially, can be administered within 1, 5, 10, 15, 20 or more days of one another. Where the compound of Formula (I-V) and one or more therapeutic agents are administered simultaneously, they can be administered to the cell or administered to the subject as separate pharmaceutical compositions, each comprising either a compound of Formula (I-V) or one or more therapeutic agents, or they can contact the cell as a single composition or be administered to a subject as a single pharmaceutical composition comprising both agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times. In such combination therapies, the therapeutic effect of the first administered compound is not diminished by the sequential, simultaneous or separate administration of the subsequent compound(s).

The presently disclosed compounds of Formula (I-V) can be optionally combined with or administered in concert with each other or other agents known to be useful in the treatment of the relevant disease, disorder, or condition. The combination therapies can involve concurrent or sequential administration, by the same or different routes, as determined to be appropriate by those of skill in the art. The presently disclosed subject matter also includes pharmaceutical compositions and kits including combinations as described herein.

Depending upon the particular condition, or disease state, to be treated or prevented, additional therapeutic agents, which are normally administered to treat or prevent that condition, may be administered together with the inhibitors of this disclosure. For example, chemotherapeutic agents or other antiproliferative agents may be combined with the inhibitors of this disclosure to treat proliferative diseases and cancer. Examples of known chemotherapeutic agents include, but are not limited to, adriamycin, dexamethasone, vincristine, cyclophosphamide, fluorouracil, topotecan, taxol, interferons, and platinum derivatives.

Other examples of agents in which the disclosed trioxane thioacetals also can be combined with include, without limitation, anti-inflammatory agents such as corticosteroids, TNF blockers, IL-I RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors, such as acetylcholinesterase inhibitors, MAO inhibitors, interferons, anti-convulsants, ion channel blockers, riluzole, and antiparkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders, such as corticosteroids, anti-leukemic agents, and growth factors; agents for treating diabetes such as insulin, insulin analogues, alpha glucosidase inhibitors, biguanides, and insulin sensitizers; and agents for treating immunodeficiency disorders such as gamma globulin.

These additional agents may be administered separately, as part of a multiple dosage regimen, from the inhibitor-containing composition. Alternatively, these agents may be part of a single dosage form, mixed together with the inhibitor in a single composition.

E. Dosage and Mode of Administration

The presently disclosed pharmaceutical compositions can be administered using a variety of methods known in the art depending on the subject and the particular disease, disorder, or condition being treated. The administering can be carried out by, for example, intravenous infusion; injection by intravenous, intraperitoneal, intracerebral, intramuscular, intraocular, intraarterial or intralesional routes; or topical or ocular application.

More particularly, as described herein, the presently disclosed compounds can be administered to a subject for therapy by any suitable route of administration, including orally, nasally, transmucosally, ocularly, rectally, intravaginally, parenterally, including intramuscular, subcutaneous, intramedullary injections, as well as intrathecal, direct intraventricular, intravenous, intra-articullar, intra-sternal, intrasynovial, intra-hepatic, intralesional, intracranial, intraperitoneal, intranasal, or intraocular injections, intracisternally, topically, as by powders, ointments or drops (including eyedrops), including buccally and sublingually, transdermally, through an inhalation spray, or other modes of delivery known in the art.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The phrases "parenteral administration" and "administered parenterally" as used herein mean modes of administration other than enteral and topical administration, usually by injection, and includes, without limitation, intravenous, intramuscular, intarterial, intrathecal, intracapsular, intraorbital, intraocular, intracardiac, intradermal, intraperitoneal, transtracheal, subcutaneous, subcuticular, intraarticular, subcapsular, subarachnoid, intraspinal and intrasternal injection and infusion.

For intracerebral use, the compounds can be administered continuously by infusion into the fluid reservoirs of the CNS, although bolus injection may be acceptable. The presently disclosed compounds can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the presently disclosed compounds can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, J. Neural Transm. Suppl. 24:271, 1987; and DeYebenes et al., Mov. Disord. 2: 143, 1987.

The presently disclosed pharmaceutical compositions can be manufactured in a manner known in the art, e.g. by means of conventional mixing, dissolving, granulating, dragee-making, levitating, emulsifying, encapsulating, entrapping or lyophilizing processes.

More particularly, pharmaceutical compositions for oral use can be obtained through combination of active compounds with a solid excipient, optionally grinding a resulting mixture, and processing the mixture of granules, after adding suitable auxiliaries, if desired, to obtain tablets or dragee cores. Suitable excipients include, but are not limited to, carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethyl cellulose; and gums including arabic and tragacanth; and proteins, such as gelatin and collagen; and polyvinylpyrrolidone (PVP:povidone). If desired, disintegrating or solubilizing agents, such as cross-linked polyvinyl pyrrolidone, agar, alginic acid, or a salt thereof, such as sodium alginate, also can be added to the compositions.

Dragee cores are provided with suitable coatings, such as concentrated sugar solutions, which also can contain gum arabic, talc, polyvinylpyrrolidone, carbopol gel, polyethylene glycol (PEG), and/or titanium dioxide, lacquer solutions, and suitable organic solvents or solvent mixtures. Dyestuffs or pigments can be added to the tablets or dragee coatings for product identification or to characterize the quantity of active compound, e.g., dosage, or different combinations of active compound doses.

Pharmaceutical compositions suitable for oral administration include push-fit capsules made of gelatin, as well as soft, sealed capsules made of gelatin and a coating, e.g., a plasticizer, such as glycerol or sorbitol. The push-fit capsules can contain active ingredients admixed with a filler or binder, such as lactose or starches, lubricants, such as talc or magnesium stearate, and, optionally, stabilizers. In soft capsules, the active compounds can be dissolved or suspended in suitable liquids, such as fatty oils, liquid paraffin, or liquid polyethylene glycols (PEGs), with or without stabilizers. Stabilizers can be added as warranted.

In some embodiments, the presently disclosed pharmaceutical compositions can be administered by rechargeable or biodegradable devices. For example, a variety of slow-release polymeric devices have been developed and tested in vivo for the controlled delivery of drugs, including proteinacious biopharmaceuticals. Suitable examples of sustained release preparations include semipermeable polymer matrices in the form of shaped articles, e.g., films or microcapsules. Sustained release matrices include polyesters, hydrogels, polylactides (U.S. Pat. No. 3,773,919; EP 58,481), copolymers of L-glutamic acid and gamma ethyl-L-glutamate (Sidman et al., Biopolymers 22:547, 1983), poly (2-hydroxyethyl-methacrylate) (Langer et al., J. Biomed. Mater. Res. 15:167, 1981; Langer, Chem. Tech. 12:98, 1982), ethylene vinyl acetate (Langer et al., Id), or poly-D-(−)-3-hydroxybutyric acid (EP 133,988A). Sustained release compositions also include liposomally entrapped compounds, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544,545; and EP 102,324A). Ordinarily, the liposomes are of the small (about 200-800 Angstroms) unilamelar type in which the lipid content is greater than about 30 mol % cholesterol, the selected proportion being adjusted for the optimal therapy. Such materials can comprise an implant, for example, for sustained release of the presently disclosed compounds, which, in some embodiments, can be implanted at a particular, predetermined target site.

Pharmaceutical compositions for parenteral administration include aqueous solutions of active compounds. For injection, the presently disclosed pharmaceutical compositions can be formulated in aqueous solutions, for example, in some embodiments, in physiologically compatible buffers, such as Hank's solution, Ringer' solution, or physiologically buffered saline. Aqueous injection suspensions can contain substances that increase the viscosity of the suspension, such as sodium carboxymethyl cellulose, sorbitol, or dextran. Additionally, suspensions of the active compounds or vehicles include fatty oils, such as sesame oil, or synthetic fatty acid esters, such as ethyl oleate or triglycerides, or liposomes. Optionally, the suspension also can contain suitable stabilizers or agents that increase the solubility of the compounds to allow for the preparation of highly concentrated solutions.

For nasal or transmucosal administration generally, penetrants appropriate to the particular barrier to be permeated are used in the formulation. Such penetrants are generally known in the art.

For inhalation delivery, the agents of the disclosure also can be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Additional ingredients can be added to compositions for topical administration, as long as such ingredients are pharmaceutically acceptable and not deleterious to the epithelial cells or their function. Further, such additional ingredients should not adversely affect the epithelial penetration efficiency of the composition, and should not cause deterioration in the stability of the composition. For example, fragrances, opacifiers, antioxidants, gelling agents, stabilizers, surfactants, emollients, coloring agents, preservatives, buffering agents, and the like can be present. The pH of the presently disclosed topical composition can be adjusted to a physiologically acceptable range of from about 6.0 to about 9.0 by adding buffering agents thereto such that the composition is physiologically compatible with a subject's skin.

In other embodiments, the pharmaceutical composition can be a lyophilized powder, optionally including additives, such as 1 mM-50 mM histidine, 0.1%-2% sucrose, 2%-7% mannitol at a pH range of 4.5 to 5.5 that is combined with buffer prior to use.

The presently disclosed subject matter also includes the use of a compound of Formula (I-V) in the manufacture of a medicament for treating the presently disclosed diseases.

Regardless of the route of administration selected, the presently disclosed compounds, which may be used in a suitable hydrated form, and/or the pharmaceutical compositions are formulated into pharmaceutically acceptable dosage forms such as described below or by other conventional methods known to those of skill in the art.

The term "effective amount," as in "a therapeutically effective amount," of a therapeutic agent refers to the amount of the agent necessary to elicit the desired biological response. As will be appreciated by those of ordinary skill in this art, the effective amount of an agent may vary depending on such factors as the desired biological endpoint, the agent to be delivered, the composition of the pharmaceutical composition, the target tissue or cell, and the like. More particularly, the term "effective amount" refers to an amount sufficient to produce the desired effect, e.g., to reduce or ameliorate the severity, duration, progression, or onset of a disease, disorder, or condition, or one or more symptoms thereof; prevent the advancement of a disease, disorder, or condition, cause the regression of a disease, disorder, or condition; prevent the recurrence, development, onset or progression of a symptom associated with a disease, disorder, or condition, or enhance or improve the prophylactic or therapeutic effect(s) of another therapy.

Actual dosage levels of the active ingredients in the presently disclosed pharmaceutical compositions can be varied so as to obtain an amount of the active ingredient that is effective to achieve the desired therapeutic response for a particular subject, composition, route of administration, and disease, disorder, or condition without being toxic to the subject. The selected dosage level will depend on a variety of factors including the activity of the particular compound employed, or salt thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of Formula (I-V) employed in the pharmaceutical composition at levels lower than that required to achieve the desired therapeutic effect and gradually increase the dosage until the desired effect is achieved. Accordingly, the dosage range for administration will be adjusted by the physician as necessary. It will be appreciated that an amount of a compound required for achieving the desired biological response may be different from the amount of compound effective for another purpose.

In general, a suitable daily dose of a compound of Formula (I-V) will be that amount of the compound that is the lowest dose effective to produce a therapeutic effect. Such an effective dose will generally depend upon the factors described above. Generally, doses of the compounds of Formula (I-V) will range from about 0.0001 to about 1000 mg per kilogram of body weight of the subject per day. In certain embodiments, the dosage is between about 1 µg/kg and about 500 mg/kg, more preferably between about 0.01 mg/kg and about 50 mg/kg. For example, in certain embodiments, a dose can be about 1, 5, 10, 15, 20, or 40 mg/kg/day.

If desired, the effective daily dose of the active compound can be administered as two, three, four, five, six or more sub-doses administered separately at appropriate intervals throughout the day, optionally, in unit dosage forms.

F. Kits or Pharmaceutical Systems

The presently disclosed compounds and compositions can be assembled into kits or pharmaceutical systems for use in treating or preventing the presently disclosed diseases, disorders, or conditions. In some embodiments, the presently disclosed kits or pharmaceutical systems include a compound of Formula (I-V) or pharmaceutically acceptable salts thereof. In particular embodiments, the compounds of Formula (I-V), or a pharmaceutically acceptable salt thereof, are in unit dosage form. In further embodiments, the compound of Formula (I-V), or a pharmaceutically acceptable salt, can be present together with a pharmaceutically acceptable solvent, carrier, excipient, or the like, as described herein.

In some embodiments, the presently disclosed kits comprise one or more containers, including, but not limited to a vial, tube, ampule, bottle and the like, for containing the compound. The one or more containers also can be carried within a suitable carrier, such as a box, carton, tube or the like. Such containers can be made of plastic, glass, laminated paper, metal foil, or other materials suitable for holding medicaments.

In some embodiments, the container can hold a composition that is by itself or when combined with another composition effective for treating or preventing the condition and may have a sterile access port (for example the container may be an intravenous solution bag or a vial having a stopper pierceable by a hypodermic injection needle). Alternatively, or additionally, the article of manufacture may further include a second (or third) container including a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The presently disclosed kits or pharmaceutical systems also can include associated instructions for using the compounds for treating or preventing a disease, disorder, or condition. In some embodiments, the instructions include one or more of the following: a description of the active compound; a dosage schedule and administration for treating or preventing a disease, disorder, or condition; precautions; warnings; indications; counter-indications; overdosage information; adverse reactions; animal pharmacology; clinical studies; and references. The instructions can be printed directly on a container (when present), as a label applied to the container, as a separate sheet, pamphlet, card, or folder supplied in or with the container.

G. Chemical Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of Formula (I-V) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted, for example, with fluorine at one or more positions).

Where substituent groups or linking groups are specified by their conventional chemical formulae, written from left to right, they equally encompass the chemically identical substituents that would result from writing the structure from right to left, e.g., —$CH_2O$— is equivalent to —$OCH_2$—; —C(=O)O— is equivalent to —OC(=O)—; —OC(=O)NR— is equivalent to —NRC(=O)O—, and the like.

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, iso-propyl, cyclopropyl, allyl, vinyl, n-butyl, tert-butyl, ethynyl, cyclohexyl, methoxy, diethylamino, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_1$-$C_{10}$ means one to ten carbons). In particular embodiments, the term "alkyl" refers to $C_{1-20}$ inclusive, linear (i.e., "straight-chain"), branched, or cyclic, saturated or at least partially and in some cases fully unsaturated (i.e., alkenyl and alkynyl)hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_{25}$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$.

As described above, heteroalkyl groups, as used herein, include those groups that are attached to the remainder of the molecule through a heteroatom, such as —C(O)R', —C(O)NR', —NR'R", —OR', —SR, and/or —SO$_2$R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{1-20}$ inclusive straight or branched hydrocarbon moiety having at least one carbon-carbon double bond by the removal of a single hydrogen atom. Alkenyl groups include, for example, ethenyl (i.e., vinyl), propenyl, butenyl, 1-methyl-2-buten-1-yl, pentenyl, hexenyl, octenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, heptynyl, and allenyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH=CH—CH=CH—; —CH=CH—$CH_2$—; —$CH_2CH_2CH_2CH_2$—, —$CH_2CH$=$CHCH_2$—, —$CH_2CsCCH_2$—, —$CH_2CH_2CH$($CH_2CH_2CH_3$)$CH_2$—, —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxo, arylthioxo, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

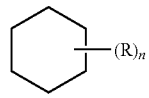

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

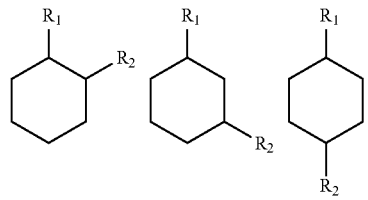

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol ( ⁓⁓⁓⁓ ) denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R'', —SR', -halogen, —SiR'R''R''', —OC(O)R', —C(O)R', —CO$_2$R', —C(O)NR'R'', —OC(O)NR'R'', —NR''C(O)R', —NR'—C(O)NR''R''', —NR''C(O)OR', —NR—C(NR'R'')=NR''', —S(O)R', —S(O)$_2$R', —S(O)$_2$NR'R'', —NRSO$_2$R', —CN and —NO$_2$ in a number ranging from zero to (2 m'+1), where m' is the total number of carbon atoms in such groups. R', R'', R''' and R'''' each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R'', R''' and R'''' groups when more than one of these groups is present. When R' and R'' are attached to the same nitrogen atom, they can be combined with the nitrogen atom to form a 4-, 5-, 6-, or 7-membered ring. For example, —NR'R'' is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl groups above, exemplary substituents for aryl and heteroaryl groups (as well as their divalent derivatives) are varied and are selected from, for example: halogen, —OR', —NR'R'', —SR', -halogen, —SiR'R''R''', —OC(O)R', —C(O)R', —CO$_2$R', —C(O)NR'R'', —OC(O)NR'R'', —NR''C(O)R', —NR'—C(O)NR''R''', —NR''C(O)OR', —NR—C(NR'R''R''')=NR'''', —NR—C(NR'R'')=NR'''—S(O)R', —S(O)$_2$R', —S(O)$_2$NR'R'', —NRSO$_2$R', —CN and —NO$_2$, —R', —N$_3$, —CH(Ph)$_2$, fluoro(C$_1$-C$_4$)alkoxo, and fluoro (C$_1$-C$_4$)alkyl, in a number ranging from zero to the total number of open valences on aromatic ring system; and where R', R'', R''' and R'''' may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R''' and R"" groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R''')$_d$—, where s and d are independently integers of from 0 to 3, and X' is —O—, —NR'—, —S—, —S(O)—, —S(O)$_2$—, or —S(O)$_2$NR'—. The substituents R, R', R" and R''' may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocyclic, heterocyclic, or aromatic heterocyclic group as defined herein). As such, the term "acyl" specifically includes arylacyl groups, such as an acetylfuran and a phenacyl group. Specific examples of acyl groups include acetyl and benzoyl.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include C$_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, t-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O group wherein the aralkyl group is as previously described. An exemplary aralkyloxyl group is benzyloxyl.

"Alkoxycarbonyl" refers to an alkyl-O—CO group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO group. Exemplary aryloxycarbonyl groups include phenoxy- and naphthoxy-carbonyl.

"Aralkoxycarbonyl" refers to an aralkyl-O—CO group. An exemplary aralkoxycarbonyl group is benzyloxycarbonyl.

"Carbamoyl" refers to an amide group of the formula CONH$_2$. "Alkylcarbamoyl" refers to a R'RN—CO— group wherein one of R and R' is hydrogen and the other of R and R' is alkyl and/or substituted alkyl as previously described. "Dialkylcarbamoyl" refers to a R'RN—CO— group wherein each of R and R' is independently alkyl and/or substituted alkyl as previously described.

The term carbonyldioxyl, as used herein, refers to a carbonate group of the formula —O—CO—OR.

"Acyloxyl" refers to an acyl-O group wherein acyl is as previously described.

The term "amino" refers to the —NH$_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure NR'R"R''', wherein R', R", and R''' are each independently selected from the group consisting of alkyl groups. Additionally, R', R", and/or R''' taken together may optionally be —(CH$_2$)$_k$— where k is an integer from 2 to 6. Examples include, but are not limited to, methylamino, dimethylamino, ethylamino, diethylamino, diethylaminocarbonyl, methylethylamino, iso-propylamino, piperidino, trimethylamino, and propylamino The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH group wherein acyl is as previously described. "Aroylamino" refers to an aroyl-NH group wherein aroyl is as previously described.

The term "carbonyl" refers to the —(C=O)— group.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —$NO_2$ group.

The term "thio" refers to a compound described previously herein wherein a carbon or oxygen atom is replaced by a sulfur atom.

The term "sulfate" refers to the —$SO_4$ group.

The term thiohydroxyl or thiol, as used herein, refers to a group of the formula —SH.

The term ureido refers to a urea group of the formula —NH—CO—$NH_2$.

Unless otherwise explicitly defined, a "substituent group," as used herein, includes a functional group selected from one or more of the following moieties, which are defined herein:

(A) —OH, —$NH_2$, —SH, —CN, —$CF_3$, —$NO_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "lower substituent" or "lower substituent group," as used herein means a group selected from all of the substituents described hereinabove for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

Throughout the specification and claims, a given chemical formula or name shall encompass all tautomers, congeners, and optical- and stereoisomers, as well as racemic mixtures where such isomers and mixtures exist.

Certain compounds of the present disclosure possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present disclosure. The compounds of the present disclosure do not include those which are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present disclosure, whether radioactive or not, are encompassed within the scope of the present disclosure.

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as tert-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(O)— catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups include, but are not limited to the following moieties:

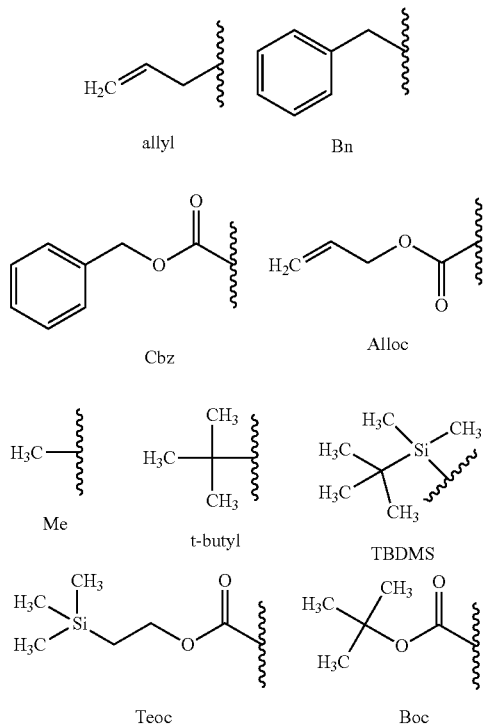

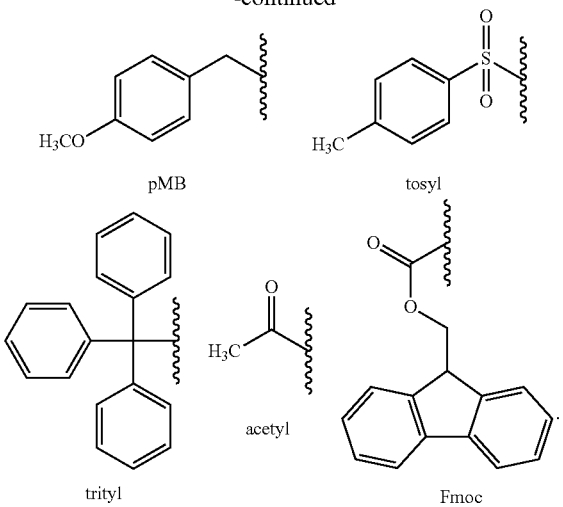

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Chemistry

In only 2 high-yielding chemical steps from natural artemisinin (1), a series of C-10 thioacetal alcohols 3a-3c was prepared (FIG. 1). In all cases, the C-10-α thioacetal diastereomer strongly predominated over the C-10-β diastereomer. Chromatography provided the pure C-10-α diastereomer. Based on its proton NMR $J_{9,10}$ coupling constant of 9-11 Hz, C-10-α thioacetal stereochemistry was assigned. See Oh, et al., 2003.

Previously a C-10-α phenylthioacetal and a C-10-α cyclohexylthioacetal were shown to be more antimalarially efficacious in mice than the corresponding C-10-β diastereomer. See Venugopalan, et al., 1995; Oh, et al., 2003. One-step O-alkylation gave propargyl ethers 3d and 3e, allylic ethers 3f and 3g, and benzylic ethers 3h-3j in good yields. One-step acylation converted thioacetal alcohols 3a-3c into esters 3l-3o, into carbonates 3p and 3q, and into carbamates 3r-3u also in good yields. Likewise, thioacetal carboxylic acids 4a-4c, prepared in only 2 steps and in good yield from artemisinin (FIG. 1), were easily converted directly into esters 4d-4g and into amides 4h and 4i.

Coupling of thioacetal alcohols 3a and 3b with thioacetal carboxylic acids 4a and 4b afforded separately trioxane dimer thioacetal esters 5a-5d as new chemical entities in good yields (FIG. 2). One previously prepared but structurally different C-10 trioxane thioacetal dimer was only weakly antimalarial in mice. Venugopalan, et al., 1995.

Thioacetals are known generally to be much less easily hydrolyzed than the corresponding non-sulfur-containing acetals. See Greene, et al., *Protective Groups in Organic Synthesis*; Satchell and Satchell, 1990. To illustrate this point, thioacetals 3h and 3r were dissolved in pH=2 water acetonitrile at 37° C. See Jung and Lee, 1998. After 24 hours, less than 2% hydrolysis into DHA (2a) occurred, as determined by $^1$H NMR spectroscopy; we were able to detect 2% DHA in a sample of thioacetal 3h and 3r doped with 2% of authentic DHA (having a characteristic NMR multiplet at 4.7 δ). Even at 60° C. for 7 days, neat thioacetals 3a, 3h, and 3r showed less than 2% decomposition.

Example 2

Representative Biological Data

Using a standard protocol, see Slack, et al., 2012, 20-gram mice were infected by intraperitonial injection with *P. berghei* malaria parasites. One day after infection, each mouse in groups of 4 mice received a single oral dose of 6 mg/kg body weight of a trioxane thioacetal combined with 18 mg/kg of the long-lived antimalarial mefloquine hydrochloride. In all cases, parasitemia was decreased by at least 99% on day 3 post infection. Malaria-infected mice receiving no antimalarial drug died on day 6 or 7 post infection. Critically, control groups of mice receiving 6 mg/kg of the popular trioxane drug artemether (2b) plus 18 mg/kg of mefloquine, or just 18 mg/kg of mefloquine alone, survived for about 3 weeks post infection. In contrast, several of the presently disclosed trioxane thioacetals prolonged mouse survival for longer than 3 weeks, and in some instances produced partial cures; for example, 2 of 4 mice in one group (diisopropyl carbamate 3u) appeared healthy and had no detectable parasitemia on day 30 post infection. The most highly efficacious of the presently disclosed trioxane thioacetals appear to be fluorinated benzyl ether 3h, benzotriazole ether 3k, and diisopropyl carbamate 3u.

The antimalarial efficacy of representative presently disclosed C-10 thioacetals, as well as controls, is summarized in Table 1, which includes the parasitemia levels for mice on day 3 post-infection.

TABLE 1

In Vivo Antimalarial Efficacy Using a Single Oral Dose of 6 mg/kg Trioxane and 18 mg/kg Mefloquine Hydrochloride in *P. berghei*-Infected Mice

| trioxane | average survival (days) after infection | % suppression of parasitemia (on day 3 post infection) |
|---|---|---|
| 109 | 24.5 (30, 30, 21, 17) | >99.9% |
| 110 | 19.3 (30, 17, 15, 15) | >99.9% |
| 111 | 29.8 (30, 30, 30, 29) | 99.9% |
| 114 | 22.0 (30, 28, 17, 13) | 99.9% |
| Controls | | |
| infected (no drug) | 8.0 (10, 8, 7, 7) | 0% |
| artemether + mefloquine-HCl | 16.5 (28, 13, 13, 12) | >99.9% |
| mefloquine-HCl only | 14.0 (17, 13, 13, 13) | >99.9% |

Example 3

Experimental Methods and Analytical Data

Art-10α-S(CH$_2$)$_3$OH (3a)

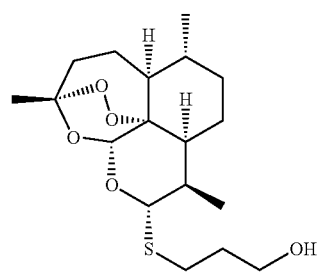

An oven-dried, 5 dram vial, equipped with a magnetic stir bar, under argon was charged with dihydroartemisinin (2a, 250 mg, 0.88 mmol, 1.0 equiv) and anhydrous dichloromethane (10 mL). 3-Mercaptopropanol (89 mg, 0.97 mmol, 1.1 equiv) was added and allowed to stir for 10 min at 50° C., under argon. Boron trifluoride etherate (0.125 mL, 0.88 mmol, 1.0 equiv) was added dropwise and the reaction was allowed to stir under argon at 50° C. for 30 min. After 30 min, the reaction was quenched with water (5 mL) and extracted with dichloromethane (3×10 mL). The organic layers were combined, dried over $MgSO_4$, and concentrated on a rotary evaporator at room temperature. The $^1H$ NMR of the crude reaction mixture indicated a mixture of 10-α and 10-β diastereomers in a ratio of 9:1 (α:β). The crude amorphous solid was purified via column chromatography (10% ethyl acetate in hexanes) to afford the desired product 3a as an amorphous solid (225 mg, 72% yield). $[\alpha]_D^{23.3}$+31.49 (c. 0.58, $CHCl_3$). IR (thin film) 3445, 2926, 2871, 2363, 1716, 1586, 1446, 1378, 1279, 1195, 1126, 1035, 928, 900, 878 $cm^{-1}$. $^1H$ NMR (400 MHz, $CDCl_3$) δ 5.29 (s, 2H), 4.53 (d, J=10.8 Hz, 1H)*, 3.86-3.72 (m, 2H), 2.97-2.94 (m, 1H), 2.73-2.68 (m, 1H), 2.64-2.60 (m, 1H), 2.38-2.31 (m, 2H), 2.02-1.95 (m, 1H), 1.93-1.68 (m, 5H), 1.60-1.57 (m, 1H), 1.49-1.20 (m, 9H), 1.05-0.99 (m, 1H), 0.92 (dd, J=11.2, 6.0 Hz, 6H). $^{13}C$ NMR (100 MHz, $CDCl_3$) δ 104.6, 92.4, 80.7, 80.5, 59.6, 51.7, 45.9, 37.4, 36.2, 34.0, 32.1, 31.8, 25.7, 24.7, 23.9, 21.3, 20.2, 15.0. HRMS (FAB) m/z calcd. for 359.1892 $[M+H^+]$. found 359.1888.

Art-10α-S(CH$_2$)$_6$OH (3b)

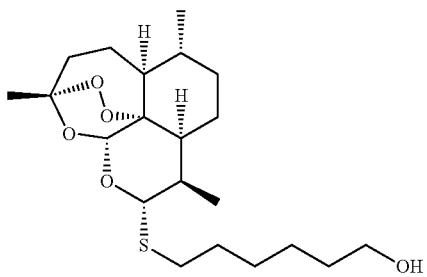

An oven-dried, 2-dram vial, equipped with a magnetic stir bar, under argon was charged with dihydroartemisinin (2a, 50 mg, 0.18 mmol, 1.0 equiv) and anhydrous dichloromethane (2 mL). 6-Mercaptohexanol (26 mg, 0.19 mmol, 1.1 equiv) was added and allowed to stir for 10 min at room temperature (24° C.), under argon. Boron trifluoride etherate (25 mg, 0.18 mmol, 1.0 equiv) was added dropwise and the reaction was allowed to stir under argon at room temperature for 20 min. After 20 min, the reaction was quenched with water (2 mL) and extracted with dichloromethane (3×2 mL). The organic layers were combined, dried over $MgSO_4$, and concentrated on a rotary evaporator at room temperature. The $^1H$ NMR of the crude reaction mixture indicated a mixture of 10-α and 10-β diastereomers in a ratio of 4:1 (α:β). The crude residue was purified via column chromatography (10% ethyl acetate in hexanes) to afford the desired product 3b as a clear solid (45 mg, 64% yield). $[\alpha]_D^{24.0}$+14.6 (c. 0.65, $CHCl_3$); IR (thin film) ν 3458, 2927, 2871, 1455, 1377, 1128, 1037, 928, 879, 829, 666 $cm^{-1}$; $^1H$ NMR (400 MHz, $CDCl_3$) δ 5.27 (s, 1H), 4.51 (d, J=10.8 Hz, 1H), 3.63 (br t, J=6.4 Hz, 2H), 2.81-2.74 (m, 1H), 2.68-2.56 (m, 2H), 2.36 (td, J=12.0, 4.0 Hz, 1H), 2.03-1.98 (m, 1H), 1.90-1.83 (m, 1H), 1.72-1.20 (m, 20H), 1.07-0.99 (m, 1H), 0.95 (d, J=4.0 Hz, 3H), 0.92 (d, J=4.0 Hz, 3H); $^{13}C$ NMR (100 MHz, $CDCl_3$) δ104.3, 92.3, 80.6, 80.4, 62.9, 51.8, 46.0, 37.4, 36.3, 34.1, 32.6, 31.7, 29.7, 28.6, 28.1, 25.8, 25.2, 24.7, 21.3, 20.3, 15.1; HRMS (FAB) m/z calcd for $C_{21}H_{36}O_5S$ $(M+H^+)$ 401.2362. found 401.2355.

Art-10α-S(CH$_2$)$_{11}$OH (3c)

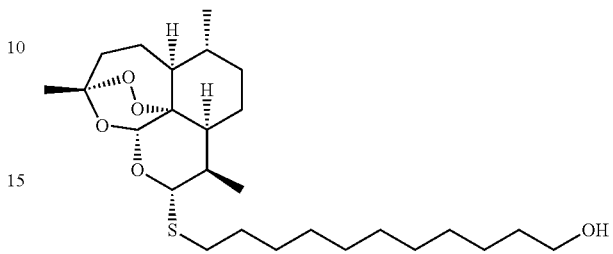

Followed the same procedure for the preparation of alcohol 3b, replacing 6-mercaptohexanol with 11-mercaptoundecanol, to produce the titled compound 3c as a white amorphous solid (50 mg, 60% yield). $[\alpha]_D^{21.8}$+2.0 (c. 0.53, $CHCl_3$); IR (thin film) ν 3583, 2925, 2853, 1698, 1450, 1377, 1233, 1195, 1128, 1037 $cm^{-1}$; $^1H$ NMR (400 MHz, $CDCl_3$) δ 5.27 (s, 1H), 4.51 (d, J=10.4 Hz, 1H), 3.63 (br t, J=4 Hz, 2H), 2.79-2.72 (m, 1H), 2.67-2.56 (m, 2H), 2.36 (td, J=12.0, 4.0 Hz, 1H), 2.03-1.98 (m, 1H), 1.90-1.83 (m, 1H), 1.74-1.20 (m, 28H), 1.06-0.97 (m, 1H), 0.95 (d, J=4.0 Hz, 3H), 0.92 (d, J=8.0 Hz, 3H); $^{13}C$ NMR (100 MHz, $CDCl_3$) δ 104.3, 92.3, 80.6, 80.4, 63.1, 51.8, 46.1, 37.4, 36.3, 34.1, 32.8, 31.7, 29.9, 29.6, 29.5, 29.4, 29.3, 29.1, 28.3, 26.0, 25.7, 24.8, 21.3, 20.3, 15.1; HRMS (FAB) m/z calcd for $C_{26}H_{46}O_5S$ $(M+H^+)$ 471.3144. found 471.3138.

Art-10α-S(CH$_2$)$_3$OCH$_2$C≡CH (3d)

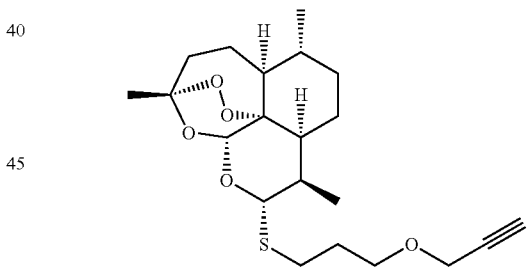

An oven-dried, 2-dram vial, equipped with a magnetic stir bar, under argon was charged with thioacetal 3a (17.7 mg, 0.05 mmol, 1.0 equiv) and anhydrous acetonitrile (0.7 mL). Sodium hydride (95%, 2.5 mg, 0.10 mmol, 2 equiv) was added as a solid in one portion and allowed to stir for 5 min at room temperature (24° C.), under argon. Propargyl chloride (15.7 mg, 0.21 mmol, 4 equiv) was added dropwise and the reaction was allowed to stir under argon at room temperature (24° C.) for 24 h. After 24 h, the reaction was quenched with water (1 mL) and extracted with dichloromethane (3×1 mL). The organic layers were combined, dried over $MgSO_4$, and concentrated on a rotary evaporator at room temperature. The crude residue was purified via column chromatography (5-10% ethyl acetate in hexanes) to afford the desired product 3d as an amorphous solid (7 mg, 34% yield). $^1H$ NMR (400 MHz, $CDCl_3$) δ 5.27 (s, 1H), 4.53 (d, J=12.0 Hz, 1H), 4.14 (d, J=2.4 Hz, 2H), 3.63 (t, J=8.0 Hz, 2H), 2.90-2.83 (m, 1H), 2.77-2.70 (m, 1H), 2.65-2.55 (m, 1H), 2.41 (t, J=2.4 Hz, 1H), 2.36 (td, J=14.0, 4.0 Hz, 1H), 2.04-1.93 (m, 3H), 1.91-1.84 (m, 1H), 1.74-1.69 (m, 2H), 1.61-1.20 (m, 10H), 1.08-1.00 (m, 1H), 0.95 (d, J=8.0 Hz, 3H), 0.92 (d, J=8.0 Hz, 3H); HRMS (FAB) m/z calcd for C$_{21}$H$_{32}$O$_5$S (M+H$^+$) 397.2049. found 397.2038.

Art-10α-S(CH$_2$)$_6$OCH$_2$C≡CH (3e)

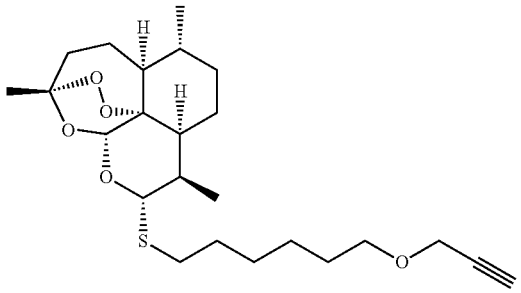

Followed the same procedure for the preparation of propargyl ether 3d, replacing 3a with 3b, to produce the titled compound 3e as a clear oil (9.4 mg, 40% yield). $^1$H NMR (400 MHz, CDCl$_3$) δ 5.27 (s, 1H), 4.52 (d, J=12.0 Hz, 1H), 4.12 (d, J=4.0 Hz, 2H), 3.50 (t, J=8.0 Hz, 2H), 2.81-2.74 (m, 1H), 2.68-2.56 (m, 2H), 2.41 (t, J=4.0 Hz, 1H), 2.36 (td, J=16.0, 4.0 Hz, 1H), 2.04-1.98 (m, 1H), 1.90-1.83 (m, 1H), 1.75-1.20 (m, 22H), 1.08-1.00 (m, 1H), 0.95 (d, J=8.0 Hz, 3H), 0.92 (d, J=8.0 Hz, 3H).

Art-10α-S(CH$_2$)$_3$OCH$_2$C(Cl)CH$_2$ (3l)

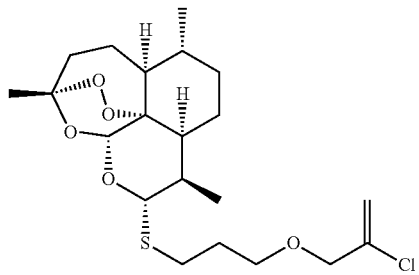

An oven-dried, 2-dram vial, equipped with a magnetic stir bar, under argon was charged with thioacetal 3a (17.0 mg, 0.05 mmol, 1.0 equiv) and anhydrous acetonitrile (0.4 mL). Sodium hydride (95%, 2.4 mg, 0.10 mmol, 2 equiv) was added as a solid in one portion and allowed to stir for 5 min at room temperature (24° C.), under argon. 2,3-Dichloropropene (22.2 mg, 0.20 mmol, 4 equiv) was added dropwise and the reaction was allowed to stir under argon at room temperature (24° C.) for 24 h. After 24 h, an additional portion of sodium hydride (2.4 mg, 0.10 mmol, 2 equiv) and 2,3-dichlorpropene (22.2 mg, 0.20 mmol, 4 equiv) were added and the reaction was stirred for 12 h. The reaction was quenched with water (0.5 mL) and extracted with dichloromethane (3×1 mL). The organic layers were combined, dried over MgSO$_4$, and concentrated on a rotary evaporator at room temperature. The crude residue was purified via column chromatography (5-10% ethyl acetate in hexanes) to afford the desired product 3f a clear oil (5.0 mg, 24% yield).

Unreacted alcohol starting material 3a was isolated, which accounted for the remaining mass. $^1$H NMR (300 MHz, CDCl$_3$) δ 5.47 (app s, 1H), 5.35 (app s, 1H), 5.27 (s, 1H), 5.53 (d, J=12.0 Hz, 1H), 4.03 (app s, 2H), 3.60 (t, J=6.0 Hz, 2H), 2.93-2.84 (m, 1H), 2.79-2.70 (m, 1H), 2.67-2.55 (m, 1H), 2.36 (td, J=12.0, 6.0 Hz, 1H), 2.04-1.84 (m, 4H), 1.74-1.19 (m, 15H), 0.95 (d, J=6.0 Hz, 3H), 0.92 (d, J=6.0 Hz, 3H).

Art-10α-S(CH$_2$)$_6$OCH$_2$C(Cl)CH$_2$ (3g)

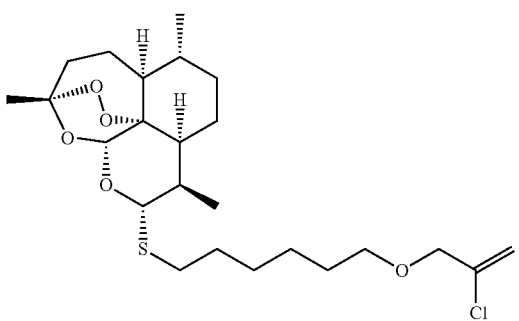

Followed the same procedure for the preparation of allyl ether 3f, replacing thioacetal 3a with thioacetal 3b, to produce the titled compound 3g as a clear oil (6.4 mg, 23% yield). Unreacted alcohol starting material 3b was isolated, which accounted for the remaining mass. $^1$H NMR (400 MHz, CDCl$_3$) δ 5.45 (br s, 1H), 5.35 (br s, 1H), 5.28 (s, 1H), 4.52 (d, J=12.0 Hz, 1H), 4.02 (s, 2H), 3.46 (t, J=8.0 Hz, 2H), 2.81-2.57 (m, 3H), 2.41-2.33 (m, 1H), 2.04-1.01 (m, 34H), 0.95 (d, J=8.0 Hz, 3H), 0.92 (d, J=8.0 Hz, 3H).

Art-10α-S(CH$_2$)$_3$OCH$_2$PhF-4 (3h)

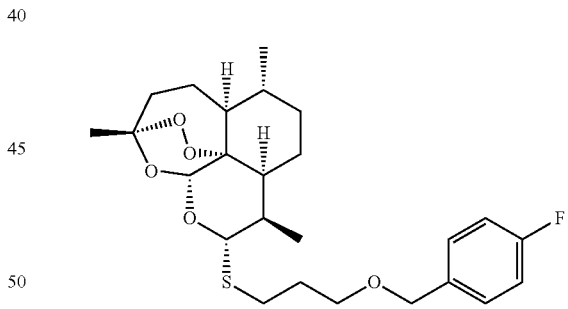

An oven-dried, 2 dram vial, equipped with a magnetic stir bar, under argon was charged with artemisinin thioacetal 3a (10 mg, 0.028 mmol, 1.0 equiv) and acetonitrile (1.5 mL). Sodium hydride (95%, 0.42 mmol, 1.0 mg, 1.5 equiv) was added and the mixture was allowed to stir for 15 min. After 15 min the desired fluorobenzyl bromide (0.42 mmol, 1.5 equiv) was added and the reaction was allowed to stir under argon for 24 hr. After 24 hr the reaction was quenched with water (5 mL) and extracted with dichloromethane (3×10 mL). The organic layers were combined, dried over MgSO$_4$, filtered, and concentrated on a rotary evaporator at room temperature. The crude amorphous solids were purified via column chromatography (5% ethyl acetate in hexanes) to afford the desired product 3h as a white amorphous solid (7.5 mg, 57% yield). [α]$_D^{22.9}$+18.49 (c. 0.91, CHCl$_3$). IR (thin film) 2926, 2870, 1707, 1603, 1509, 1449, 1377, 1278, 1221, 1195, 1153, 1127, 1093, 1037, 959, 928, 900, 879 cm$^{-1}$. $^1$H NMR (300 MHz, CDCl$_3$) δ 7.32-7.28 (m, 2H), 7.07-6.98 (m, 2H), 5.25 (s, 1H), 4.52 (d, J=10.5 Hz, 1H), 4.46 (s, 2H), 3.61-3.54 (m, 2H), 2.92-2.86 (m, 1H), 2.80-2.72 (m, 1H), 2.62-2.56 (m, 1H), 2.42-2.30 (m, 1H), 2.05-1.82 (m, 5H), 1.75-1.52 (m, 4H), 1.48-1.40 (m, 1H), 1.39 (s, 3H), 1.36-1.19 (m, 3H), 1.09-0.99 (m, 1H), 0.93 (dd, J=9.9, 6.0 Hz, 6H). $^{13}$C NMR (75 MHz, CDCl$_3$) δ 160.6, 134.3, 129.3 (d, $J_{C-F}$=5.4 Hz), 115.2 (d, $J_{C-F}$=21.2 Hz), 104.3, 92.2, 80.7, 80.4, 72.1, 68.9, 51.8, 46.0, 37.4, 36.3, 34.1, 31.7, 30.0, 25.9, 25.3, 24.7, 21.3, 20.2, 15.1. HRMS (FAB) m/z calcd for 467.2268 [M+H$^+$]. found 467.2265.

Art-10α-S(CH$_2$)$_6$OCH$_2$PhF-4 (3i)

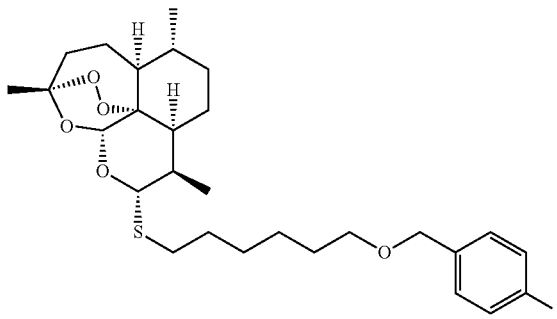

Followed the same procedure for the preparation of aryl ether 3h, replacing 3a with 3b, to produce the titled compound 3i as a clear oil (10.2 mg, 41% yield). After column chromatography purification, unreacted alcohol 3b was isolated, which accounted for the remaining mass. [α]$_D^{21.9}$+ 14.9 (c. 0.51, CHCl$_3$); IR (thin film) ν 2926, 2853, 1603, 1509, 1452, 1376, 1223, 1093, 1037, 928, 880, 827, 666 cm$^{-1}$; $^1$H NMR (300 MHz, CDCl$_3$) δ 7.30 (m, 2H), 7.02 (m, 2H), 5.27 (s, 1H), 4.51 (d, J=10.5 Hz, 1H), 4.45 (app s, 2H), 3.24 (t, J=6.0 Hz, 2H), 2.82-2.72 (m, 1H), 2.69-2.55 (m, 2H), 2.36 (td, J=12.0, 3.0 Hz, 1H), 2.05-1.97 (m, 1H), 1.91-1.83 (m, 1H), 1.73-1.19 (m, 21H), 1.08-1.00 (m, 1H), 0.95 (d, J=6.0 Hz, 3H), 0.92 (d, J=6.0 Hz, 3H); $^{13}$C NMR (75 MHz, CDCl$_3$) δ 162.3 (d, $J_{C-F}$=243.8 Hz), 134.4 (d, $J_{C-F}$=3.0 Hz), 129.3 (d, $J_{C-F}$=8.3 Hz), 115.2 (d, $J_{C-F}$=21.8 Hz), 104.3, 92.3, 80.5, 80.4, 72.2, 70.4, 51.8, 46.0, 37.4, 36.3, 34.1, 31.7, 29.8, 29.6, 28.9, 28.2, 26.0, 25.8, 24.8, 21.3, 20.3, 15.1; HRMS (FAB) m/z calcd for C$_{28}$H$_{41}$FO$_5$S (M+H$^+$), 509.2737 found 509.2718.

Art-10α-S(CH$_2$)$_{11}$OCH$_2$PhF-4 (3j)

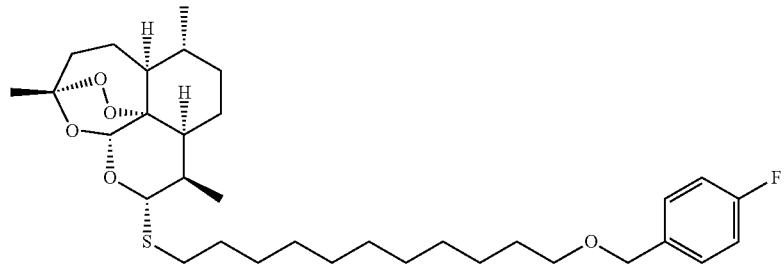

Followed the same procedure for the preparation of aryl ether 3h, replacing 3a with 3c, to produce the titled compound 3j as a clear oil (10.0 mg, 37% yield). After column chromatography purification, unreacted alcohol 3c was also isolated, which accounted for the remaining mass. [α]$_D^{23.0}$+ 3.6 (c. 0.39, CHCl$_3$); IR (thin film) ν 2925, 2852, 1653, 1558, 1541, 1508, 1457, 1223, 1037, 827, 666 cm$^{-1}$; $^1$H NMR (400 MHz, CDCl$_3$) δ 7.30 (m, 2H), 7.02 (m, 2H), 5.28 (s, 1H), 4.51 (d, J=12.0 Hz, 1H), 4.45 (app s, 2H), 3.45 (t, J=8.0 Hz, 2H), 2.80-2.73 (m, 1H), 2.68-2.57 (m, 2H), 2.39-2.32 (m, 1H), 2.04-1.98 (m, 1H), 1.90-1.84 (m, 1H), 1.72-1.01 (m, 30H), 0.95 (d, J=8.0 Hz, 3H), 0.92 (d, J=8.0 Hz, 3H); $^{13}$C NMR (75 MHz, CDCl$_3$) δ 162.3 (d, $J_{C-F}$=243.8 Hz), 134.5 (d, $J_{C-F}$=3.0 Hz), 129.3 (d, $J_{C-F}$=7.5 Hz), 115.2 (d, $J_{C-F}$=21.8 Hz), 104.3, 92.3, 80.6, 80.4, 72.3, 70.6, 51.8, 46.0, 43.5, 37.4, 37.0, 36.3, 34.1, 31.7, 29.9, 29.7, 29.6, 29.5, 29.5, 29.3, 29.1, 28.3, 26.2, 26.0, 24.8, 21.3, 20.3, 15.1; HRMS (FAB) m/z calcd for C$_{33}$H$_{51}$FO$_5$S (M+H$^+$) 579.3520. found 579.3525.

Art-10α-S(CH$_2$)$_3$OCH$_2$—N-benzotriazole (3k)

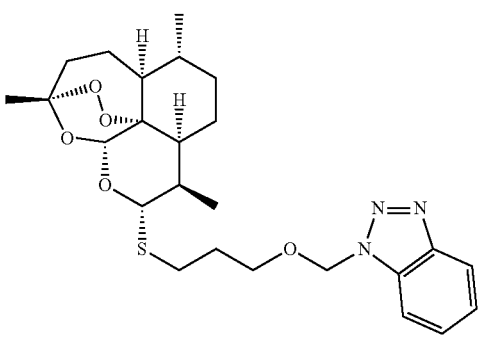

To a flame dried 10 mL round bottom flask was added C10-thioacetal alcohol 3a (18.8 mg, 0.052 mmol) and dissolved in MeCN (1 mL) under an Ar blanket. The solution was cooled to 0° C. and NaH (spatula tip) was added in one portion. The resulting mixture was allowed to stir for 20 minutes before commercially available 1-(chloromethyl)-1H-benzotriazole (Aldrich, 9.7 mg, 0.058 mmol) was added. The reaction was slowly warmed to room temperature over 2 hours upon which it was stirred for an additional 16 hours. The reaction was quenched with saturated NH$_4$Cl (aq, 3 mL) at 0° C. and extracted with CH$_2$Cl$_2$ (3×3 mL). The organic extracts were combined, dried with MgSO$_4$, and concentrated in vacuo. The crude product was purified by column chromatography (5-30% EtOAc/Hex) to afford benzotriazole 3k as an amorphous solid (55% yield, 14.0 mg, 0.029 mmol). [α]$_D^{22}$=+2.12 (CHCl$_3$, c=0.605). FTIR (thin film) ν 2926, 2872, 1453, 1377, 1273, 1152, 1100, 1036. $^1$H NMR (400 MHz, CDCl$_3$) δ 8.08 (d, J=8.4 Hz, 1H), 7.70 (d, J=8.4 Hz, 1H), 7.53 (t, J=7.2 Hz, 1H), 7.40 (t, J=7.6 Hz, 1H), 6.01 (s, 2H), 5.23 (s, 1H), 4.44 (d, J=10.4 Hz, 1H), 3.61 (m, 2H), 2.77 (m, 1H), 2.65-2.51 (m, 2H), 2.34 (td, J=14.4, 4.0 Hz, 1H), 2.01-1.84 (m, 4H), 1.71-1.19 (m, 7H), 1.37 (s, 3H), 1.02 (m, 1H), 0.94 (d, J=6.4 Hz, 3H), 0.85 (d, J=7.2 Hz, 3H). $^{13}$C NMR (100 MHz, CDCl$_3$) δ 146.4, 132.8, 120.0, 104.2, 92.2, 80.5, 80.3, 68.0, 51.7, 45.9, 37.3, 36.2, 34.0, 31.5, 29.5, 24.9, 24.7, 21.2, 20.2. HRMS (ESI) m/z calculated for C$_{25}$H$_{36}$N$_3$O$_5$S (M+H)$^+$490.2370. found 490.2375.

AMJ-Art-10α-S(CH$_2$)$_3$OC(O)CH$_3$ (3l)

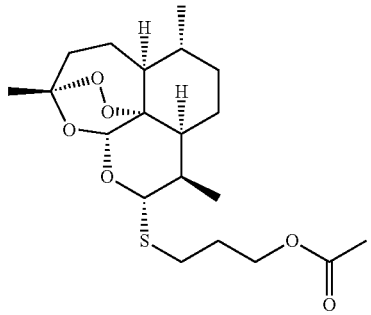

An oven-dried, 2 dram vial, equipped with a magnetic stir bar, under argon was charged with artemisinin thioacetal 3a (10 mg, 0.028 mmol, 1.0 equiv) and acetonitrile (1.5 mL). Sodium hydride (95%, 0.42 mmol, 1.0 mg, 1.5 equiv) was added and the mixture was allowed to stir for 15 min. After 15 min the desired anhydride (0.42 mmol, 1.5 equiv) (note— for 3o, the acid chloride was used because the anhydride was not commercially available) was added and the reaction was allowed to stir under argon for 24 hr. After 24 hr the reaction was quenched with water (5 mL) and extracted with dichloromethane (3×10 mL). The organic layers were combined, dried over MgSO$_4$, and concentrated on a rotary evaporator at room temperature. The crude amorphous solid was purified via column chromatography (10% ethyl acetate in hexanes) to afford the desired product 3l as a white amorphous solid (9.9 mg, 89% yield). $^1$H NMR (300 MHz, CDCl$_3$) δ 5.28 (s, 1H), 4.52 (d, J=10.8 Hz, 1H), 4.18 (t, J=6.4 Hz, 2H), 2.89-2.82 (m, 1H), 2.73-2.56 (m, 2H), 2.36 (td, J=14.4, 4.0 Hz, 1H), 2.08-1.98 (m, 6H), 1.92-1.84 (m, 1H), 1.78-1.68 (m, 2H), 1.62-1.56 (m, 3H), 1.51-1.21 (m, 8H), 1.09-1.01 (m, 1H), 0.94 (dd, J=11.6, 6.0 Hz, 6H).

Art-10α-S(CH$_2$)$_6$OC(O)CH$_3$ (3m)

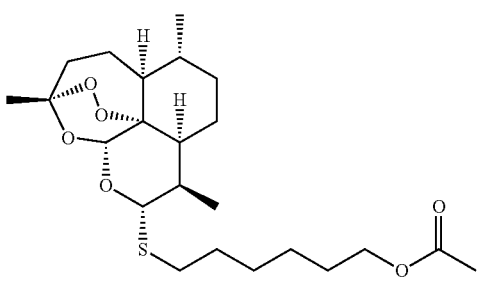

Followed the same procedure for the preparation of acetate 3l, replacing 3a with 3b, to produce titled compound 3m as a clear oil (16.4 mg, 60% yield). $^1$H NMR (300 MHz, CDCl$_3$) δ 5.28 (s, 1H), 4.52 (d, J=9.0 Hz, 1H), 4.04 (t, J=6.0 Hz, 2H), 2.82-2.73 (m, 1H), 2.69-2.56 (m, 2H), 2.36 (td, J=12.0, 3.0 Hz, 1H), 2.04 (s, 3H), 2.03 (m, 1H), 1.92-1.82 (m, 1H), 1.75-1.19 (m, 19H), 1.09-0.99 (m, 1H), 0.95 (d, J=6.0 Hz, 3H), 0.92 (d, J=6.0 Hz, 3H); HRMS (FAB) m/z calcd for C$_{23}$H$_{38}$O$_6$S (M+H$^+$) 443.2467. found 443.2462.

AMJ-Art-10α-S(CH$_2$)$_3$OC(O)t-Bu (3n)

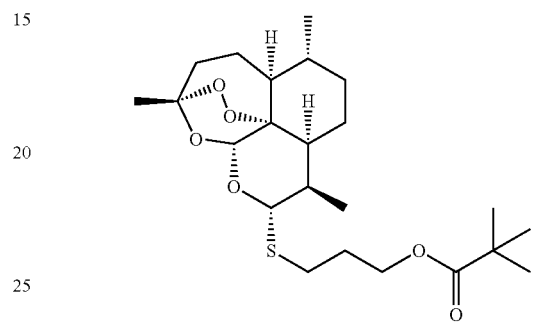

Followed the same procedure for the preparation of acetate 3l to produce titled compound 3n as a white amorphous solid (11.2 mg, 91% yield). $^1$H NMR (400 MHz, CDCl$_3$) δ 5.27 (s, 1H), 4.52 (d, J=10.8 Hz, 1H), 4.16 (t, J=6.4 Hz, 2H), 2.89-2.81 (m, 1H), 2.72-2.58 (m, 2H), 2.35 (td, J=14.0, 4.0 Hz, 1H), 2.10-1.97 (m, 3H), 1.91-1.83 (m, 1H), 1.74-1.68 (m, 2H), 1.62-1.55 (m, 2H), 1.51-1.21 (m, 8H), 1.19 (s, 9H), 1.08-0.99 (m, 1H), 0.93 (dd, J=12.8, 7.2 Hz, 6H). $^{13}$C NMR (100 MHz, CDCl$_3$) δ 178.5, 104.3, 92.2, 80.5, 80.4, 63.2, 51.8, 45.9, 38.8, 37.3, 36.2, 34.1, 31.6, 29.2, 27.5, 27.2, 27.1, 26.9, 25.9, 24.8, 21.3, 20.2, 15.0. HRMS (FAB) m/z calcd for 443.2467 [M+H$^+$]. found 443.2460.

AMJ-Art-10α-S(CH$_2$)$_3$OC(O)PhF-3 (3o)

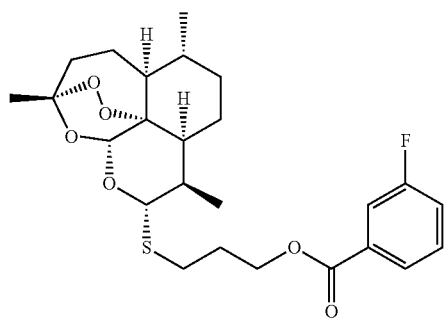

Followed the same procedure for the preparation of acetate 3l to produce titled compound 3o as a white amorphous solid (11.0 mg, 82% yield). $^1$H NMR (300 MHz, CDCl$_3$) δ 7.86-7.84 (m, 1H), 7.76 (m, 1H), 7.43 (m, 1H), 7.26-7.21 (m, 1H), 5.27 (s, 1H), 4.54 (d, J=10.8 Hz, 1H), 4.45 (t, J=6.4 Hz), 2.99-2.94 (m, 1H), 2.82-2.75 (m, 1H), 2.65-2.60 (m, 1H), 2.36 (td, J=14.0, 4.0 Hz, 1H), 2.22-2.13 (m, 2H), 2.02-1.97 (m, 1H), 1.89-1.85 (m, 1H), 1.74-1.68 (m, 2H), 1.62-1.57 (m, 2H), 1.47-1.43 (m, 1H), 1.39-1.22

(m, 6H), 1.06-1.00 (m, 1H), 0.94 (dd, J=7.6, 6.4 Hz, 6H). $^{13}$C NMR (75 MHz, CDCl$_3$) δ 165.4, 162.5 (d, J$_{C-F}$=245.5 Hz), 132.6, 129.9 (d, J$_{C-F}$=7.6 Hz), 125.4 (d, J$_{C-F}$=3.1 Hz), 119.9 (d, J$_{C-F}$=21.2 Hz), 116.5 (d, J$_{C-F}$=22.9 Hz), 104.3, 92.2, 80.6, 80.4, 64.2, 51.7, 45.9, 37.4, 36.2, 34.0, 31.6, 29.2, 25.9, 24.9, 24.7, 21.3, 20.2, 15.0.

AMJ-Art-10α-S(CH$_2$)$_3$OC(O)CH$_3$ (3p)

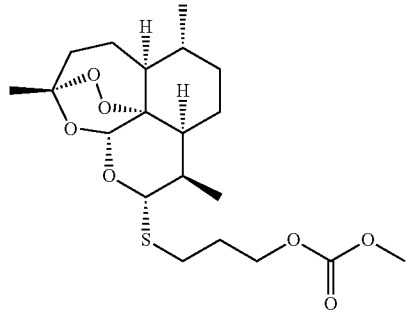

An oven-dried, 2 dram vial, equipped with a magnetic stir bar, under argon was charged with artemisinin thioacetal 3a (10 mg, 0.028 mmol, 1.0 equiv) and acetonitrile (1.5 mL). Sodium hydride (95%, 0.42 mmol, 1.0 mg, 1.5 equiv) was added and the mixture was allowed to stir for 15 min. After 15 min methyl chloroformate (4.0 mg, 0.42 mmol, 1.5 equiv) was added and the reaction was allowed to stir under argon for 24 hr. After 24 hr the reaction was quenched with water (5 mL) and extracted with dichloromethane (3×10 mL). The organic layers were combined, dried over MgSO$_4$, and concentrated on a rotary evaporator at room temperature. The crude amorphous solid was purified via column chromatography (10% ethyl acetate in hexanes) to afford the desired product 3p as a white amorphous solid (10.1 mg, 87% yield). $^1$H NMR (300 MHz, CDCl$_3$) δ 5.26 (s, 1H), 4.52 (d, J=10.8 Hz, 1H), 4.31-4.23 (m, 2H), 3.76 (s, 3H), 2.92-2.83 (m, 1H), 2.75-2.53 (m, 2H), 2.41-2.29 (m, 1H), 2.10-1.96 (m, 3H), 1.92-1.82 (m, 1H), 1.75-1.64 (m, 2H), 1.64-1.18 (m, 10H), 1.09-0.98 (m, 1H), 0.96-0.89 (m, 6H). $^{13}$C NMR (75 MHz, CDCl$_3$) δ 155.8, 104.3, 92.2, 80.6, 80.4, 66.8, 54.7, 51.7, 45.9, 37.3, 36.2, 34.1, 31.6, 29.1, 25.9, 24.8, 24.7, 21.3, 20.3, 15.0.

Art-10α-S(CH$_2$)$_6$OC(O)OCH$_3$ (3q)

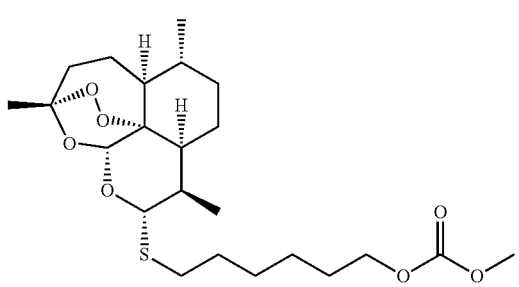

Followed the same procedure for the formation of carbonate 3p, replacing 3a with 3b, to produce the titled compound 3q as a white solid (25.5 mg, 82% yield). The reaction required extended reaction time (36 h) and two additional portions of sodium hydride and methyl chloroformate for full consumption of starting material 3b, evident by TLC analysis. $^1$H NMR (300 MHz, CDCl$_3$) δ 5.27 (s, 1H), 4.51 (d, J=12.0 Hz, 1H), 4.12 (t, J=6.0 Hz, 2H), 3.77 (s, 3H), 2.82-2.73 (m, 1H), 2.68-2.54 (m, 2H), 2.41-2.30 (m, 1H), 2.04-1.96 (m, 1H), 1.90-1.82 (m, 1H), 1.74-1.53 (m, 8H), 1.49-1.18 (m, 12H), 1.08-0.98 (m, 1H), 0.96-0.90 (m, 6H).

Art-10α-S(CH$_2$)$_3$OC(O)N(Et)$_2$ (3r)

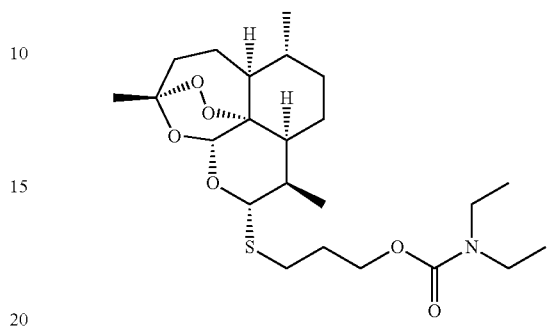

An oven-dried, 2 dram vial, equipped with a magnetic stir bar, under argon was charged with artemisinin thioacetal 3a (10 mg, 0.028 mmol, 1.0 equiv) and acetonitrile (1.5 mL). Sodium hydride (95%, 0.42 mmol, 1.0 mg, 1.5 equiv) was added and the mixture was allowed to stir for 15 min. After 15 min the desired carbamoyl chloride (0.42 mmol, 1.5 equiv) was added and the reaction was allowed to stir under argon for 24 hr. After 24 hr the reaction was quenched with water (5 mL) and extracted with dichloromethane (3×10 mL). The organic layers were combined, dried over MgSO$_4$, and concentrated on a rotary evaporator at room temperature. The crude amorphous solid was purified via column chromatography (10% ethyl acetate in hexanes) to afford the desired product 3r as a white amorphous solid (9.9 mg, 77% yield). [α]$_D^{23.4}$+7.01 (c. 0.52, CHCl$_3$). IR (thin film) 3445, 2926, 2871, 2363, 1716, 1586, 1446, 1378, 1279, cm$^{-1}$. $^1$H NMR (400 MHz, CDCl$_3$) δ 5.29 (s, 1H), 4.52 (d, J=10.8 Hz, 1H), 4.17 (t, J=6.0 Hz, 2H), 3.26 (br s, 3.26, 4H), 2.89-2.82 (m, 1H), 2.76-2.68 (m, 1H), 2.64-2.58 (m, 1H), 2.39-2.31 (m, 1H), 2.09-1.97 (m, 4H), 1.91-1.83 (m, 1H), 1.76-1.67 (m, 3H), 1.62-1.56 (m, 1H), 1.53-1.44 (m, 1H), 1.40-1.39 (m, 1H), 1.39 (s, 3H), 1.37-1.25 (m, 4H), 1.10 (t, J=6.8 Hz, 6H), 1.03-0.99 (m, 1H), 0.93 (dd, J=11.2, 6.0 Hz, 6H). $^{13}$C NMR (100 MHz, CDCl$_3$) δ 155.9, 104.3, 92.2, 80.5, 80.4, 63.9, 51.8, 46.0, 37.4, 36.2, 34.1, 31.6, 29.7, 25.9, 25.0, 24.7, 21.3, 20.2, 15.0. HRMS (FAB) m/z calcd for 458.2576 [M+H$^+$]. found 458.2573.

Art-10α-S(CH$_2$)$_6$OC(O)N(CH$_2$CH$_3$)$_2$ (3s)

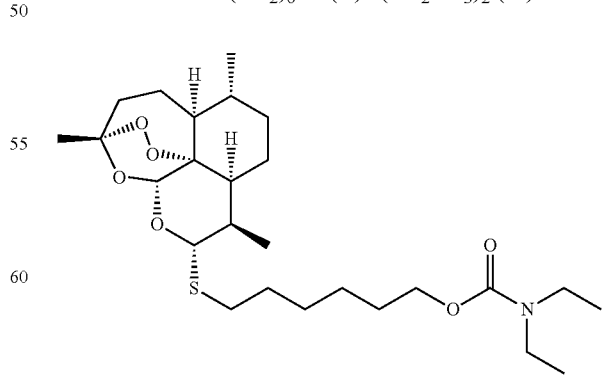

Followed the same procedure for the preparation of carbamate 3r, replacing 3a with 3b, to produce the titled compound 3s as a clear oil (17 mg, 76% yield). The reaction required extended reaction time (36 h) and two additional portions of sodium hydride and methyl carbamoyl chloride for full consumption of starting material 3b, evident by TLC analysis. $[\alpha]_D^{23.4}$+3.8 (c. 0.34, CHCl$_3$); IR (thin film) ν 2931, 2872, 1698, 1426, 1378, 1274, 1228, 1174, 1129, 1070, 1038, 929, 901, 880, 830, 771 cm$^{-1}$; $^1$H NMR (300 MHz, CDCl$_3$) δ 5.28 (s, 1H), 4.52 (d, J=12.0 Hz, 1H), 4.05 (t, J=6.0 Hz, 2H), 3.26 (br s, 4H), 2.82-2.75 (m, 1H), 2.73-2.56 (m, 2H), 2.37 (td, J=12.0, 4.0 Hz, 1H), 2.05-1.98 (m, 1H), 1.92-1.83 (m, 1H), 1.74-1.19 (m, 22H), 1.11 (t, J=6.0 Hz, 6H), 1.06-0.99 (m, 1H), 0.95 (d, J=6.0 Hz, 3H), 0.92 (d, J=6.0 Hz, 3H); $^{13}$C NMR (75 MHz, CDCl$_3$) δ 156.2, 104.3, 92.3, 80.6, 80.4, 65.0, 51.8, 46.1, 37.4, 36.3, 34.1, 31.7, 29.8, 29.0, 28.8, 28.2, 26.0, 25.7, 24.8, 21.3, 20.3, 15.1; HRMS (FAB) m/z calcd for C$_{26}$H$_{45}$NO$_6$S (M+H$^+$) 500.3046. found 500.3036.

Followed the same procedure for the preparation of carbamate 3r to produce the titled compound 3u as a white amorphous solid (11.1 mg, 82% yield). $[\alpha]_D^{22.7}$+2.44 (c. 0.39, CHCl$_3$). IR (thin film) 3398, 2928, 2872, 2360, 2340, 1689, 1437, 1375, 1309, 1290, 1221, 1194, 1152, 1130, 1037, 928, 879 cm$^{-1}$. $^1$H NMR (300 MHz, CDCl$_3$) δ 5.26 (s, 1H), 4.53 (d, J=10.8 Hz, 1H), 4.18 (t, J=6.3 Hz, 2H), 2.92-2.83 (m, 1H), 2.77-2.65 (m, 1H), 2.53-2.45 (m, 1H), 2.41-2.29 (m, 1H), 2.11-1.96 (m, 3H), 1.92-1.84 (m, 1H), 1.74-1.68 (m, 2H), 1.62-1.53 (m, 2H), 1.49-1.41 (m, 1H), 1.39 (s, 3H), 1.38-1.22 (m, 3H), 1.12 (s, 6H), 1.18 (2, 6H), 1.09-0.99 (m, 1H), 0.93 (dd, J=8.4, 6.3 Hz, 6H). $^{13}$C NMR (75 MHz, CDCl$_3$) δ 155.7, 104.3, 92.3, 80.5, 80.4, 63.6, 51.8, 46.0, 37.4, 36.2, 34.1, 31.7, 29.7, 25.9, 25.3, 24.7, 21.3, 20.3, 15.0. HRMS (FAB) m/z calcd for 486.2889 [M+H]. found 486.2884.

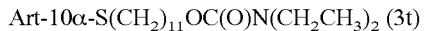

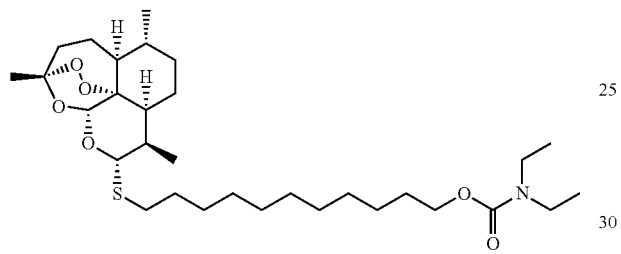

Followed the same procedure for the preparation of carbamate 3r, replacing 3a with 3c, to produce the titled compound 3t as a cloudy oil (17 mg, 68%). The reaction required extended reaction time (36 h) and two additional portions of sodium hydride and carbamoyl chloride for full consumption of starting material 3c, evident by TLC analysis. $[\alpha]_D^{22.1}$+2.3 (c. 0.34, CHCl$_3$); IR (thin film) ν 2926, 2854, 1700, 1426, 1378, 1274, 1173, 1129, 1038, 929, 880 cm$^{-1}$; $^1$H NMR (300 MHz, CDCl$_3$) δ 5.28 (s, 1H), 4.52 (d, J=9.0 Hz, 1H), 4.05 (t, J=6.0 Hz, 2H), 3.26 (br s, 4H), 2.81-2.72 (m, 1H), 2.69-2.53 (m, 2H), 2.36 (td, J=12.0, 3.0 Hz, 1H), 2.05-1.97 (m, 1H), 1.92-1.82 (m, 1H), 1.75-1.19 (m, 30H), 1.11 (t, J=6.0 Hz, 6H), 1.05-0.99 (m, 1H), 0.95 (d, J=6.0 Hz, 3H), 0.92 (d, J=6.0 Hz, 3H); $^{13}$C NMR (75 MHz, CDCl$_3$) δ 156.2, 104.3, 92.3, 80.6, 80.4, 65.1, 51.8, 46.1, 41.6, 41.3, 37.4, 36.3, 34.1, 31.7, 29.9, 29.5, 29.3, 29.1, 28.3, 26.0, 26.0, 24.8, 21.3, 20.3, 15.1, 14.0, 13.8; HRMS (FAB) m/z calcd for C$_{31}$H$_{55}$NO$_6$S (M+H$^+$) 570.3828. found 570.3814.

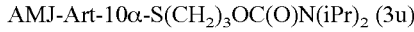

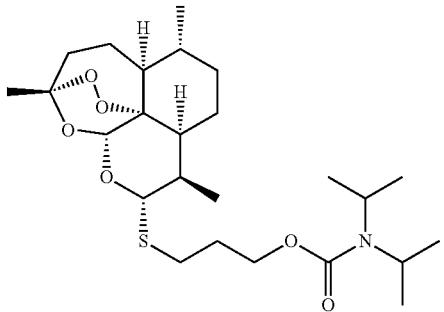

An oven-dried, 2 dram vial, equipped with a magnetic stir bar, under argon was charged with dihydroartemisinin (2a, 100 mg, 0.35 mmol, 1.0 equiv) and anhydrous dichloromethane (4 mL). 3-Mercaptopropionic acid (40 mg, 0.39 mmol, 1.1 equiv) was added and allowed to stir for 10 min at 50° C., under argon. Boron trifluoride etherate (49.6 μL, 0.35 mmol, 1.0 equiv) was added dropwise and the reaction was allowed to stir under argon at 0° C. for 30 min. After 30 min, the reaction was quenched with water (5 mL), extracted with dichloromethane (3×10 mL). The organic layers were combined, dried over MgSO$_4$, filtered, and concentrated on a rotary evaporator at room temperature. The $^1$H NMR of the crude reaction mixture indicated a mixture of 10-α and 10-β diastereomers in a ratio of 6:1 (α:β). The crude amorphous solid was purified via column chromatography (10% ethyl acetate in hexanes) to afford the desired product as an amorphous solid (96 mg, 73% yield). $[\alpha]_D^{22.6}$+26.08 (c 1.1, CHCl$_3$). IR (thin film) 2926, 2872, 1707, 1449, 1378, 1268, 1230, 1195, 1128, 1086, 1069, 1036, 959, 928, 900, 879 cm$^{-1}$. $^1$H NMR (400 MHz, CDCl$_3$) δ 5.28 (s, 1H), 4.55 (d, J=10.8 Hz, 1H), 3.09-3.01 (m, 1H), 2.92-2.79 (m, 4H), 2.78-2.69 (m, 1H), 2.67-2.58 (m, 1H), 2.40-2.29 (m, 1H), 2.07-1.97 (m, 2H), 1.91-1.82 (m, 2H), 1.78-1.68 (m, 3H), 1.62-1.54 (m, 2H), 1.52-1.43 (m, 1H), 1.40 (s, 6H), 1.39-1.18 (m, 4H), 1.09-1.01 (m, 1H), 0.93 (dd, J=12.4, 6.4 Hz, 6H). $^{13}$C NMR (100 MHz, CDCl$_3$) δ 177.5, 104.5, 92.2, 80.8, 80.4, 51.7, 45.9, 37.4, 36.2, 35.5, 34.0, 31.3, 25.8, 24.7, 23.4, 21.2, 20.2, 14.9. HRMS (FAB) m/z calcd 373.1685 [M+H$^+$]. found 373.1669.

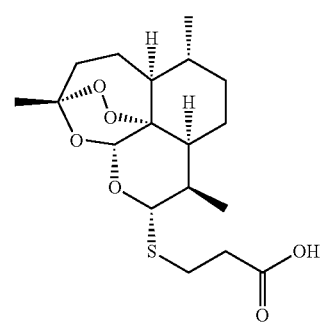

Art-10α-S(CH$_2$)$_5$C(O)OH (4b)

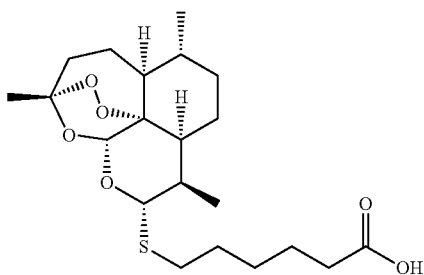

To a flame dried 25 mL round bottom flask equipped with a magnetic stir bar was added DHA (2a, 44.0 mg, 0.15 mmol, 1 equiv.) and dissolved in anhydrous toluene toluene (8 mL) under an Ar blanket. Commercially available 6-mercaptohexanoic acid (Aldrich, 23.5 μL, 0.17 mmol, 1.1 equiv.) was added and the solution was stirred for 5 min. Boron trifluoride diethyl etherate (21.0 μL, 0.17 mmol, 1.1 equiv.) was added dropwise over 5 min, and the reaction was stirred for an additional 5 min at room temperature. The resulting pink solution was quenched with saturated NH$_4$Cl (10 mL) and stirred until the pink color dissipated. The resulting mixture was extracted with Et$_2$O (3×4 mL), and the combined organic extracts were washed with brine, dried with MgSO$_4$, and concentrated in vacuo. The crude oil was purified by column chromatography (silica gel, 20-50% EtOAc/Hexanes) to afford C10-thioacetal carboxylic acid 4b as a colorless oil (41.3 mg, 66% yield). $^1$H NMR (400 MHz, CDCl$_3$) δ 10.35 (bs, 1H), 5.28 (s, 1H), 4.51 (d, J=10.8 Hz, 1H), 2.78 (m, 1H), 2.63 (m, 3H), 2.33 (m, 4H), 2.00 (m, 1H), 1.99 (m, 2H), 1.65 (m, 8H), 1.47-1.13 (m, 5H), 1.40 (s, 3H), 1.14-0.90 (m, 4H), 1.10 (d, J=6.9 Hz, 3H), 0.94 (d, J=4.4 Hz, 3H). $^{13}$C NMR (100 MHz, CDCl$_3$) δ 179.4, 104.2, 92.2, 80.5, 80.4, 76.5, 51.7 46.0, 37.3, 36.2, 34.0, 33.8, 31.6, 29.5, 28.3, 28.1, 25.9, 24.7, 24.2, 21.2, 20.2, 15.0.

Art-10α-S(CH$_2$)$_2$C(O)OCH$_3$ (4d)

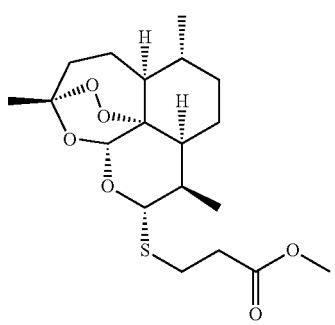

An oven-dried, 2 dram vial, equipped with a magnetic stir bar, under argon was charged with artemisinin thioacetal 4a (10 mg, 0.027 mmol, 1.0 equiv), dichloromethane (1 mL), the desired alcohol (2.0 equiv), 4-dimethylaminopyridine (DMAP) (3.0 mg, 0.21 mmol, 0.8 equiv) and the vial was cooled in an ice-water bath to 0° C. After 10 min of stirring, 1-Ethyl-3-(3-dimethylaminopropyl) carbodiimide (EDC) (6.0 mg, 0.029 mmol, 1.1 equiv) was added and the reaction was allowed to stir for 8 h. The reaction was quenched with water (2 mL), extracted with dichloromethane (3×10 mL), dried over MgSO$_4$, filtered, and concentrated on a rotary evaporator at room temperature. The crude amorphous solids were purified via preparative TLC (10% ethyl acetate in hexanes) to afford the desired products 4d as a white amorphous solid (9.1 mg, 84% yield). $^1$H NMR (400 MHz, CDCl$_3$) δ 5.27 (s, 1H), 4.55 (d, J=10.8 Hz, 1H), 3.68 (s, 3H), 3.08-3.00 (m, 1H), 2.92-2.77 (m, 3H), 2.64-2.58 (m, 1H), 2.36 (td, J=14.0, 4.0 Hz, 1H), 2.04-1.98 (m, 1H), 1.89-1.85 (m, 1H), 1.74-1.69 (m, 2H), 1.62-1.57 (m, 2H), 1.49-1.23 (m, 8H, 1.04-1.00 (m, 1H), 0.95 (d, J=6.4 Hz, 3H), 0.91 (d, J=7.2 Hz, 6H). $^{13}$C NMR (100 MHz, CDCl$_3$) δ 172.8, 104.3, 92.1, 80.8, 80.4, 51.7, 51.6, 45.9, 37.4, 36.2, 35.3, 34.1, 31.4, 25.9, 24.7, 23.6, 21.3, 20.2, 14.9.

Art-10α-S(CH$_2$)$_2$C(O)Ot-Bu (4f)

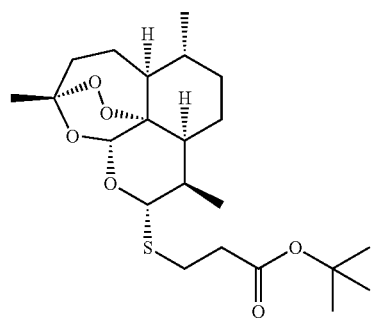

Followed the same procedure for the formation of 4d to produce the titled compound 4f as a white amorphous solid (9.4 mg, 81% yield). $^1$H NMR (400 MHz, CDCl$_3$) δ 5.28 (s, 1H), 4.55 (d, J=10.8 Hz, 1H), 3.04-2.95 (m, 1H), 2.91-2.79 (m, 1H), 2.78-2.68 (m, 1H), 2.65-2.54 (m, 2H), 2.41-2.30 (m, 1H), 2.05-1.97 (m, 1H), 1.92-1.82 (m, 1H), 1.75-1.66 (m, 2H), 1.62-1.55 (m, 2H), 1.51-1.19 (m, 18H), 1.09-1.00 (m, 1H), 0.93 (dd, J=14.0, 5.2 Hz, 6H). $^{13}$C NMR (100 MHz, CDCl$_3$) δ 171.6, 104.3, 92.2, 80.6, 80.5, 80.4, 51.8, 46.0, 37.4, 36.5, 36.2, 34.1, 31.5, 28.1, 25.9, 24.8, 23.7, 21.3, 20.3, 15.0. HRMS (FAB) m/z calcd for 429.23109 [M+H$^+$]. found 429.23108.

Art-10α-S(CH$_2$)$_2$C(O)OPhF-3 (4g)

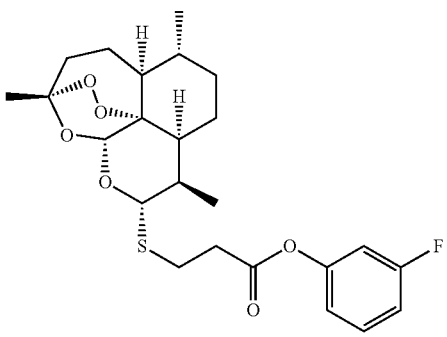

Followed the same procedure for the formation of 4d to produce the titled compound 4g as a white amorphous solid (11.1 mg, 88% yield). $^1$H NMR (400 MHz, CDCl$_3$) δ 7.37-7.31 (m, 1H), 6.99-6.87 (m, 3H), 5.29 (s, 1H), 4.60 (d, J=10.8 Hz, 1H), 3.19-3.11 (m, 2H), 3.07-2.95 (m, 2H), 2.68-2.65 (m, 1H), 2.40-2.33 (m, 1H), 2.05-2.00 (m, 1H), 1.91-1.86 (m, 1H), 1.75-1.65 (m, 1H), 1.49-1.25 (m, 8H), 1.05-1.01 (m, 1H), 0.95 (dd, J=14.0, 6.4 Hz, 6H).

Art-10α-S(CH₂)₂C(O)NHPhSCH₃-3 (4h)

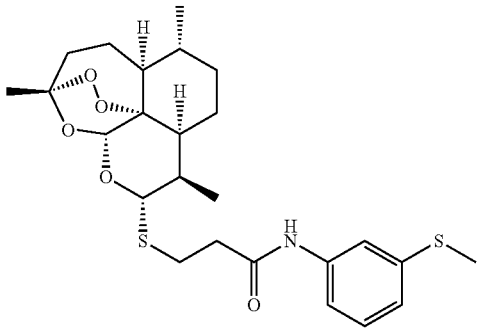

An oven-dried, 2 dram vial, equipped with a magnetic stir bar, under argon was charged with artemisinin thioacetal 4a (7 mg, 0.019 mmol, 1.0 equiv) and dichloromethane (2 mL). 1-Ethyl-3-(3-dimethylaminopropyl) carbodiimide (EDC) (4 mg, 0.021 mmol, 1.1 equiv), 1-hydroxybenzotriazole (HOBt) (3 mg, 0.021 mmol, 1.1 equiv), dichloromethane (2 mL), and stirred at room temperature for 1 hr, under argon. After 1 h, the desired aniline (0.028 mmol, 1.5 equiv) was added and the reaction was allowed to stir overnight. The reaction was quenched with saturated ammonium chloride (2 mL), extracted with dichloromethane (3×10 mL), dried over MgSO₄, filtered, and concentrated on a rotary evaporator at room temperature. The crude amorphous solids were purified via preparative TLC (15% ethyl acetate in hexanes) to afford the desired product 4h as a white amorphous solid (7.5 mg, 80% yield). $[\alpha]_D^{21.8}$ –83.48 (c. 1.46, CHCl₃). IR (thin film) 3320, 2924, 2871, 1689, 1585, 1538, 1480, 1447, 1419, 1378, 1300, 1270, 1236, 1194, 1154, 1125, 1084, 1033, 1014, 978, 927, 900, 878 cm⁻¹. ¹H NMR (300 MHz, CDCl₃) δ 9.01 (br s, 1H), 7.74 (d, J=1.8 Hz, 1H), 7.44 (d, J=8.1 Hz, 1H), 7.28-7.18 (m, 1H), 6.96 (d, J=7.8 Hz, 1H), 5.44 (s, 1H), 4.63 (d, J=10.8 Hz, 1H), 3.27-3.16 (m, 2H), 2.89-2.68 (m, 3H), 2.49 (s, 3H), 2.48-2.34 (m, 1H), 2.10-2.01 (m, 1H), 1.99-1.89 (m, 1H), 1.82-1.66 (m, 3H), 1.58-1.39 (m, 1H), 1.35 (s, 6H), 1.34-1.24 (m, 1H), 1.14-1.05 (m, 1H), 1.01-0.96 (m, 6H). ¹³C NMR (75 MHz, CDCl₃) δ 171.0, 139.2, 139.0, 128.9, 121.7, 117.1, 116.1, 104.9, 92.5, 81.1, 80.7, 51.6, 45.8, 38.4, 37.5, 36.3, 33.9, 30.2, 25.7, 25.6, 24.7, 21.3, 20.2, 15.7, 14.9. HRMS (FAB) m/z calcd for 494.2035 [M+H⁺]. found 494.2015.

Art-10α-S(CH₂)₂C(O)NHPhF-4 (4i)

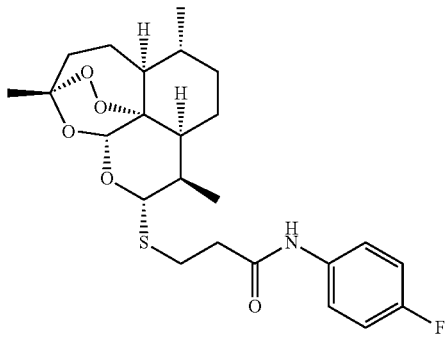

Followed the same procedure for the formation of 4h to produce the titled compound 4i as a white amorphous solid (7.3 mg, 83% yield). $[\alpha]_D^{21.0}$ –117.46 (c. 0.96, CHCl₃). IR (thin film) 3322, 3154, 3070, 2927, 2872, 1686, 1614, 1547, 1508, 1449, 1406, 1378, 1351, 1306, 1270, 1211, 1195, 1155, 1126, 1097, 1084, 1069, 1034, 1015, 978, 959, 928, 900, 878 cm⁻¹. ¹H NMR (300 MHz, CDCl₃) δ 8.97 (br s, 1H), 7.68-7.61 (m, 2H), 7.04-6.91 (m, 2H), 5.43 (s, 1H), 4.62 (d, J=10.8 Hz, 1H), 3.24-3.11 (m, 2H), 2.88-2.68 (m, 3H), 2.44-2.32 (m, 1H), 2.09-1.99 (m, 1H), 1.99-1.88 (m, 1H), 1.81-1.65 (m, 4H), 1.53-1.33 (m, 2H), 1.32 (s, 6H), 1.13-1.02 (m, 1H), 0.98 (dd, J=6.9, 5.2 Hz, 6H). ¹³C NMR (75 MHz, CDCl₃) δ 170.8, 158.9 (d, $J_{C\text{-}F}$=240.4 Hz), 134.7 (d, $J_{C\text{-}F}$=2.8 Hz), 121.1 (d, $J_{C\text{-}F}$=7.7 Hz), 115.2 (d, $J_{C\text{-}F}$=22.1 Hz), 104.9, 92.5, 81.1, 80.7, 51.6, 45.8, 38.2, 37.5, 36.3, 33.9, 30.2, 25.8, 25.6, 24.7, 21.3, 20.2, 14.9. HRMS (FAB) m/z calcd for 466.2064 [M+H⁺]. found 466.2059.

Art-10α-S(CH₂)₃OC(O)(CH₂)₂S-10α-Art (5a)

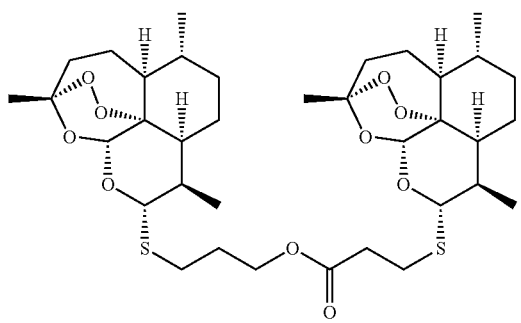

An oven-dried, 2 dram vial, equipped with a magnetic stir bar, under argon was charged with desired artemisinin thioacetal carboxylic acid (4a) (9.7 mg, 0.026 mmol, 1.0 equiv), dichloromethane (1 mL), the desired artemisinin thioacetal alcohol (3a) (10.4 mg, 0.029 mmol, 1.1 equiv), 4-dimethylaminopyridine (DMAP) (0.021 mmol, 0.8 equiv) and the vial was cooled in an ice-water bath to 0° C. After 10 min of stirring, 1-Ethyl-3-(3-dimethylaminopropyl) carbodiimide (EDC) (0.029 mmol, 1.1 equiv) was added and the reaction was allowed to stir overnight. The reaction was quenched with water (2 mL), extracted with dichloromethane (3×10 mL), dried over MgSO₄, filtered, and concentrated on a rotary evaporator at room temperature. The crude amorphous solids were purified via preparative TLC (10% ethyl acetate in hexanes) to afford the desired product 5a as a white amorphous solid (17.7 mg, 95% yield). ¹H NMR (300 MHz, CDCl₃) δ 5.27 (s, 2H), 4.53 (ap t, J=9.9 Hz, 2H), 4.21 (t, J=6.0 Hz, 2H), 3.09-2.97 (m, 1H), 2.92-2.52 (m, 8H), 3.36 (td, J=13.8, 3.6 Hz, 2H), 2.09-1.94 (m, 4H), 1.92-1.81 (m, 2H), 1.78-1.65 (m, 4H), 1.63-1.15 (m, 19H), 1.11-1.00 (m, 2H), 0.93 (dd, J=10.2, 6.0 Hz, 12H). ¹³C NMR (75 MHz, CDCl₃) δ 172.3, 104.3, 104.2, 92.2, 92.1, 80.7, 80.6, 80.4, 63.4, 51.8, 46.0, 37.4, 36.2, 35.5, 34.1, 31.6, 31.5, 29.2, 26.0, 25.9, 24.9, 24.8, 23.6, 21.3, 20.2, 15.0, 14.9.

Art-10α-S(CH₂)₆OC(O)(CH₂)₂S-10α-Art (5c)

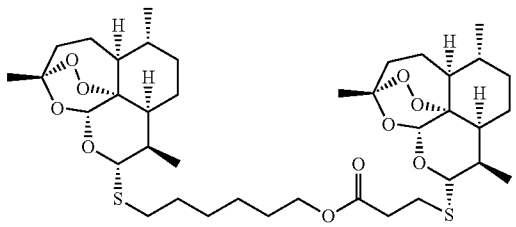

Followed the same procedure for the formation of ester dimer 5a, replacing 3a with 3b, to produce the titled compound 5c as a clear oil (19.0 mg, 82% yield). ¹H NMR (400 MHz, CDCl₃) δ 5.27 (s, 2H), 4.54 (d, J=12.0 Hz, 1H), 4.51 (d, J=12.0 Hz, 1H), 4.08 (t, J=8.0 Hz, 2H), 3.06-2.99 (m, 1H), 2.91-2.55 (m, 8H), 2.36 (td, J=12.0, 4.0 Hz, 2H), 2.03-1.98 (m, 2H), 1.90-1.83 (m, 2H), 1.72-1.55 (m, 12H), 1.51-1.20 (m, 20H), 1.07-1.00 (m, 2H), 0.95 (d, J=8.0 Hz, 6H), 0.91 (d, J=8.0 Hz, 3H), 0.90 (d, J=8.0 Hz, 3H).

Art-10α-S(CH₂)₂OH (101)

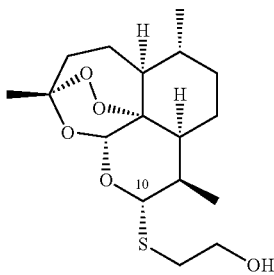

An oven-dried, 2-dram vial, equipped with a magnetic stir bar, under argon was charged with dihydroartemisinin (2a, 100 mg, 0.35 mmol, 1.0 equiv) and anhydrous dichloromethane (4 mL). 2-Mercaptopropanol (41 mg, 0.53 mmol, 1.5 equiv) was added and allowed to stir for 10 min at room temperature, under argon. Boron trifluoride diethyl etherate (50 mg, 0.35 mmol, 1.0 equiv) was added dropwise and the reaction was allowed to stir under argon at room temperature for 30 min. After 30 min, the reaction was quenched with water (5 mL) and extracted with dichloromethane (3×10 mL). The organic layers were combined, dried over MgSO₄, and concentrated on a rotary evaporator at room temperature. The ¹H NMR of the crude reaction mixture indicated a mixture of C-10α and C-10β diastereomers in a ratio of 5:1 (C-10α:C10-β). The stereochemistry at the C-10 carbon was determined by comparison to published ¹H NMR coupling constants between α ($J_{C9}$-$J_{C10}$, J=11.0 Hz) and β ($J_{C9}$-$J_{C10}$, J=5.3 Hz). The crude amorphous solid was purified via column chromatography (5-10% ethyl acetate in hexanes) to afford C-10α thioacetal alcohol 101 as a white amorphous solid (84.7 mg, 69% yield). $[\alpha]_D^{24.1}$+37.53 (c. 0.43, CHCl₃); IR (thin film) ν 3478, 3449, 3385, 2953, 2924, 2871, 1667, 1449, 1378, 1276, 1231, 1199, 1127, 1089, 1077, 1036, 1011, 928, 877, 827, 753 cm⁻¹; ¹H NMR (300 MHz, CDCl₃) δ 5.27 (s, 1H), 4.47 (d, J=10.8 Hz, 1H), 3.93-3.58 (m, 3H), 3.03-2.87 (m, 1H), 2.62 (dtt, J=18.0, 7.3, 3.4 Hz, 2H), 2.29 (ddd, J=14.6, 13.2, 4.0 Hz, 1H), 2.04-1.75 (m, 3H), 1.77-1.10 (m, 10H), 1.04-0.92 (m, 1H), 0.88 (t, J=6.8 Hz, 7H); ¹³C NMR (75 MHz, CDCl₃) δ 104.4, 92.4, 80.6, 80.3, 62.7, 51.7, 45.9, 37.3, 36.1, 34.0, 32.7, 31.4, 25.7, 24.7, 21.2, 20.1, 14.9; HRMS (FAB) m/z calcd for C₁₇H₂₈O₅S [M+H]⁺ 345.1736. found 345.1726.

Art-10α-S(CH₂)₄OH (102)

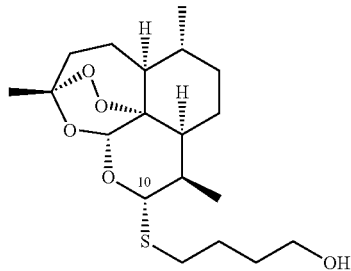

An oven-dried, 2-dram vial, equipped with a magnetic stir bar, under argon was charged with dihydroartemisinin (2a, 100 mg, 0.35 mmol, 1.0 equiv) and anhydrous dichloromethane (4 mL). 4-Mercaptopropanol (56 mg, 0.53 mmol, 1.5 equiv) was added and allowed to stir for 10 min at room temperature, under argon. Boron trifluoride diethyl etherate (50 mg, 0.35 mmol, 1.0 equiv) was added dropwise and the reaction was allowed to stir under argon at room temperature for 30 min. After 30 min, the reaction was quenched with water (5 mL) and extracted with dichloromethane (3×10 mL). The organic layers were combined, dried over MgSO₄, and concentrated on a rotary evaporator at room temperature. The ¹H NMR of the crude reaction mixture indicated a mixture of C-10α and C-10β diastereomers in a ratio of 6:1 (C-10α:C10-β). The stereochemistry at the C-10 carbon was determined by comparison to published ¹H NMR coupling constants between α ($J_{C9}$-$J_{C10}$, J=11.0 Hz) and β ($J_{C9}$-$J_{C10}$, J=5.3 Hz). The crude amorphous solid was purified via column chromatography (5-10% ethyl acetate in hexanes) to afford C-10a thioacetal alcohol 102 as a white amorphous solid (85.2 mg, 65% yield). $[\alpha]_D^{24.3}$+25.35 (c. 0.39, CHCl₃); IR (thin film) ν 3386, 2951, 2925, 2870, 1667, 1448, 1378, 1277, 1230, 1199, 1127, 1091, 1035, 1018, 928, 877, 827, 754 cm⁻¹; ¹H NMR (300 MHz, CDCl₃) δ 5.22 (s, 1H), 4.47 (d, J=10.7 Hz, 1H), 3.59 (t, J=5.9 Hz, 2H), 2.86-2.68 (m, 1H), 2.68-2.46 (m, 2H), 2.39-2.17 (m, 3H), 1.94 (ddd, J=14.5, 4.9, 2.7 Hz, 1H), 1.87-1.10 (m, 13H), 1.05-0.92 (m, 1H), 0.87 (dd, J=9.6, 6.6 Hz, 7H); ¹³C NMR (75 MHz, CDCl₃) δ 104.2, 92.2, 80.7, 80.4, 62.1, 51.7, 46.0, 37.3, 36.2, 34.0, 31.8, 31.6, 28.3, 26.1, 25.8, 25.7, 21.2, 20.2, 15.0; HRMS (FAB) m/z calcd for C₁₉H₃₂O₅S [M+H]⁺ 373.2049. found 373.2039.

Art-10α-S(CH₂)₂OC(O)N(CH₂CH₃)₂ (103)

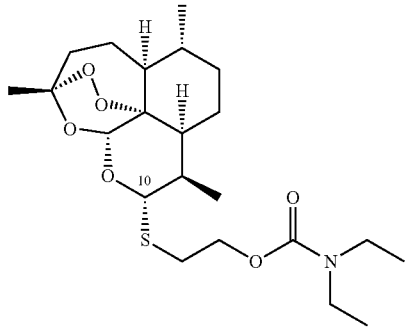

An oven-dried, 2-dram vial, equipped with a magnetic stir bar, under argon was charged with thioacetal alcohol 101 (10 mg, 0.029 mmol, 1.0 equiv) and acetonitrile (1.5 mL). Sodium hydride (95%, 0.042 mg, 1.0 mg, 1.5 equiv) was added and the mixture was allowed to stir for 15 min. After 15 min diethyl carbamoyl chloride (4.5 mg, 0.042 mmol, 1.5 equiv) was added and the reaction was allowed to stir under argon for 24 hr. After 24 hr the reaction was quenched with water (5 mL) and extracted with dichloromethane (3×10 mL). The organic layers were combined, dried over MgSO$_4$, and concentrated on a rotary evaporator at room temperature. The crude oil was purified via column chromatography (10% ethyl acetate in hexanes) to afford the desired diethyl carbamate 103 as a white amorphous solid (11.0 mg, 86% yield). $[\alpha]_D^{24.7}$ −0.84 (c. 0.54, CHCl$_3$); IR (thin film) ν 2972, 2927, 2872, 2343, 1698, 1480, 1454, 1424, 1378, 1316, 1273, 1228, 1201, 1171, 1128, 1093, 1075, 1037, 999, 928, 878, 828, 767, 746 cm$^{-1}$; $^1$H NMR (300 MHz, CDCl$_3$) δ 5.28 (s, 1H), 4.57 (d, J=10.8 Hz, 1H), 4.30 (td, J=7.1, 6.7, 1.1 Hz, 2H), 3.27 (d, J=7.4 Hz, 5H), 3.15-2.94 (m, 1H), 2.95-2.78 (m, 1H), 2.58 (ddd, J=11.1, 7.3, 4.2 Hz, 1H), 2.36 (ddd, J=14.5, 13.3, 4.0 Hz, 1H), 2.07-1.95 (m, 1H), 1.87 (dddd, J=13.4, 6.7, 4.0, 3.0 Hz, 1H), 1.78-1.17 (m, 12H), 1.17-0.87 (m, 13H); $^{13}$C NMR (75 MHz, CDCl$_3$) δ 155.7, 104.3, 92.2, 80.5, 80.3, 64.3, 51.9, 46.1, 41.5, 37.4, 36.3, 34.1, 31.9, 27.7, 25.8, 24.8, 21.3, 20.1, 14.9, 13.7; HRMS (FAB) m/z calcd for C$_{22}$H$_{37}$NO$_6$S [M+H]$^+$ 444.2420. found 444.2419.

Art-10α-S(CH$_2$)$_2$OC(O)N(iPr)$_2$ (104)

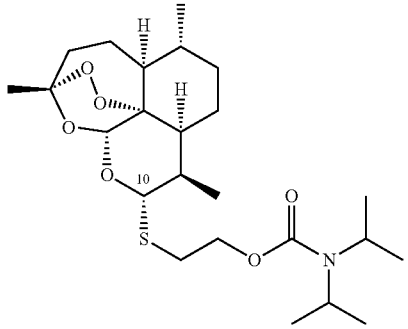

An oven-dried, 2-dram vial, equipped with a magnetic stir bar, under argon was charged with thioacetal alcohol 101 (10 mg, 0.029 mmol, 1.0 equiv) and acetonitrile (1.5 mL). Sodium hydride (95%, 0.042 mg, 1.0 mg, 1.5 equiv) was added and the mixture was allowed to stir for 15 min. After 15 min diisopropyl carbamoyl chloride (6.8 mg, 0.042 mmol, 1.5 equiv) was added and the reaction was allowed to stir under argon for 24 hr. After 24 hr the reaction was quenched with water (5 mL) and extracted with dichloromethane (3×10 mL). The organic layers were combined, dried over MgSO$_4$, and concentrated on a rotary evaporator at room temperature. The crude oil was purified via column chromatography (10% ethyl acetate in hexanes) to afford the desired diisopropyl carbamate 104 as a white amorphous solid (11.5 mg, 84% yield). $[\alpha]_D^{23.8}$+2.03 (c. 0.59, CHCl$_3$); IR (thin film) ν 2998, 2968, 2927, 2872, 2363, 1691, 1477, 1436, 1374, 1314, 1289, 1220, 1197, 1156, 1130, 1077, 1038, 928, 878, 828, 766, 749 cm$^{-1}$; $^1$H NMR (300 MHz, CDCl$_3$) δ 5.29 (d, J=3.1 Hz, 1H), 4.57 (d, J=10.8 Hz, 1H), 4.35-4.24 (m, 2H), 3.06 (ddd, J=13.1, 6.9, 6.0 Hz, 1H), 2.89 (dt, J=13.5, 7.3 Hz, 1H), 2.58 (ddd, J=11.1, 7.3, 4.2 Hz, 1H), 2.36 (ddd, J=14.5, 13.3, 4.0 Hz, 1H), 2.01 (ddd, J=14.5, 4.9, 2.9 Hz, 1H), 1.87 (dddd, J=13.4, 6.6, 4.0, 3.0 Hz, 1H), 1.79-1.11 (m, 23H), 1.11-0.98 (m, 1H), 0.93 (dd, J=11.0, 6.6 Hz, 6H); $^{13}$C NMR (75 MHz, CDCl$_3$) δ 155.4, 104.3, 92.2, 92.1, 80.3, 63.8, 51.8, 46.0, 37.4, 36.3, 34.1, 31.9, 27.6, 25.9, 24.8, 21.3, 20.2, 14.9; HRMS (FAB) m/z calcd for C$_{24}$H$_{41}$NO$_6$S [M+H]$^+$ 472.2733. found 472.2728.

Art-10α-S(CH$_2$)$_4$OC(O)N(CH$_2$CH$_3$)$_2$ (105)

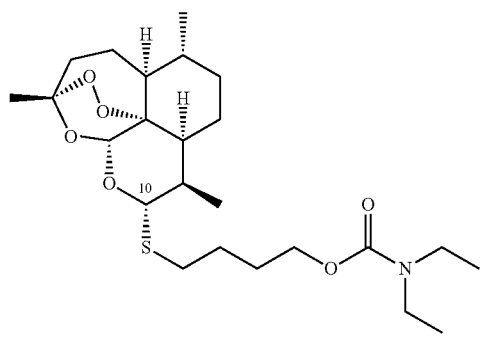

An oven-dried, 2-dram vial, equipped with a magnetic stir bar, under argon was charged with thioacetal alcohol 102 (10 mg, 0.027 mmol, 1.0 equiv) and acetonitrile (1.5 mL). Sodium hydride (95%, 0.041 mg, 1.0 mg, 1.5 equiv) was added and the mixture was allowed to stir for 15 min. After 15 min diethyl carbamoyl chloride (4.4 mg, 0.041 mmol, 1.5 equiv) was added and the reaction was allowed to stir under argon for 24 hr. After 24 hr the reaction was quenched with water (5 mL) and extracted with dichloromethane (3×10 mL). The organic layers were combined, dried over MgSO$_4$, and concentrated on a rotary evaporator at room temperature. The crude oil was purified via column chromatography (10% ethyl acetate in hexanes) to afford the desired diethyl carbamate 105 as a white amorphous solid (10.7 mg, 84% yield) $[\alpha]_D^{23.8}$+13.10 (c. 0.57, CHCl$_3$); IR (thin film) ν 2971, 2927, 2871, 2362, 2334, 1697, 1481, 1453, 1425, 1378, 1316, 1274, 1228, 1172, 1127, 1093, 1074, 1035, 979, 928, 878, 828, 759, 748 cm$^{-1}$; $^1$H NMR (300 MHz, CDCl$_3$) δ 5.27 (s, 1H), 4.52 (d, J=10.7 Hz, 1H), 4.14-4.00 (m, 2H), 3.25 (s, 4H), 2.92-2.49 (m, 2H), 2.36 (ddd, J=14.5, 13.3, 4.0 Hz, 1H), 2.01 (ddd, J=14.5, 5.0, 3.0 Hz, 1H), 1.94-1.16 (m, 15H), 1.16-0.83 (m, 14H); $^{13}$C NMR (75 MHz, CDCl$_3$) δ 156.0, 104.3, 92.3, 92.2, 80.5, 80.4, 64.6, 51.8, 46.0, 41.3, 37.4, 36.3, 34.1, 31.7, 28.5, 27.9, 26.4, 25.9, 24.7, 21.3, 20.2, 15.1, 13.9; HRMS (FAB) m/z calcd for C$_{24}$H$_{41}$NO$_6$S [M+H]$^+$ 472.2733. found 472.2722.

Art-10α-S(CH$_2$)$_4$OC(O)N(iPr)$_2$ (106)

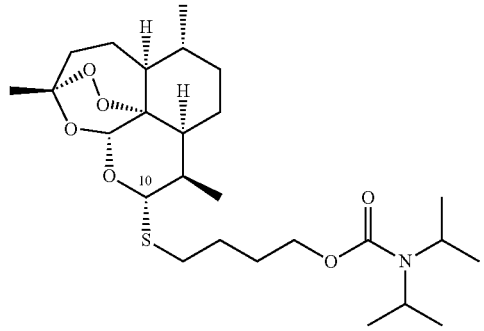

An oven-dried, 2-dram vial, equipped with a magnetic stir bar, under argon was charged with thioacetal alcohol 102 (10 mg, 0.027 mmol, 1.0 equiv) and acetonitrile (1.5 mL). Sodium hydride (95%, 0.041 mg, 1.0 mg, 1.5 equiv) was added and the mixture was allowed to stir for 15 min. After 15 min diisopropyl carbamoyl chloride (6.9 mg, 0.041 mmol, 1.5 equiv) was added and the reaction was allowed to stir under argon for 24 hr. After 24 hr the reaction was quenched with water (5 mL) and extracted with dichloromethane (3×10 mL). The organic layers were combined, dried over MgSO$_4$, and concentrated on a rotary evaporator at room temperature. The crude oil was purified via column chromatography (10% ethyl acetate in hexanes) to afford the desired diisopropyl carbamate 106 as a white amorphous solid (10.6 mg, 79% yield). $[\alpha]_D^{24.4}$+13.37 (c. 0.68, CHCl$_3$); IR (thin film) ν 2968, 2926, 2871, 1690, 1477, 1437, 1374, 1313, 1289, 1220, 1193, 1156, 1129, 1037, 928, 878, 827, 771 cm$^{-1}$; $^1$H NMR (300 MHz, CDCl$_3$) δ 5.27 (s, 1H), 4.52 (d, J=10.8 Hz, 1H), 4.17-4.02 (m, 2H), 2.91-2.51 (m, 2H), 2.36 (ddd, J=14.5, 13.3, 4.0 Hz, 1H), 2.10-1.93 (m, 1H), 1.93-1.12 (m, 27H), 1.11-0.98 (m, 1H), 0.93 (dd, J=9.4, 6.6 Hz, 7H); $^{13}$C NMR (75 MHz, CDCl$_3$) δ 155.8, 104.3, 92.3, 80.5, 80.4, 64.2, 51.8, 46.0, 37.4, 36.3, 34.1, 31.7, 28.5, 28.0, 26.6, 25.9, 24.8, 21.3, 20.2, 15.1; HRMS (FAB) m/z calcd for C$_{26}$H$_{45}$NO$_6$S [M+H]$^+$ 500.3046. found 500.3046.

Art-10α-S(CH$_2$)$_2$OC(O)SCH$_3$ (107)

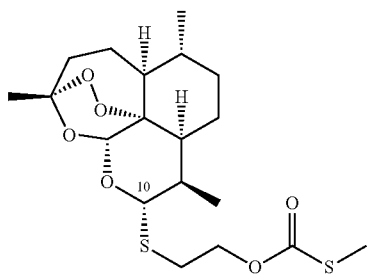

An oven-dried, 2-dram vial, equipped with a magnetic stir bar, under argon was charged with thioacetal alcohol 101 (10 mg, 0.029 mmol, 1.0 equiv) and dichloromethane (1.5 mL). Pyridine (0.042 mg, 3.0 mg, 1.5 equiv) was added and the mixture was allowed to stir for 15 min. After 15 min S-methyl chloroformate (4.6 mg, 0.042 mmol, 1.5 equiv) was added and the reaction was allowed to stir under argon for 24 hr. After 24 hr the reaction was quenched with water (5 mL) and extracted with dichloromethane (3×10 mL). The organic layers were combined, dried over MgSO$_4$, and concentrated on a rotary evaporator at room temperature. The crude oil was purified via column chromatography (10% ethyl acetate in hexanes) to afford the desired S-methyl thiocarbamate 107 as a white amorphous solid (9.3 mg, 77% yield). $[\alpha]_D^{24.7}$+10.69 (c. 0.32, CHCl$_3$); IR (thin film) ν 2927, 2871, 2363, 1709, 1450, 1378, 1276, 1200, 1150, 1133, 1036, 929, 878, 827, 754 cm$^{-1}$; $^1$H NMR (300 MHz, CDCl$_3$) δ 5.28 (s, 1H), 4.57 (d, J=10.8 Hz, 1H), 4.53-4.42 (m, 2H), 3.10 (ddd, J=14.1, 7.9, 6.3 Hz, 1H), 2.81 (ddd, J=14.1, 8.1, 6.3 Hz, 1H), 2.59 (ddd, J=11.1, 7.3, 4.2 Hz, 1H), 2.47-2.24 (m, 4H), 2.09-1.95 (m, 1H), 1.87 (dddd, J=13.4, 6.6, 4.0, 2.9 Hz, 1H), 1.79-1.66 (m, 2H), 1.66-1.17 (m, 8H), 1.12-0.98 (m, 1H), 0.93 (dd, J=10.5, 6.6 Hz, 6H); $^{13}$C NMR (75 MHz, CDCl$_3$) δ 171.3, 104.4, 92.2, 92.1, 80.5, 80.3, 67.1, 51.7, 45.9, 37.4, 36.2, 34.1, 31.7, 26.8, 25.9, 24.7, 21.3, 20.2, 14.9, 13.4; HRMS (FAB) m/z calcd for C$_{19}$H$_{30}$O$_6$S$_2$ [M+H]$^+$ 419.1562. found 419.1562.

Art-10α-S(CH$_2$)$_2$OC(O)StBu (108)

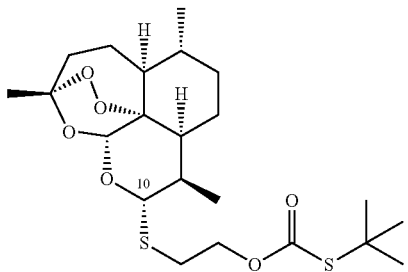

An oven-dried, 2-dram vial, equipped with a magnetic stir bar, under argon was charged with thioacetal alcohol 101 (10 mg, 0.029 mmol, 1.0 equiv) and dichloromethane (1.5 mL). Pyridine (0.042 mg, 3.0 mg, 1.5 equiv) was added and the mixture was allowed to stir for 15 min. After 15 min S-t-butyl chlorothioformate (6.4 mg, 0.042 mmol, 1.5 equiv) was added and the reaction was allowed to stir under argon for 24 hr. After 24 hr the reaction was quenched with water (5 mL) and extracted with dichloromethane (3×10 mL). The organic layers were combined, dried over MgSO$_4$, and concentrated on a rotary evaporator at room temperature. The crude oil was purified via column chromatography (10% ethyl acetate in hexanes) to afford the desired S-t-butyl thiocarbamate 108 as a white amorphous solid (10.3 mg, 77% yield). $[\alpha]_D^{23.3}$+9.56 (c. 0.69, CHCl$_3$); IR (thin film) ν 2963, 2925, 2871, 2363, 1705, 1453, 1381, 1372, 1277, 1229, 1199, 1123, 1037, 930, 878, 855, 827, 756 cm$^{-1}$; $^1$H NMR (300 MHz, CDCl$_3$) δ 5.28 (s, 1H), 4.58 (d, J=10.8 Hz, 1H), 4.42 (t, J=7.1 Hz, 2H), 3.09 (dt, J=14.0, 7.0 Hz, 1H), 2.81 (dt, J=14.1, 7.1 Hz, 1H), 2.58 (ddd, J=11.1, 7.3, 4.2 Hz, 1H), 2.36 (ddd, J=14.6, 13.3, 4.0 Hz, 1H), 2.01 (ddd, J=14.5, 4.9, 2.9 Hz, 1H), 1.87 (dddd, J=13.4, 6.7, 4.0, 3.0 Hz, 1H), 1.80-1.17 (m, 20H), 1.13-0.97 (m, 1H), 0.93 (dd, J=11.6, 6.6 Hz, 7H); $^{13}$C NMR (75 MHz, CDCl$_3$) δ 169.7, 104.3, 92.2, 92.1, 80.4, 80.3, 66.1, 51.8, 47.1, 46.0, 37.4, 36.2, 34.1, 31.8, 30.1, 26.9, 25.9, 24.8, 21.3, 20.2, 14.9; HRMS (FAB) m/z calcd for C$_{22}$H$_{36}$O$_6$S$_2$ [M+H]$^+$ 461.2032. found 461.2020.

Art-10α-S(CH$_2$)$_3$OC(O)SCH$_3$ (109)

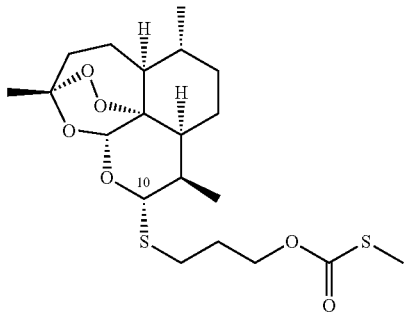

An oven-dried, 2 dram vial, equipped with a magnetic stir bar, under argon was charged with alcohol 3a (10 mg, 0.028 mmol, 1.0 equiv) and dichloromethane (1.0 mL). Pyridine (3.0 mg, 0.042 mmol, 1.5 equiv) was added and the mixture was allowed to stir for 15 min. After 15 min S-methyl chlorothioformate (4.6 mg, 0.042 mmol, 1.5 equiv) was added and the reaction was allowed to stir under argon for 24 hr. After 24 hr the reaction was quenched with water (5 mL) and extracted with dichloromethane (3×10 mL). The organic layers were combined, dried over MgSO$_4$, and concentrated on a rotary evaporator at room temperature. The crude reaction mixtures were purified via silica gel column chromatography (10% ethyl acetate in hexanes) to afford the desired S-methyl thiocarbamate 109 as a white amorphous solid (9.8 mg, 81% yield). $[\alpha]_D^{22.1}$-2.40 (c. 0.55, CHCl$_3$); IR (thin film) ν 2925, 2871, 1709, 1452, 1377, 1149, 1033, 926, 877, 826 cm$^{-1}$; $^1$H NMR (300 MHz, CDCl$_3$) δ 5.27 (s, 1H), 4.52 (d, J=10.8 Hz, 1H), 4.35 (td, J=6.3, 1.0 Hz, 2H), 2.87 (dt, J=13.6, 6.9 Hz, 1H), 2.76-2.53 (m, 2H), 2.33 (s, 4H), 2.14-1.96 (m, 3H), 1.87 (ddt, J=13.5, 6.7, 3.3 Hz, 1H), 1.77-1.65 (m, 2H), 1.64-1.21 (m, 8H), 1.11-0.98 (m, 1H), 0.93 (dd, J=9.8, 6.6 Hz, 6H); $^{13}$C NMR (75 MHz, CDCl$_3$) δ 171.7, 104.4, 92.4, 80.8, 80.5, 66.4, 51.9, 46.2, 37.5, 36.4, 34.2, 31.8, 29.3, 26.1, 24.9, 21.4, 20.4, 15.2, 13.6, 13.4; HRMS (FAB) m/z calcd for C$_{20}$H$_{32}$O$_6$S$_2$ [M+Na]$^+$ 455.1538. found 455.1532.

Art-10α-S(CH$_2$)$_3$OC(O)SnPr (110)

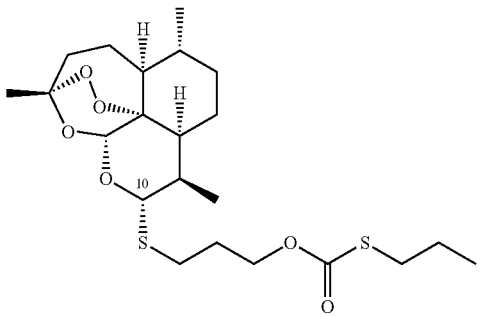

An oven-dried, 2 dram vial, equipped with a magnetic stir bar, under argon was charged with alcohol 3a (10 mg, 0.028 mmol, 1.0 equiv) and dichloromethane (1.0 mL). Pyridine (3.0 mg, 0.042 mmol, 1.5 equiv) was added and the mixture was allowed to stir for 15 min. After 15 min S-n-propyl chlorothioformate (5.9 mg, 0.042 mmol, 1.5 equiv) was added and the reaction was allowed to stir under argon for 24 hr. After 24 hr the reaction was quenched with water (5 mL) and extracted with dichloromethane (3×10 mL). The organic layers were combined, dried over MgSO$_4$, and concentrated on a rotary evaporator at room temperature. The crude reaction mixtures were purified via silica gel column chromatography (10% ethyl acetate in hexanes) to afford the desired S-methyl thiocarbamate 110 as a white amorphous solid (9.9 mg, 77% yield). $[\alpha]_D^{22.6}$-1.74 (c. 0.34, CHCl$_3$); IR (thin film) ν 2961, 2923, 2872, 1714, 1558, 1541, 1456, 1376, 1227, 1151, 1127, 1036, 927, 879, 828, 774, 736 cm$^{-1}$; $^1$H NMR (300 MHz, CDCl$_3$) δ 5.27 (s, 1H), 4.52 (d, J=10.8 Hz, 1H), 4.34 (td, J=6.3, 1.6 Hz, 2H), 2.91-2.79 (m, 3H), 2.73-2.54 (m, 2H), 2.36 (ddd, J=14.6, 13.4, 4.0 Hz, 1H), 2.12-1.96 (m, 4H), 1.92-1.83 (m, 1H), 1.76-1.54 (m, 6H), 1.40 (s, 4H), 1.08-0.88 (m, 11H); $^{13}$C NMR (75 MHz, CDCl$_3$) δ 171.4, 104.4, 92.4, 80.8, 80.5, 66.2, 51.9, 46.2, 37.5, 36.4, 34.2, 33.1, 31.8, 29.3, 26.1, 24.9, 23.3, 21.4, 20.4, 15.2, 13.4; HRMS (FAB) m/z calcd for C$_{22}$H$_{36}$O$_6$S$_2$ [M+H]$^+$ 461.2031 [M+H$^+$]. found 461.2020.

Art-10α-S(CH$_2$)$_3$OC(O)StBu (111)

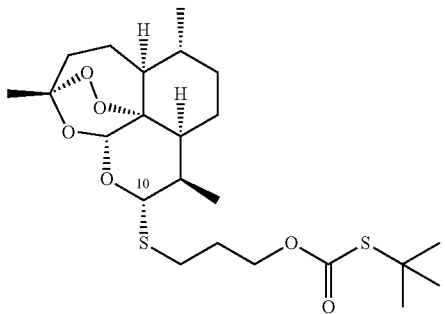

An oven-dried, 2-dram vial, equipped with a magnetic stir bar, under argon was charged with thioacetal alcohol 3a (10 mg, 0.029 mmol, 1.0 equiv) and dichloromethane (1.5 mL). Pyridine (0.042 mg, 3.0 mg, 1.5 equiv) was added and the mixture was allowed to stir for 15 min. After 15 min S-t-butyl chlorothioformate (6.4 mg, 0.042 mmol, 1.5 equiv) was added and the reaction was allowed to stir under argon for 24 hr. After 24 hr the reaction was quenched with water (5 mL) and extracted with dichloromethane (3×10 mL). The organic layers were combined, dried over MgSO$_4$, and concentrated on a rotary evaporator at room temperature. The crude oil was purified via column chromatography (10% ethyl acetate in hexanes) to afford the desired S-t-butyl thiocarbamate 111 as a white amorphous solid (10.9 mg, 82% yield). Mp=102.4-103.9° C.; $[\alpha]_D^{22.1}$+2.40 (c. 0.29, CHCl$_3$); IR (thin film) ν 2961, 2922, 2872, 1706, 1455, 1377, 1125, 1036, 927, 879, 828 cm$^{-1}$; $^1$H NMR (300 MHz, CDCl$_3$) δ 5.27 (s, 1H), 4.52 (d, J=10.8 Hz, 1H), 4.30 (td, J=6.4, 0.9 Hz, 2H), 2.92-2.78 (m, 1H), 2.76-2.52 (m, 2H), 2.43-2.28 (m, 1H), 2.11-1.95 (m, 3H), 1.94-1.81 (m, 1H), 1.79-1.66 (m, 2H), 1.64-1.37 (m, 15H), 1.37-1.20 (m, 2H), 1.12-0.98 (m, 1H), 0.93 (dd, J=9.9, 6.6 Hz, 6H); $^{13}$C NMR (75 MHz, CDCl$_3$) δ 170.2, 104.4, 92.4, 80.8, 80.5, 65.3, 51.9, 47.2, 46.2, 37.5, 36.4, 34.2, 31.8, 30.3, 29.3, 26.1, 25.0, 24.9, 21.4, 20.4, 15.2; HRMS (FAB) m/z calcd for C$_{23}$H$_{38}$O$_6$S$_2$ [M+H]$^+$ 475.2188. found 475.2174.

Art-10α-S(CH$_2$)$_4$OC(O)SCH$_3$ (112)

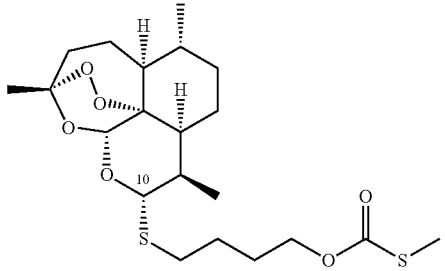

An oven-dried, 2-dram vial, equipped with a magnetic stir bar, under argon was charged with thioacetal alcohol 102 (10 mg, 0.027 mmol, 1.0 equiv) and dichloromethane (1.5 mL). Pyridine (0.041 mg, 3.0 mg, 1.5 equiv) was added and the mixture was allowed to stir for 15 min. After 15 min S-methyl chlorothioformate (4.5 mg, 0.041 mmol, 1.5 equiv) was added and the reaction was allowed to stir under argon for 24 hr. After 24 hr the reaction was quenched with water (5 mL) and extracted with dichloromethane (3×10 mL). The organic layers were combined, dried over MgSO$_4$, and concentrated on a rotary evaporator at room temperature. The crude oil was purified via column chromatography (10% ethyl acetate in hexanes) to afford the desired S-methyl thiocarbamate 112 as a white amorphous solid (9.5 mg, 79% yield). $[\alpha]_D^{24.6}$+22.63 (c. 0.49, CHCl$_3$); IR (thin film) ν 2955, 2926, 2871, 2847, 1710, 1451, 1378, 1349, 1277, 1259, 1230, 1200, 1151, 1091, 1036, 979, 929, 878, 827 cm$^{-1}$; $^1$H NMR (300 MHz, CDCl$_3$) δ 5.30 (s, 1H), 4.52 (d, J=10.7 Hz, 1H), 4.24 (t, J=6.1 Hz, 2H), 2.87-2.74 (m, 1H), 2.74-2.49 (m, 2H), 2.44-2.26 (m, 4H), 2.01 (ddd, J=14.5, 5.0, 3.0 Hz, 1H), 1.94-1.65 (m, 5H), 1.65-1.16 (m, 8H), 1.11-0.98 (m, 1H), 0.93 (dd, J=9.9, 6.6 Hz, 7H); $^{13}$C NMR (75 MHz, CDCl$_3$) δ 171.6, 104.3, 92.2, 80.5, 80.4, 67.1, 51.8, 46.0, 37.4, 36.3, 34.1, 31.7, 27.9, 26.2, 25.9, 24.8, 21.2, 20.2, 15.0, 13.4; HRMS (FAB) m/z calcd for C$_{21}$H$_{34}$O$_6$S$_2$ [M+H]$^+$ 447.1875. found 447.1851.

Art-10α-S(CH$_2$)$_4$OC(O)StBu (113)

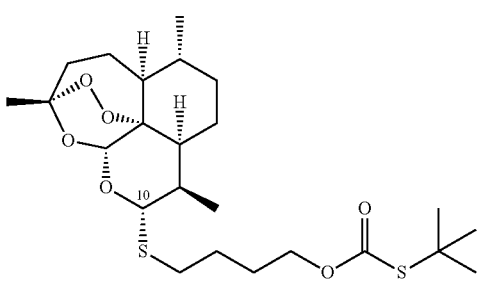

An oven-dried, 2-dram vial, equipped with a magnetic stir bar, under argon was charged with thioacetal alcohol 102 (10 mg, 0.027 mmol, 1.0 equiv) and dichloromethane (1.5 mL). Pyridine (0.041 mg, 3.0 mg, 1.5 equiv) was added and the mixture was allowed to stir for 15 min. After 15 min S-t-butyl chlorothioformate (6.2 mg, 0.041 mmol, 1.5 equiv) was added and the reaction was allowed to stir under argon for 24 hr. After 24 hr the reaction was quenched with water (5 mL) and extracted with dichloromethane (3×10 mL). The organic layers were combined, dried over MgSO$_4$, and concentrated on a rotary evaporator at room temperature. The crude oil was purified via column chromatography (10% ethyl acetate in hexanes) to afford the desired S-t-butyl thiocarbamate 113 as a white amorphous solid (10.5 mg, 80% yield). $[\alpha]_D^{24.1}$+10.68 (c. 0.93, CHCl$_3$); IR (thin film) ν 2961, 2924, 2870, 1706, 1452, 1372, 1277, 1259, 1229, 1199, 1127, 1037, 929, 878, 827, 754 cm$^{-1}$; $^1$H NMR (300 MHz, CDCl$_3$) δ 5.27 (s, 1H), 4.52 (d, J=10.8 Hz, 1H), 4.27-4.13 (m, 2H), 2.91-2.75 (m, 1H), 2.75-2.49 (m, 2H), 2.36 (ddd, J=14.5, 13.3, 4.0 Hz, 1H), 2.01 (ddd, J=14.5, 5.0, 2.9 Hz, 1H), 1.93-1.16 (m, 22H), 1.11-0.99 (m, 1H), 0.93 (dd, J=10.1, 6.6 Hz, 7H); $^{13}$C NMR (75 MHz, CDCl$_3$) δ 170.2, 104.3, 92.3, 92.2, 80.5, 80.4, 66.0, 51.8, 46.9, 37.4, 36.3, 34.1, 31.7, 30.1, 27.9, 27.8, 26.2, 25.9, 24.8, 21.3, 20.2, 15.0; HRMS (FAB) m/z calcd for C$_{24}$H$_{40}$O$_6$S$_2$ [M+H]$^+$ 489.2345. found 489.2330.

Art-10α-S(CH$_2$)$_3$OC(S)SCH$_3$ (114)

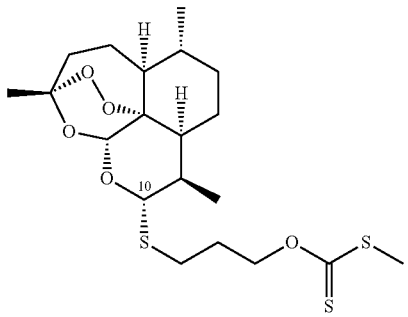

A 2-dram vial, equipped with magnetic stir bar and argon inlet adaptor, was charged with thioacetal 3a (19.6 mg, 0.058 mmol, 1 equiv) in anhydrous tetrahydrofuran (1.5 mL). The solution was cooled to 0° C. in an ice-water bath for 30 min. Sodium hydride (24 mg, 0.864 mmol, 15 equiv) was added as a solid in small portions to the stirring solution and the reaction was stirred at 0° C. for 10 min. Neat carbon disulfide (0.11 mL, 1.74 mmol, 30 equiv) was added dropwise and the reaction was allowed to warm to room temperature while vigorously stirring for 2 h. Neat iodomethane (0.16 mL, 2.61 mmol, 45 equiv) was added dropwise and the reaction was stirred at room temperature overnight. The reaction was quenched with saturated ammonium chloride (2 mL) and extracted with dichloromethane (3×2 mL). The organic layers were pooled, dried with MgSO$_4$, vacuum filtered, and concentrated by rotary evaporation at room temperature. The crude residue was purified by flash chromatography on silica, (5-20% EtOAc in hexanes) to yield xanthate ester 114 as a light yellow oil (18.2 mg, 70%). $[\alpha]_D^{22.2}$+5.2 (c. 0.38, CHCl$_3$); IR (thin film) ν 2973-2847, 1377, 1228, 1206, 1195, 1179, 1128, 1085, 1065, 1052, 1036, 1016, 928 cm$^{-1}$; $^1$H NMR (300 MHz, CDCl$_3$) δ 5.28 (s, 1H), 4.72 (t, J=6.4 Hz, 2H), 4.53 (d, J=10.7 Hz, 1H), 2.93 (dt, J=13.7, 7.0 Hz, 1H), 2.73 (dt, J=13.3, 7.4 Hz, 1H), 2.61 (ddd, J=13.1, 7.3, 4.2 Hz, 1H), 2.55 (s, 3H), 2.43-2.28 (m, 1H), 2.28-2.13 (m, 2H), 2.01 (ddd, J=14.5, 4.9, 2.9 Hz, 1H), 1.93-1.81 (m, 1H), 1.78-1.66 (m, 2H), 1.66-1.16 (m, 8H), 1.11-0.99 (m, 1H), 0.96-0.91 (m, 6H); $^{13}$C NMR (75 MHz, CDCl$_3$) δ 215.9, 104.5, 92.4, 80.8, 80.5, 72.9, 51.9, 46.2, 37.6, 36.4, 34.2, 31.8, 29.0, 26.1, 25.0, 24.9, 21.6, 20.4, 19.1, 15.2; HRMS (FAB) m/z calcd for C$_{20}$H$_{32}$O$_5$S$_3$ (M)+ 448.1412. found 448.1410.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Adjuik, M.; Babiker, A.; Garner, P.; Olliaro, P.; Taylor, W.; White, N., Artesunate combinations for treatment of malaria: meta-analysis Lancet 2004, 363, 9-17;

Arinaitwe, E.; Sandison, T. G.; Wanzira, H.; Kakuru, A.; Homsy, J.; Kalamya, J.; Kamya, M. R; Vora, N.; Greenhouse, B.; Rosenthal, P. J.; Tappero, J.; Dorsey, G. Artemether-Lumefantrine versus Dihydroartemisinin-Piperaquine for Falciparum Malaria: A Longitudinal, Randomized Trial in Young Ugandan Children. Clin. Infect. Dis. 2009, 49, 1629-1637;

Ashley, E. A.; White, N. J. Artemisinin-based combinations Curr. Opin. Infect. Dis. 2005, 18, 531-536;

Bachmann, S., J. Schroder, C. Bottmer, E. F., Torrey, and R. H. Yolken. 2005. Psychopathology in first-episode schizophrenia and antibodies to *Toxoplasma gondii*. Psychopathol. 38(2): 87-90;

Begue J-P, Bonnet-Delpon D. Fluoroartemisinins: metabolically more stable antimalarial artemisinin derivatives. Chem Med Chem 2007, 2, 608-624;

Berens, R. L., E. C. Krug, P. B. Nash, and T. J. Curiel. 1998. Selection and characterization of *Toxoplasma gondii* mutants resistant to artemisinin. J. Infect. Dis. 177:1128-1131;

Bigot A, Breit B. A convenient allylic functionalization of bis(prop-2-enyl)methanol by direct trimetalation. Synthesis 2008, 22, 3692-3696;

Chadwick J, Mercer A E, Park B K, Cosstick R, O'Neill P M. 2009. Synthesis and biological evaluation of extraordinarily potent C-10 carba artemisinin dimers against P-falciparum malaria parasites and HL-60 cancer cells. BioorgMed Chem 17: 1325-1338;

Chang, H. R, C. W. Jefford, and J.-C. Pechere. 1989. In vitro effects of three new 1,2,4-trioxanes (pentatroxane, thiahexatroxane, and hexatroxanone) on *Toxoplasma gondii*. Antimicrob. Agents Chemother. 33(10): 1748-1752;

Chen, X.; Chong, C. R; Shi, L; Yoshimoto, T.; Sullivan, D. J., Jr.; Lin, J. O. Inhibitors of *Plasmodium falciparum* methionine aminopeptidase Ib possess antimalarial activity Proc. Natl. Acad. Sa. U.S.A. 2006, 103, 14548-14553;

de Pilla Varotti, F.; Botelho, A. C. C; Andrade, A. A.; de Paula, R C; Fagundes, E. M. S.; Valverde, A; Mayer, L. M. U.; Mendonca, J. S.; de Souza, M. V. N.; Boechat, N.; Krettli, A. U. Synthesis, antimalarial activity, and intracellular targets of MEFAS, a new hybrid compound derived from mefloquine and artesunate Antimicrob. Agents Chemother. 2008, 52, 3868-3874;

Eastman, R. T.; Fidock, D. A. Artemisinin-based Combination Therapies: A Vital Tool in Efforts to Eliminate Malaria. Nat. Rev. Micro. 2009, 7, 864-874;

Fanello, C. I.; Karema, C; van Doren, W.; Van Overmeir, C; Ngamije, D.; D'Alessandro, U. A randomised trial to assess the safety and efficacy of artemether-lumefantrine (Coartem®) for the treatment of uncomplicated *Plasmodium falciparum* malaria in Rwanda. Trans. R. Soc. Trop. Med. Hyg. 2007, 101, 344-350;

Gautam, A.; Ahmed, T.; Batra, V.; Paliwal, J., Pharmacokinetics and Pharmacodynamics of Endoperoxide Antimalarials Curr. Drug. Metab. 2009, 10, 289-306;

Gately, S.; West, R Novel Therapeutics With Enhanced Biological Activity Generated by the Strategic Introduction of Silicon Isosteres into Known Drug Scaffolds. Drug Dev. Res. 2007, 68, 156-163;

Gelb M. H. Drug discovery for malaria: a very challenging endeavor. Curr Opin Chem Biol 2007, 11, 440-445;

Georgiev, V. S. 1994. Management of toxoplasmosis. Drugs. 48(2):179-188. Greene, T. W.; Wuts, P. G. M., *Protective Groups in Organic Synthesis*. Third ed.; Wiley-Interscience;

*Guidelines for the Treatment of Malaria*. Second ed.; 2010;

Guthmann, J.-P.; Cohuet, S.; Rigutto, C; Fortes, F.; Saraiva, N.; Kiguli, J.; Kyomuhendo, J.; Francis, M.; Noel, F.; Mulemba, M. Balkan, S. High efficacy of two artemisinin-based combinations (artesunate+amodiaquine and artemether+lumefantrine) in Caala, Central Angola. J. Trop. Med. Hyg. 2006, 75, 143-145;

Haynes, R. K. From artemisinin to new artemisinin antimalarials: biosynthesis, extraction, old and new derivatives, stereochemistry and medicinal chemistry requirements. Curr Top Med Chem 2006, 6, 509-537;

H of, Fraser; Schütz, Andri; Fäh, Christoph; Meyer, Solange; Bur, Daniel; Liu, Jun; Goldberg, D. E.; Diederich, F. Starving the Malaria Parasite. Inhibitors Active Against the Aspartic Proteases Plasmepsins I, II, and IV. Angew. Chem. Int. Ed. 2006, 45, 2138-2141;

Holfels, E., J. McAuley, D. Mack, W. K. Milhous, and R. McLeod. 1994. In vitro effects of artemisinin ether, cycloguanil hydrochloride (alone and in combination with sulfadiazine), quinine sulfate, mefloquine, primaquine phosphate, trifluoperazine hydrochloride, and verapamil on *Toxoplasma gondii*. Antimicrob. Agents Chemother. 38(6):1392-1396;

Jefford, C. W. Synthetic peroxides as antimalarials. Curr Opin Invest Drugs (Thomson Set.) 2004, 5, 866-872;

Jones-Brando, L., E. F. Torrey, and R. Yolken. 2003. Drugs used in the treatment of schizophrenia and bipolar disorder inhibit the replication of *Toxoplasma gondii*. Schizophr. Res. 62:237-244;

Jung, M.; Lee, S., *Bioorg. Med. Chem. Lett.* 1998, 8, 1003-1006;

Jung, M.; Lee, S.; Ham, J.; Lee, K.; Kim, H.; Kim, S. K., Antitumor activity of novel deoxoartesmisinin monomers, dimers, and trimer J. Med. Chem. 2003, 46, 987-994;

Kelly, J. X.; Smilkstein, M. J.; Brun, R; Wittlin, S.; Cooper, R A.; Lane, K. D.; Janowsky, A.; Johnson, R. A.; Dodean, R. A.; Winter, R.; Hinrichs, D. J.; Riscoe, M. K. Discovery of dual function acridones as a new antimalarial chemotype. Nature 2009, 459, 270-273;

Klayman, D. L. Qinghaosu (artemisinin): an antimalarial drug from China. Science 1985, 228, 1049-1055;

LeBlanc, R.; Vasquez, Y.; Hannaman, D.; Kumar, N. Markedly Enhanced Immunogenicity of a Pfs25 DNA Based Malaria Transmission Blocking Vaccine by in Vivo Electroporation. Vaccine 2008, 26, 185-192;

Lee, S.; Oh, S.; Park, G.-M.; Kim, T.-S.; Ryu, J.-S.; Choi, H.-K., *Korean J. Parasitol.* 2005, 43, 123-126;

Lin A. J., D. L. Klayman, and W. K Milhous. 1987. Antimalarial activity of new water-soluble dihydroartemisinin derivatives. J. Med. Chem. 30:2147-2150;

Moon, D. K.; Singhal, V.; Kumar, N.; Shapiro, T. A.; Posner, G. H. Antimalarial Preclinical Drug Development: A Single Oral Dose of A 5-Carbon-linked Trioxane Dimer Plus Mefloquine Cures Malaria-Infected Mice. Drug Dev. Res. 2009, 71(1), 76-81;

Myint, H. Y.; Ashley, E. A.; Day, N. P. J.; Nosten, F.; White, N. J., Efficacy and safety of dihydroartemisinin-piperaquine Trans. R. Soc. Trop. Med. Hyg. 2007, 101, 858-866;

Oh, S.; Jeong, I. H.; Shin, W.-S.; Lee, S., *Bioorg. Med. Chem. Lett.* 2003, 13, 3665-3668;

Olliaro, P. L.; Boland, P. B. Clinical public health implications of antimalarial drug resistance. In Antimalarial Chemotherapy: Mechanisms of Action, Resistance, and New Directions in Drug Discovery; Rosenthal, P. J., Ed.; Humana Press: Totowa, N.J., 2001; pp 65-83;

O'Neill P. M., Posner G. H. A medicinal chemistry perspective on artemisinin and related endoperoxides. J Med Chem 2004, 47, 2945-2964;

Ou-Yang, K., E. C. Krug, J. J. Marr, and R. L. Berens. 1990 Inhibition of growth of *Toxoplasma gondii* by Qinghaosu and derivatives. Antimicrob. Agents Chemother. 34(10): 1961-1965;

Paik I-H, Xie S, Shapiro T A, Labonte T, Sarjeant A A N, Baege A C, Posner G H. 2006. Second generation, orally active, antimalarial, artemisinin-derived trioxane dimers with high stability, efficacy, and anticancer activity. J Med Chem 2006, 49, 2731-2734;

Pandey, K. C; Sijwall, P. S.; Singh, A; Na, B.-K.; Rosenthal, P. J. Independent Intramolecular Mediators of Folding, Activity, and Inhibition for the *Plasmodium falciparum* Cysteine Protease Falcipain-2. J. Biol. Chem. 2004, 279, 3484-3491;

Plowe, C. V., *Curr. Top. Microbiol. Immunol.* 2005, 295, 55-79;

Posner, G H.; Paik, I.-H.; Sur, S.; McRiner, A. J.; Borstnik, K.; Xie, S.; Shapiro, T. A., Orally active, antimalarial, anticancer, artemisinin-derived trioxane dimers with high stability and efficacy J. Med. Chem. 2003, 46, 1060-1065;

Posner G H., Paik L-H., Chang W., Borstnik K., Sinishtaj S., Rosenthal A. S., Shapiro T. A. Malaria-infected mice are cured by a single dose of novel artemisinin derivatives. J Med Chem 2007, 50, 2516-2519;

Posner G. H., Chang W., Hess L., Woodard L., Sinishtaj S., Usera A. R, Maio W., Rosenthal A. S., Kalinda A. S., D'Angelo J. G, Petersen K. S., Stohler R., Chollet J., Santo-Tomas J., Synder C, Rottmann M., Wittlin S., Brun R, Shapiro T. A. Malaria-infected mice are cured by oral administration of new artemisinin derivatives. J Med Chem 2008, 51, 1035-1042;

Ramanathan-Girish, S.; Catz, P.; Creek, M. R; Wu, B.; Thomas, D.; Krogstad, D. J., De, D.; Mirsalis, J. C; Green, C. E. Pharmacokinetics of the Antimalarial Drug, AQ-13, in Rats and Cynomolgus Macaques. Int. J. Toxicol. 2004, 23, 179-189;

Ridley, R. G. Medical Need, Scientific Opportunity, and the Drive for Antimalarial Drugs. Nature 2002, 415, 686-693;

Rosenthal, A. S.; Chen, X.; Liu, J. O.; West, D. C.; Hergenrother, P. J.; Shapiro, T. A.; Posner, G. H., Malaria-infected mice are cured by a single oral dose of new dimeric trioxane sulfones which are also selectively and powerfully cytotoxic to cancer cells J. Med. Chem. 2009, 52, 1198-1203;

Sagara, I.; Diallo, A. D.; Kone, M.; Coulibaly, M.; Diawara, S. I.; Guindo, O.; Maiga, H.; Niambele, M. B.; Sissoko, M.; Dicko, A.; Djimde, A.; Doumbo, O. K. A randomized trial of artesunate-mefloquine versus artemether-lumefantrine for treatment of uncomplicated *Plasmodium falciparum* malaria in Mali Am. J. Trop. Med. Hyg. 2008, 79, 655-661;

Sagara, I.; Rulisa, S.; Mbacham, W.; Adam, I.; Sissoko, K.; Maiga, H.; Traore, O. B.; Dara, N.; Dicko, Y. T.; Dicko, A.; Djimde, A.; Jansen, F. H.; Doumbo, 0. K., Efficacy and safety of a fixed dose artesunate-sulphamethoxypyrazine-pyrimethamine compared to artemether-lumefantrine for the treatment of uncomplicated falciparum malaria across Africa: a randomized multicentre trial Malar. J. 2009, 8, 63-73;

Shizhen L. 2003. Compendium of Materia Medica (Bencao Gangmu); first published in Chinese in 1593, translation published 2003. Beijing, China: Foreign Languages Press.

Sirima, S. B.; Tiono, A. B.; Gansane, A.; Diarra, A.; Ouedraogo, A.; Konate, A. T.; Kiechel, J. R.; Morgan, C. C; Olliaro, P. L.; Taylor, W. R. J. Malar. J. 2009, 8, 48;

Satchell, D. P. N.; Satchell, R. S., *Chem. Soc. Rev.* 1990, 19, 55-81;

Slack, R. D.; Mott, B. M.; Woodard, L. E.; Tripathi, A.; Sullivan, D.; Nenortas, E.; Girdwood, S. C. T.; Shapiro, T. A.; Posner, G. H., *J. Med. Chem.* 2012, 55, 291-296;

Souares A., Lalou R., Sene I., Sow D., Le Hesran J.-Y. 2009. Factors related to compliance to anti-malarial drug combination: example of amodiaquine/sulphadoxine-pyrimethamine among children in rural Senegal. Malar J 2009, 8, 118-125;

Tang Y, Dong Y, Vennerstrom J L. 2004. Synthetic peroxides as antimalarials. Med Res Rev 2004, 24, 425-448;

Tenter, A. M., A. R Heckeroth, and L. M. Weiss. 2000. *Toxoplasma gondii*: from animals to humans. Intl. J. Parasitol. 30:1217-1258;

Torrey E F, Bartko J J, Lun Z R, Yolken R H. 2007. Antibodies to *Toxoplasma gondii* in patients with schizophrenia: a meta-analysis. Schizophr Bull. 33(3):729-736;

Troye-Blomberg, M.; Berzins, K. Rational Vaccine Development against Malaria. Microbes Infect. 2007, 9, 749-750;

Vennerstrom, J. L.; Arbe-Barnes, S.; Brun, R.; Charman, S. A.; Chiu, F. C. K.; Chollet, J.; Dong, Y.; Dorn, A.; Hunziker, D.; Matile, H.; McIntosh, K.; Padmanilayam, M.; Santo, T. J.; Scheurer, C; Scorneaux, B.; Tang, Y.; Urwyler, H.; Wittlin, S.; Charman, W. N., Identification of an antimalarial synthetic trioxolane drug development candidate Nature 2004, 430, 900-904;

Venugopalan, B.; Karnik, P. J.; Bapat, C. P.; Chatterjee, D. K.; Iver, N.; Lepcha, D., *Eur. J. Med. Chem.* 1995, 30, 697-706;

World Health Organization. Guidelines for the Treatment of Malaria; WHO: Geneva, Switzerland, 2006;

*World Malaria Report* 2011; World Health Organization: Geneva;

Woodard, L. E.; Chang, W.; Chem, X.; Liu, J. O.; Shapiro, T. A; Posner, G. H. Malaria-Infected Mice Live until at Least Day 30 after a New Monomeric Trioxane Combined with Mefloquine are Administered Together in a Single Low Dose. J. Med. Chem. 2009, 52(23), 7458-62; and Yearick, K.; Ekoue-Kovi, K.; Iwaniuk, D. P.; Natarajan, J. K.; Alumasa, J.; de Dios, A. C; Roepe, P. D.; Wolf, C. Overcoming Drug Resistance to Heme-targeted Antimalarials by Systematic Side Chain Variation of 7-Chloro-4-aminoquinolines. J. Med. Chem. 2008, 51, 1995-1998.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A compound of Formula (I):

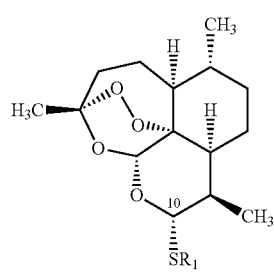

wherein:
$R_1$ is —$(CH_2)_n$—O—$R_{2a}$ or —$(CH_2)_{n-1}$—C(=O)—$R_{2b}$, wherein n is an integer from 2 to 11; and
$R_{2a}$ is selected from the group consisting of —$CH_2C\equiv CH$; —$CH_2$—C(=$CH_2$)$R_3$, wherein $R_3$ is halogen; —$CH_2$—$R_4$, wherein $R_4$ is selected from the group consisting of:

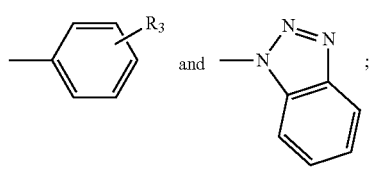

wherein $R_3$ is as defined above; and —(C=$X_1$)—$R_5$; wherein $X_1$ is O or S; and $R_5$ is selected from the group consisting of substituted or unsubstituted alkyl, alkoxyl, substituted or unsubstituted aryl, —$SR_6$, —$NR_6R_7$; wherein $R_6$ and $R_7$ are each selected from the group consisting of H, substituted or unsubstituted alkyl; and
$R_{2b}$ is selected from the group consisting of substituted or unsubstituted alkoxyl; substituted or unsubstituted aryloxyl; and —$NR_6R_7$, wherein $R_6$ and $R_7$ are as defined above;
or an enantiomer, diastereomer, racemate or pharmaceutically acceptable salt thereof.

2. The compound of claim 1, wherein $R_1$ is —$(CH_2)_n$—O—$R_{2a}$ and $R_{2a}$ is selected from the group consisting of —$CH_2C\equiv CH$; —$CH_2$—C(=$CH_2$)Cl; —(C=O)—$CH_3$; —(C=O)—C($CH_3$)$_3$; —(C=O)—N($CH_2CH_3$)$_2$; —(C=O)—N(CH($CH_3$)$_2$)$_2$; —(C=O)—S—$CH_3$; —(C=O)—S—$CH_2CH_3CH_3$; —(C=O)—S—C($CH_3$)$_3$; —(C=S)—S—$CH_3$; —(C=O)-(halogenated phenyl); —(C=O)—$OR_8$, wherein $R_8$ is selected from the group consisting of substituted or unsubstituted alkyl, substituted or unsubstituted alkenyl, substituted or unsubstituted alkynyl, and substituted or unsubstituted aryl;

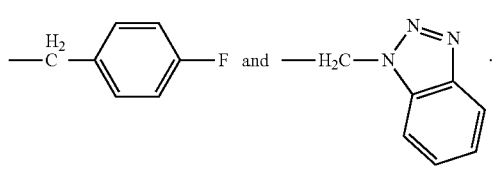

3. The compound of claim 2, wherein the compound of Formula (I) is selected from the group consisting of:

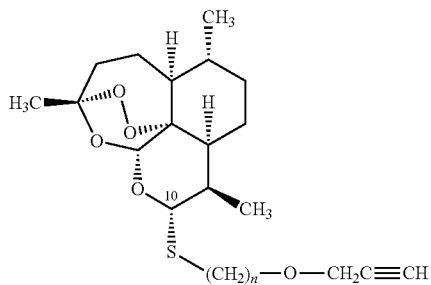

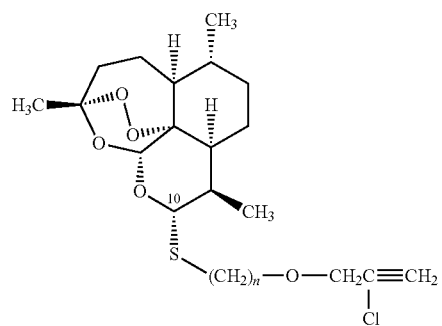

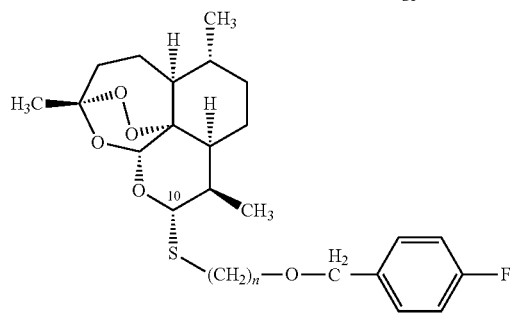

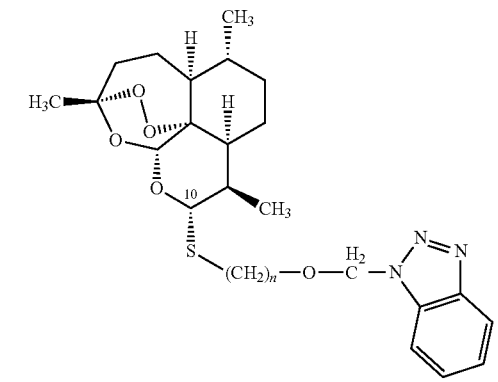

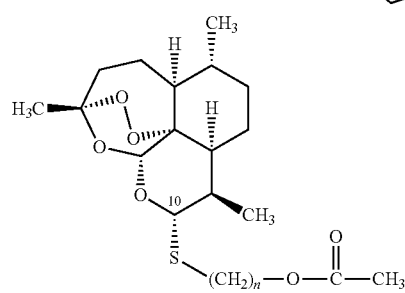

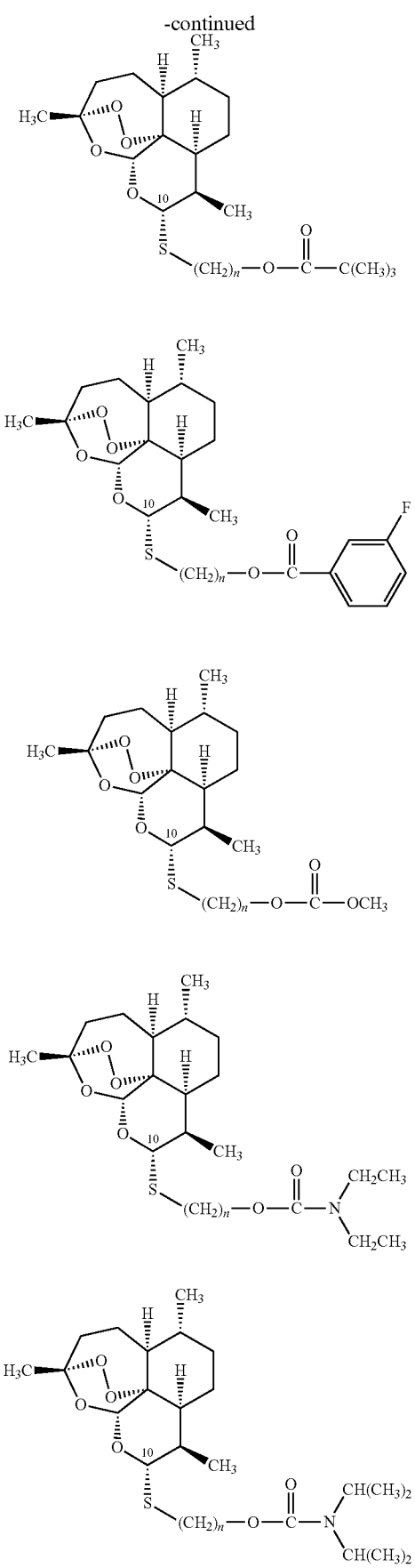
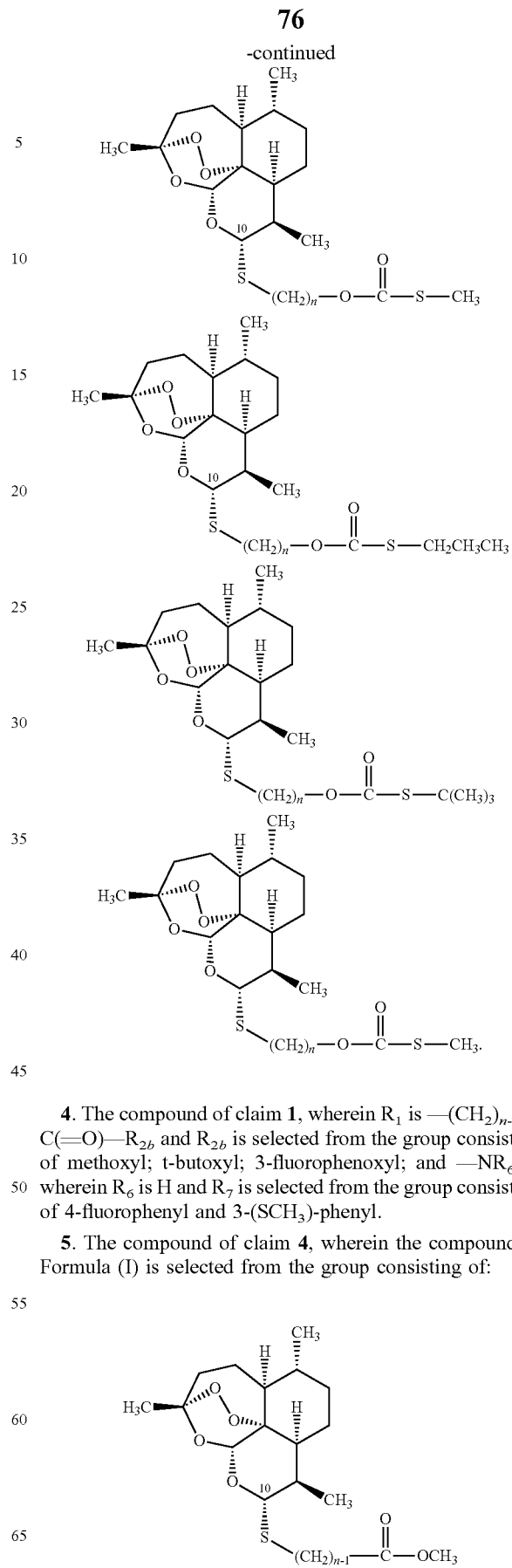
4. The compound of claim 1, wherein $R_1$ is —$(CH_2)_{n-1}$—C(=O)—$R_{2b}$ and $R_{2b}$ is selected from the group consisting of methoxyl; t-butoxyl; 3-fluorophenoxyl; and —$NR_6R_7$, wherein $R_6$ is H and $R_7$ is selected from the group consisting of 4-fluorophenyl and 3-($SCH_3$)-phenyl.
5. The compound of claim 4, wherein the compound of Formula (I) is selected from the group consisting of:
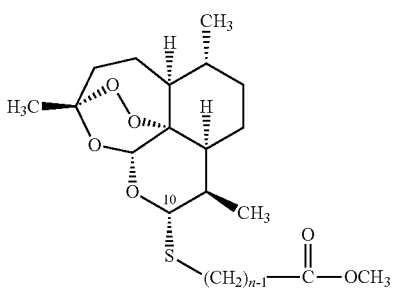

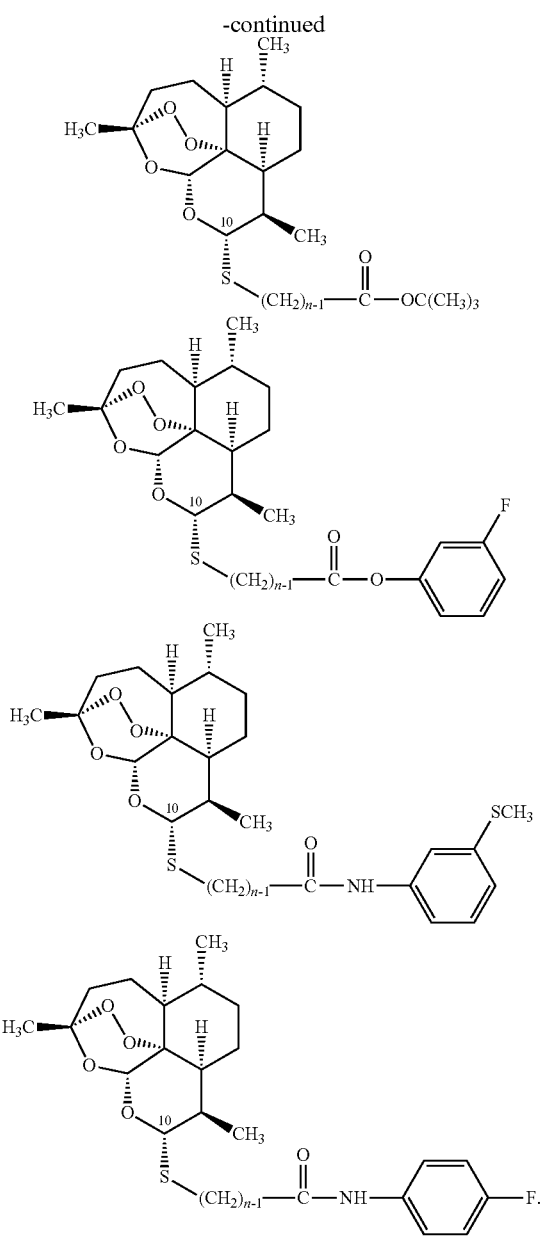

6. A compound of Formula (II):

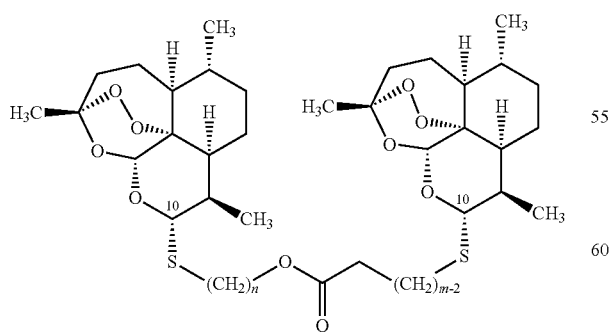

wherein:

m and n can be the same or different and are each independently an integer selected from 3 or 6; or an enantiomer, diastereomer, racemate or pharmaceutically acceptable salt thereof.

7. A compound of Formula (III):

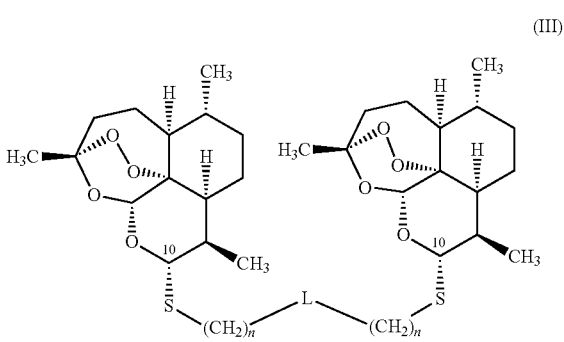

wherein:

each n is an integer independently selected from the group consisting of 3 and 6;

L is a linking group selected from the group consisting of:

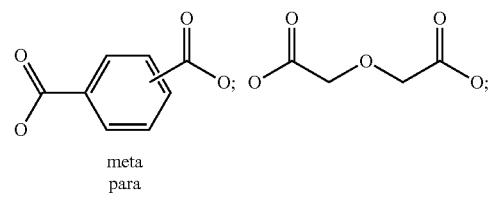

meta
para

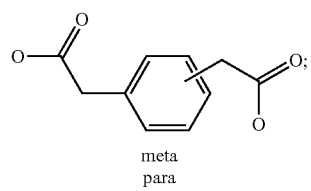

meta
para

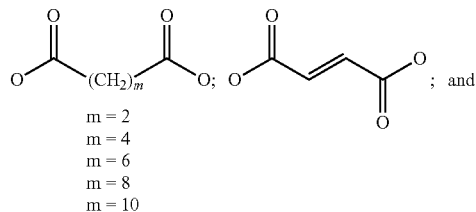

m = 2
m = 4
m = 6
m = 8
m = 10

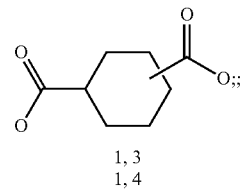

1, 3
1, 4 or an enantiomer, diastereomer, racemate or pharmaceutically acceptable salt thereof.

8. A compound of Formula (IV):

(IV) [structure]

wherein:
each n is an integer independently selected from the group consisting of 3 and 6;
L is a linking group selected from the group consisting of:

[structures showing linking groups with O—...—O; including benzyl, glycerol, alkenyl, ethylene glycol, cyclohexyl 1,3/1,4, and O—(CH₂)ₘ—O]

wherein:
m is an integer from 2 to 8;
R is selected from the group consisting of alkyl, cycloalkyl, heteroalkyl, aryl, and heteroaryl, each of which can be substituted or unsubstituted; or
an enantiomer, diastereomer, racemate or pharmaceutically acceptable salt thereof.

9. A compound of Formula (V):

(V) [structure]

wherein:
each n is an integer independently selected from the group consisting of 3 and 6;
L is a linking group selected from the group consisting of:

[structures showing linking groups with HN—...—NH; including benzyl diamine, propylene diamine with R, neopentyl diamine with 2R, allylic diamine, diethylene glycol diamine, cyclohexyl 1,3/1,4 diamine, and HN—(CH₂)ₘ—NH]

wherein:
m is an integer from 2 to 8;
R is selected from the group consisting of alkyl, cycloalkyl, heteroalkyl, aryl, and heteroaryl, each of which can be substituted or unsubstituted; or
an enantiomer, diastereomer, racemate or pharmaceutically acceptable salt thereof.

10. A pharmaceutical composition comprising a compound of claim 1.

11. A method for controlling malaria in a subject in need of such treatment, the method comprising administering to the subject a therapeutically-effective amount of a compound of Formula (I-V) or an enantiomer, diastereomer, racemate or pharmaceutically acceptable salt thereof.

12. The method of claim 11, wherein the malaria comprises a *Plasmodium* parasite infection.

13. The method of claim 11, further comprising administering to the subject a quinoline anti-malarial drug or an antifolate concurrently or sequentially with the compound of Formula (I-V).

14. The method of claim 13, wherein the wherein the quinoline anti-malarial drug is selected from the group consisting of chloroquine, quinine, mefloquine, and primaquine.

15. The method of claim 13, wherein the antifolate is lumefantrine.

* * * * *

UNITED STATES PATENT AND TRADEMARK OFFICE
CERTIFICATE OF CORRECTION

PATENT NO. : 9,611,273 B2
APPLICATION NO. : 14/381494
DATED : April 4, 2017
INVENTOR(S) : Gary H. Posner et al.

It is certified that error appears in the above-identified patent and that said Letters Patent is hereby corrected as shown below:

In the Specification

Column 1, Lines 14-19, should read:
STATEMENT OF GOVERNMENTAL INTEREST
This invention was made with government support under AI034885, awarded by the National Institutes of Health. The government has certain rights in the invention.

Signed and Sealed this
Thirteenth Day of July, 2021

Drew Hirshfeld
*Performing the Functions and Duties of the
Under Secretary of Commerce for Intellectual Property and
Director of the United States Patent and Trademark Office*